(12) United States Patent
Simpson et al.

(10) Patent No.: US 8,586,345 B2
(45) Date of Patent: *Nov. 19, 2013

(54) ELECTROPROCESSED COLLAGEN AND TISSUE ENGINEERING

(75) Inventors: David G. Simpson, Mechanicsville, VA (US); Gary L. Bowlin, Mechanicsville, VA (US); Gary E. Wnek, Midlothian, VA (US); Peter J. Stevens, N. Richland Hills, TX (US); Marcus E. Carr, Midlothian, TX (US); Jamil A. Matthews, Glen Allen, VA (US); Saravanamoorthy Rajendran, East Haven, CT (US)

(73) Assignee: Virginia Commonwealth University Intellectual Property Foundation, Richmond, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/052,778

(22) Filed: Mar. 21, 2011

(65) Prior Publication Data

US 2011/0288026 A1  Nov. 24, 2011

Related U.S. Application Data

(63) Continuation of application No. 11/842,748, filed on Aug. 21, 2007, now abandoned, which is a continuation of application No. 10/447,670, filed on May 28, 2003, now Pat. No. 7,615,373, which is a continuation-in-part of application No. 09/991,373, filed on Nov. 16, 2001, now abandoned, which is a continuation-in-part of application No. 09/714,255, filed on Nov. 17, 2000, now abandoned, which is a continuation-in-part of application No. 09/512,081, filed on Feb. 24, 2000, now abandoned, and a continuation-in-part of application No. 09/386,273, filed on Aug. 31, 1999, now Pat. No. 6,592,623.

(60) Provisional application No. 60/121,628, filed on Feb. 25, 1999, provisional application No. 60/384,035, filed on May 28, 2002, provisional application No. 60/386,612, filed on Jun. 6, 2002, provisional application No. 60/396,399, filed on Jul. 15, 2002, provisional application No. 60/402,189, filed on Aug. 8, 2002.

(51) Int. Cl.
| | | |
|---|---|---|
| C07K 1/00 | (2006.01) |
| C12N 5/00 | (2006.01) |
| C12N 5/02 | (2006.01) |
| A61K 38/17 | (2006.01) |
| A61F 2/06 | (2013.01) |

(52) U.S. Cl.
USPC .......... 435/273; 435/398; 435/399; 530/356; 623/1.47

(58) Field of Classification Search
USPC .......... 435/273, 398, 399; 530/356; 623/1.47
See application file for complete search history.

(56) References Cited

U.S. PATENT DOCUMENTS 4,455,206 A * 6/1984 Funabashi et al. ............ 204/483
6,103,255 A * 8/2000 Levene et al. ................. 424/426
7,615,373 B2 * 11/2009 Simpson et al. .............. 435/398

FOREIGN PATENT DOCUMENTS

WO  WO 98/03267  *  1/1998

OTHER PUBLICATIONS

Avicon, Inc., 1980, JP-55(1980)-6061, p. 1-2.*
Bango et al., 2003, US 20030193118 A1.*

* cited by examiner

*Primary Examiner* — Shin-Lin Chen
(74) *Attorney, Agent, or Firm* — Whitham Curtis Christofferson & Cook, PC

(57) ABSTRACT

The invention is directed to formation and use of electroprocessed collagen, including use as an extracellular matrix and, together with cells, its use in forming engineered tissue. The engineered tissue can include the synthetic manufacture of specific organs or tissues which may be implanted into a recipient. The electroprocessed collagen may also be combined with other molecules in order to deliver substances to the site of application or implantation of the electroprocessed collagen. The collagen or collagen/cell suspension is electrodeposited onto a substrate to form tissues and organs.

8 Claims, 14 Drawing Sheets

ELECTROPROCESSED COLLAGEN AND TISSUE ENGINEERING

PRIOR RELATED APPLICATIONS

This application is a continuation of U.S. Non-Provisional patent application Ser. No. 11/842,748 filed Aug. 21, 2007, now abandoned, which is a continuation of U.S. Non-Provisional patent application Ser. No. 10/447,670, filed May 28, 2003, now issued as U.S. Pat. No. 7,615,373, which is a continuation-in-part of U.S. Non-Provisional patent application Ser. No. 09/991,373 filed Nov. 16, 2001, which is a continuation-in-part of U.S. Non-Provisional patent application Ser. No. 09/714,255, filed Nov. 17, 2000, which is a continuation-in-part of U.S. Non-Provisional patent application Ser. No. 09/512,081, filed Feb. 24, 2000, which is a continuation-in-part of U.S. Non-Provisional patent application Ser. No. 09/386,273, filed Aug. 31, 1999. U.S. Non-Provisional patent application Ser. No. 09/512,081 also claims priority, in part, from U.S. Provisional Application Ser. No. 60/121,628, filed on Feb. 25, 1999. This application further claims priority from U.S. Provisional Application Ser. No. 60/384,035, filed May 28, 2002; U.S. Provisional Application Ser. No. 60/386,612, filed Jun. 6, 2002; U.S. Provisional Application Ser. No. 60/396,399, filed Jul. 15, 2002; and U.S. Provisional Application Ser. No. 60/402,189, filed Aug. 8, 2002.

FIELD OF THE INVENTION

The present invention comprises electroprocessed collagen, compositions comprising electroprocessed collagen, use of electroprocessed collagen as an extracellular matrix for numerous functions and novel methods of making and using electroprocessed collagen. Further, the invention includes combining electroprocessed collagen and cells to form engineered tissue. The engineered tissue can include the synthetic manufacture of specific organs or "organ-like" tissue.

BACKGROUND OF THE INVENTION

There is a continuing need in biomedical sciences for biocompatible compositions that can be used in manufacturing devices for implantation within or upon the body of an organism. Much of the focus in the past has concerned use of synthetic polymers. Many such polymers, however, suffer the drawbacks associated with their chemical and structural dissimilarities with natural materials. Fibrotic encapsulation, lack of cellular infiltration, and rejection are problems experienced by such implants. Efforts to overcome these issues have focused in part on use of biodegradable synthetic polymers as scaffolding to engineer prosthetic constructs to improve biocompatibility. Many such polymers, however, suffer the drawback of producing major degradation by-products that, in intimate contact with to individual cells, can produce an inflammatory response and decrease the pH in the cellular microenvironment. Thus, steps must be taken to ensure proper by-product removal from the tissue-engineered construct when using biodegradable materials. Another complication is that bioabsorbable structural materials are degraded over time, resulting in structural failure of the implant. Fibrotic encapsulation and lack of cellular infiltration also remain problems.

To overcome the drawbacks associated with synthetic implants, attention has turned toward use of collagen implants. Collagens are a family of proteins that are widely distributed throughout the body. This scaffolding material is one of the most prominent proteins present in animal tissue. Collagen is the principle structural element of most extracellular matrices and, as such, is a critical structural element of most tissues. There are several forms of collagen that exist in different types of tissue and organs.

To date, most efforts with collagen have focused on the use of collagen gels or solid collagen constructs such as films. A problem with these constructs is that they either lack structural strength (as with collagen gels) or lose strength after implantation. Harder collagen implants are broken down because their architecture and orientation differs from that of native tissues. Cells remodel implanted collagen to conform to the architecture and fiber orientation of normal extracellular matrices. This process causes structurally sound implants to lose integrity after implantation and ultimately to fail.

Thus, there exists a need in the art for collagen materials that may be used to form biocompatible implants that possess structural integrity and retain such integrity after implantation. Preferably, such materials should be able to mimic the chemistry and structure of extracellular matrices and promote infiltration of cells.

SUMMARY OF THE INVENTION

The compositions of the present invention comprise electroprocessed collagen. The invention includes collagen electroprocessed by any means. The electroprocessed collagen can constitute or be formed, for example, from natural collagen, genetically engineered collagen, or collagen modified by conservative amino acid substitutions, non-conservative amino acid substitutions or substitutions with non-naturally occurring amino acids. The collagen used in electroprocessing can be derived from a natural source, manufactured synthetically, or produced through any other means. Numerous methods for producing collagens and other proteins are known in the art. Synthetic collagen can be prepared to contain specific desired amino acid sequences. The electroprocessed collagen can also be formed from collagen itself or any other material that forms a collagen structure when electroprocessed. Examples include, but are not limited to amino acids, peptides, denatured peptides such as gelatin from denatured collagen, polypeptides, and proteins. Collagen can be formed either before, during, or after electroprocessing. Thus, electroprocessed collagen formed by combining procollagen with procollagen peptidase either before, during, or after electroprocessing is within the scope of the invention.

In some embodiments, the composition of the present invention includes additional electroprocessed materials. Other electroprocessed materials can include natural materials, synthetic materials, or combinations thereof. Some preferred examples of natural materials include, but are not limited to, amino acids, peptides, denatured peptides such as gelatin from denatured collagen, polypeptides, proteins, carbohydrates, lipids, nucleic acids, glycoproteins, lipoproteins, glycolipids, glycosaminoglycans, and proteoglycans. Some preferred synthetic matrix materials for electroprocessing with collagen include, but are not limited to, polymers such as poly(lactic acid) (PLA), polyglycolic acid (PGA), copolymers of PLA and PGA, polycaprolactone, poly(ethylene-co-vinyl acetate), (EVOH), poly(vinyl acetate) (PVA), polyethylene glycol (PEG) and poly(ethylene oxide) (PEO).

In many desirable embodiments, the electroprocessed collagen is combined with one or more substances. Such substances include any type of molecule, cell, or object or combinations thereof. The electroprocessed collagen compositions of the present invention can further comprise one substance or any combination of substances. Several especially desirable embodiments include the use of cells as a substance combined with the electroprocessed collagen matrix. Any cell can be used. Cells that can be used include, but are not limited to, stem cells, committed stem cells, and differentiated cells. Molecules can be present in any phase or form and combinations of molecules can be used. Examples of desirable classes of molecules that can be used include human or veterinary therapeutics, cosmetics, nutraceuticals, agriculturals such as herbicides, pesticides and fertilizers, vitamins, amino acids, peptides, polypeptides, proteins, carbohydrates, lipids, nucleic acids, glycoproteins, lipoproteins, glycolipids, glycosaminoglycans, proteoglycans, growth factors, hormones, neurotransmitters, pheromones, chalones, prostaglandins, immunoglobulins, monokines and other cytokines, humectants, metals, gases, plasticizers, minerals, ions, electrically and magnetically reactive materials, light sensitive materials, anti-oxidants, molecules that can be metabolized as a source of cellular energy, antigens, and any molecules that can cause a cellular or physiological response. Examples of objects include, but are not limited to, cell fragments, cell debris, organelles and other cell components, extracellular matrix constituents, tablets, and viruses, as well as vesicles, liposomes, capsules, nanoparticles, and other structures that serve as an enclosure for molecules. Magnetically or electrically reactive materials are also examples of substances that are optionally included within compositions of the present invention. Examples of electrically active materials include, but are not limited to, carbon black or graphite, carbon nanotubes, and various dispersions of electrically conducting polymers. Examples of magnetically active materials include, but are not limited to, ferrofluids (colloidal suspensions of magnetic particles).

The present invention also includes methods of making the compositions of the present invention. The methods of making the compositions include, but are not limited to, electroprocessing collagen, and optionally electroprocessing other materials, substances or both. One or more electroprocessing techniques, such as electrospin, electrospray, electroaerosol, electrosputter, or any combination thereof, can be employed to make the electroprocessed collagen materials and matrices of the present invention. In the most fundamental sense, the electroprocessing apparatus for electroprocessing material includes a electrodepositing mechanism and a target. In preferred embodiments, the electrodepositing mechanism includes one or more reservoirs to hold the one or more solutions that are to be electroprocessed or electrodeposited. The reservoir or reservoirs have at least one orifice, nozzle, or other means to allow the streaming of the solution from the reservoirs. The electroprocessing occurs due to the presence of a charge in either the orifices or the target, while the other is grounded. The substrate can also be used as a variable feature in the electroprocessing of materials used to make the electroprocessed composition. Specifically, the target can be the actual substrate for the materials used to make electroprocessed matrix, or electroprocessed matrix itself is deposited. Alternatively, a substrate can be disposed between the target and the nozzles. The target can also be specifically charged or grounded along a preselected pattern so that the solution streamed from the orifice is directed into specific directions. The electric field can be controlled by a microprocessor to create an electroprocessed matrix having a desired geometry. The target and the nozzle or nozzles can be engineered to be movable with respect to each other, thereby allowing additional control over the geometry of the electroprocessed matrix to be formed. The present invention allows forming matrices that have a predetermined shape.

The present method includes pre-selecting a mold adapted to make the predetermined shape and filling the mold with electroprocessed material or electrodepositing materials on the outer surface of the mold. Further shaping can be accomplished by manual processing of the formed matrices. For example, multiple formed matrices can be sutured, sealed, stapled, or otherwise attached to one another to form a desired shape. The electroprocessed matrix can be milled into a powder or milled and prepared as a hydrated gel composed of banded fibrils. Alternatively, the physical flexibility of many matrices allow them to be manually shaped to a desired structure. The electroprocessed collagen can be processed further, for example by crosslinking or shaping, or placement in a bioreactor for cell culturing. In this way, cells can be grown in an electroprocessed matrix.

The invention also includes numerous uses for the electroprocessed collagen compositions. The compositions of the present invention have a broad array of potential uses. Uses include, but are not limited to the following: manufacture of engineered tissue and organs, including structures such as patches, plugs or tissues of matrix material. These and other constructs can be supplemented with cells or used without cellular supplementation. Additional uses include the following: prosthetics, and other implants; tissue scaffolding, induction of differentiation of cells either in vitro or in vivo; repair or dressing of wounds; hemostatic devices; devices or structures for use in tissue repair and support such as sutures, adhesives, surgical and orthopedic screws, and surgical and orthopedic plates; natural coatings or components for synthetic implants; cosmetic implants and supports; repair or structural support for organs or tissues; substance delivery; bioengineering platforms; platforms for testing the effect of substances upon cells; cell culture; and numerous other uses.

Accordingly, it is an object of the present invention to overcome the foregoing limitations and drawbacks by providing compositions comprising electroprocessed collagen.

It is further an object of the present invention to provide compositions comprising electroprocessed collagen and other electroprocessed materials.

Another object of the present invention is to provide compositions comprising electroprocessed collagen and non-electroprocessed materials.

A further object of the present invention is to provide compositions comprising electroprocessed collagen and cells, molecules, objects, or combinations thereof.

Yet another object of the present invention is to provide the electroprocessed collagen compositions in a matrix.

It is further an object of the present invention to provide compositions comprising electroprocessed collagen matrices that resemble extracellular matrices in structure and composition.

A further object of the present invention is to provide methods for making compositions comprising electroprocessed collagen.

Another object of the present invention is to provide constructs comprising electroprocessed collagen matrices.

Yet another object of the present invention is to provide bioengineered tissue comprising the constructs of the present invention.

A further object of the present invention is to provide bioengineered organs comprising the constructs of the present invention.

Still another object of the present invention is to provide methods of making the constructs of the present invention.

It is further an object of the present invention to provide methods of making the constructs of the present invention.

Another object of the present invention is to provide methods of substance delivery.

A further object of the present invention is to provide methods of testing and study of cells and tissues in vitro.

It is further an object of the present invention to provide methods for cell and tissue culture.

It is another object of the present invention to provide bioengineering platforms comprising the compositions of the present invention.

A further object of the present invention is to provide compositions and methods useful in inducing cell differentiation.

A further object of the present invention is to provide matrices of collagen fibers having desired pore sizes.

A further object of the present invention is to provide matrices of collagen fibers having fiber diameters characteristic of natural collagen fibers.

A further object of the present invention is to provide matrices containing collagen fibers having desired fiber diameters.

A further object of the present invention is to provide matrices containing collagen fibers having desired moduli of elasticity when wet.

A further object of the present invention is to provide matrices containing collagen fibers having fiber diameters similar to those found in natural extracellular matrices.

These and other objects, features and advantages of the present invention will become apparent after a review of the following detailed description of the disclosed embodiments and the appended drawings.

DETAILED DESCRIPTION OF THE PREFERRED EMBODIMENTS

Definitions

Figure 1:
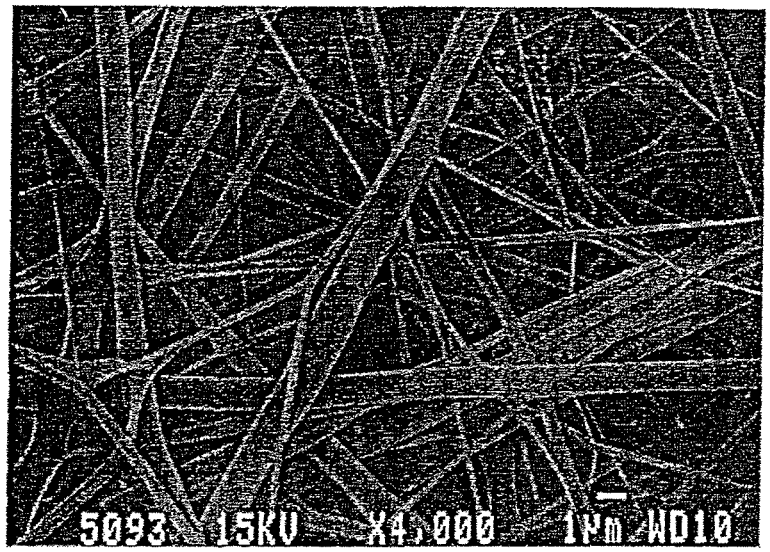
FIG. 1. SEM micrograph of 80:20 type I/elastin (size bar=1 um, magnification 4,000×).

The terms "electroprocessing" and "electrodeposition" shall be defined broadly to include all methods of electrospinning, electrospraying, electroaerosoling, and electrosputtering of materials, combinations of two or more such methods, and any other method wherein materials are streamed, sprayed, sputtered or dripped across an electric field and toward a target. The electroprocessed material can be electroprocessed from one or more grounded reservoirs in the direction of a charged substrate or from charged reservoirs toward a grounded target. "Electrospinning" means a process in which fibers are formed from a solution or melt by streaming an electrically charged solution or melt through an orifice. "Electroaerosoling" means a process in which droplets are formed from a solution or melt by streaming an electrically charged polymer solution or melt through an orifice. The term electroprocessing is not limited to the specific examples set forth herein, and it includes any means of using an electrical field for depositing a material on a target.

The term "material" refers to any compound, molecule, substance, or group or combination thereof that forms any type of structure or group of structures during or after electroprocessing. Materials include natural materials, synthetic materials, or combinations thereof. Naturally occurring organic materials include any substances naturally found in the body of plants or other organisms, regardless of whether those materials have or can be produced or altered synthetically. Synthetic materials include any materials prepared through any method of artificial synthesis, processing, or manufacture. Preferably the materials are biologically compatible materials.

One preferred class of materials for electroprocessing to make the compositions of the present invention comprises proteins. Extracellular matrix proteins are a preferred class of proteins in the present invention. Examples include but are not limited to collagen, fibrin, elastin, laminin, and fibronectin. An especially preferred group of proteins in the present invention is collagen of any type. Additional preferred materials are other components of the extracellular matrix, for example proteoglycans. In each case, those names are used throughout the present application in their broadest definition and encompass the various isoforms that are commonly recognized to exist within the different families of proteins and other molecules. There are multiple types of each of these proteins and molecules that are naturally-occurring, as well as types that can be or are synthetically manufactured or produced by genetic engineering. For example, collagen occurs in many forms and types and all of these types and subsets are encompassed herein.

The term protein, and any term used to define a specific protein or class of proteins further includes, but is not limited to, fragments, analogs, conservative amino acid substitutions, non-conservative amino acid substitutions and substitutions with non-naturally occurring amino acids with respect to a protein or type or class of proteins. Thus, for example, the term collagen includes, but is not limited to, fragments, analogs, conservative amino acid substitutions, and substitutions with non-naturally occurring amino acids or residues with respect to any type or class of collagen. The term "residue" is used herein to refer to an amino acid (D or L) or an amino acid mimetic that is incorporated into a protein by an amide bond. As such, the residue can be a naturally occurring amino acid or, unless otherwise limited, can encompass known analogs of natural amino acids that function in a manner similar to the naturally occurring amino acids (i.e., amino acid mimetics). Moreover, an amide bond mimetic includes peptide backbone modifications well known to those skilled in the art.

Furthermore, one of skill in the art will recognize that, as mentioned above, individual substitutions, deletions or additions which alter, add or delete a single amino acid or a small percentage of amino acids (preferably less than 10%, more preferably less than 5%) in an encoded sequence are conservatively modified variations where the alterations result in the substitution of an amino acid with a chemically similar amino acid. Conservative substitution tables providing functionally similar amino acids are well known in the art. The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

It is to be understood that the term protein, polypeptide or peptide further includes fragments that may be 90 to 95% of the entire amino acid sequence, and also extensions to the entire amino acid sequence that are 5% to 10% longer than the amino acid sequence of the protein, polypeptide or peptide.

When peptides are relatively short in length (i.e., less than about 50 amino acids), they are often synthesized using standard chemical peptide synthesis techniques. Solid phase synthesis in which the C terminal amino acid of the sequence is attached to an insoluble support followed by sequential addition of the remaining amino acids in the sequence is a preferred method for the chemical synthesis of the antigenic epitopes described herein. Techniques for solid phase synthesis are known to those skilled in the art.

Alternatively, the proteins or peptides that may be electroprocessed are synthesized using recombinant nucleic acid methodology. Generally, this involves creating a nucleic acid sequence that encodes the peptide or protein, placing the nucleic acid in an expression cassette under the control of a particular promoter, expressing the peptide or protein in a host, isolating the expressed peptide or protein and, if required, renaturing the peptide or protein. Techniques sufficient to guide one of skill through such procedures are found in the literature.

When several desired protein fragments or peptides are encoded in the nucleotide sequence incorporated into a vector, one of skill in the art will appreciate that the protein fragments or peptides may be separated by a spacer molecule such as, for example, a peptide, consisting of one or more amino acids. Generally, the spacer will have no specific biological activity other than to join the desired protein fragments or peptides together, or to preserve some minimum distance or other spatial relationship between them. However, the constituent amino acids of the spacer may be selected to influence some property of the molecule such as the folding, net charge, or hydrophobicity. Nucleotide sequences encoding for the production of residues which may be useful in purification of the expressed recombinant protein may be built into the vector. Such sequences are known in the art. For example, a nucleotide sequence encoding for a poly histidine sequence may be added to a vector to facilitate purification of the expressed recombinant protein on a nickel column.

Once expressed, recombinant peptides, polypeptides and proteins can be purified according to standard procedures known to one of ordinary skill in the art, including ammonium sulfate precipitation, affinity columns, column chromatography, gel electrophoresis and the like. Substantially pure compositions of about 50 to 99% homogeneity are preferred, and 80 to 95% or greater homogeneity are most preferred for use as therapeutic agents.

Also, molecules capable of forming some of the named proteins can be mixed with other polymers during electroprocessing to obtain desired properties for uses of the formed protein in the matrix.

Another class of synthetic materials, preferably biologically compatible synthetic materials, comprises polymers. Such polymers include but are not limited to the following: poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), polylactides (PLA), polyglycolides (PGA), poly(lactide-co-glycolides) (PLGA), polyanhydrides, and polyorthoesters or any other similar synthetic polymers that may be developed that are biologically compatible. The term "biologically compatible, synthetic polymers" shall also include copolymers and blends, and any other combinations of the forgoing either together or with other polymers generally. The use of these polymers will depend on given applications and specifications required. A more detailed discussion of these polymers and types of polymers is set forth in Brannon-Peppas, Lisa, "Polymers in Controlled Drug Delivery," *Medical Plastics and Biomaterials*, November 1997, which is incorporated by reference as if set forth fully herein.

"Materials" also include electroprocessed materials that are capable of changing into different materials during or after electroprocessing. For example, procollagen will form collagen when combined with procollagen peptidase. Procollagen, procollagen peptidase, and collagen are all within the definition of materials. Similarly, the protein fibrinogen, when combined with thrombin, forms fibrin. Fibrinogen or thrombin that are electroprocessed as well as the fibrin that later forms are included within the definition of materials.

In a preferred embodiment, the electroprocessed materials form a matrix. The term "matrix" refers to any structure comprised of electroprocessed materials. Matrices are comprised of fibers, or droplets of materials, or blends of fibers and droplets of any size or shape. Matrices are single structures or groups of structures and can be formed through one or more electroprocessing methods using one or more materials. Matrices are engineered to possess specific porosities. Substances can be deposited within, or anchored to or placed on matrices. Cells are substances which can be deposited within or on matrices.

The term "substance" shall be used throughout this application in its broadest definition. The term substance includes one or more molecules, objects, or cells of any type or size, or combinations thereof. Substances can be in any form including, but not limited to solid, semisolid, wet or dry mixture, gas, solution, suspension, combinations thereof. Substances include molecules of any size and in any combination. Cells include all types of prokaryotic and eukaryotic cells, whether in natural state, or altered by genetic engineering or any other process. Cells can be from a natural source or cultured in vitro and can be living or dead. Combinations of different types of cells can be used. Objects can be of any size, shape, and composition that may be combined with or coupled to an electroprocessed material. Examples of objects include, but are not limited to, cell fragments, cell debris, fragments of cell walls, extracellular matrix constituents, fragments of viral walls, organelles and other cell components, tablets, viruses, vesicles, liposomes, capsules, nanoparticulates, and other structures that serve as an enclosure for molecules. The compositions of the present invention may comprise one substance or any combination of substances.

Throughout this application the term "solution" is used to describe the liquid in the reservoirs of the electroprocessing method. The term is defined broadly to include any liquids that contain materials to be electroprocessed. It is to be understood that any solutions capable of forming a material during electroprocessing are included within the scope of the present invention. In this application, the term "solution" also refers to suspensions or emulsions containing the material or anything to be electrodeposited. "Solutions" can be in organic or biologically compatible forms. This broad definition is appropriate in view of the large number of solvents or other liquids and carrier molecules, such as poly(ethylene oxide) (PEO), that can be used in the many variations of electroprocessing. In this application, the term "solution" also refers to melts, hydrated gels and suspensions containing the materials, substances or anything to be electrodeposited.

Throughout this application, the term "processing aid" denotes any substance that is added to a solution wherein the substance confers the ability to create, to remove, or to otherwise influence one or more properties of: a solution from which materials are electroprocessed; an electroprocessing process; an electroprocessed material resulting from an electroprocessing process; or a combination of any of the foregoing. Examples of such properties include, but are not limited to: the morphology of the materials after electroprocessing (including, for example, whether the electroprocessed materials form fibers, droplets, hollow fibers, or other shapes and whether the resulting shapes have specific morphologies such as "beads on a string" fiber morphology); the ability to suspend, disperse, or dissolve a material that is to be electroprocessed within a solution; the ability to form an emulsion, suspension, or dispersion having two or more phases in a solution; the existence within electroprocessed materials of individual objects, bodies, or structures of the electroprocessed material (e.g. fibers, fibrils, films, sprays, particles, or droplets) possessing internal cavities, pockets, enclosures or other inclusions, and combinations thereof; and desirable mechanical properties of an electroprocessed material such as flexibility or strength. Any processing aid that influences a property or confers a desired property may be used. In some embodiments, the processing aids include surfactants. Examples of surfactants that can be used include, for example, any ionic or non-ionic surfactants known to one of ordinary skill in the art. Specific examples include, but are not limited to, the natural surfactant constituents of the lung (for example, a total extract of the material produced by the alveolar epithelial type II cells containing 80% phospholipids, 10% proteins and 10% neutral lipids or specific components of mixture such as phosphatidylcholine, phosphatidylglycerol, sphingomyelin and/or the surfactant proteins SP-A, SP-B, SP-C and SP-D), bovine serum albumin, fatty acid salts (e.g., sodium lauryl sulfate), TWEEN, and non-ionic substances such as TRITON (oligoethylene oxide-modified phenols) or PLURONICS (ethylene oxide-propylene oxide-ethylene oxide block copolymers). Typical ionic or non-ionic surfactants are known to one of ordinary skill in the art and are commercially available from SIGMA (St. Louis, Mo.) or ALDRICH (Milwaukee, Wis.). In other embodiments, processing aids contain plasticizers. Examples of plasticizers include, but are not limited to, glycerol and polyethylene glycols.

Throughout this application, the term "isolated" in reference to collagen or any other material or substance refers to the material or substance having been: derived by using techniques to process a natural source of the material or substance (for example, by purifying or otherwise separating the substance or material from other constituents of the natural source); manufactured synthetically; produced recombinantly or otherwise through genetic engineering; produced through any other manufacturing or processing means; or any combination of the foregoing.

Solvents

Any solvent can be used that allows delivery of the material or substance to the orifice, tip of a syringe, or other site from which the material will be electroprocessed. The solvent may be used for dissolving or suspending the material or the substance to be electroprocessed. Solvents useful for dissolving or suspending a material or a substance depend on the material or substance. Electrospinning techniques often require more specific solvent conditions. For example, collagen can be electrodeposited as a solution or suspension in water, 2,2,2-trifluoroethanol, 1,1,1,3,3,3-hexafluoro-2-propanol (also known as hexafluoroisopropanol or HFIP), or combinations thereof. Fibrin monomer can be electrodeposited or electrospun from solvents such as urea, monochloroacetic acid, water, 2,2,2-trifluoroethanol, HFIP, or combinations thereof. Elastin can be electrodeposited as a solution or suspension in water, 2,2,2-trifluoroethanol, isopropanol, HFIP, or combinations thereof, such as isopropanol and water. In one desirable embodiment, elastin is electrospun from a solution of 70% isopropanol and 30% water containing 250 mg/ml of elastin. Other lower order alcohols, especially halogenated alcohols, may be used. Other solvents that may be used or combined with other solvents in electroprocessing natural matrix materials include acetamide, N-methylformamide, N,N-dimethylformamide (DMF), dimethylsulfoxide (DMSO), dimethylacetamide, N-methylpyrrolidone (NMP), acetic acid, trifluoroacetic acid, ethyl acetate, acetonitrile, trifluoroacetic anhydride, 1,1,1-trifluoroacetone, maleic acid, hexafluoroacetone.

Proteins and peptides associated with membranes are often hydrophobic and thus do not dissolve readily in aqueous solutions. Such proteins can be dissolved in organic solvents such as methanol, chloroform, and trifluoroethanol (TFE) and emulsifying agents. Any other solvents known to one of skill in the protein chemical art may be used, for example solvents useful in chromatography, especially high performance liquid chromatography. Proteins and peptides are also soluble, for example, in HFIP, hexafluoroacetone, chloroalcohols in conjugation with aqueous solutions of mineral acids, dimethylacetamide containing 5% lithium chloride, and in acids such as acetic acid, hydrochloric acid and formic acid. In some embodiments, the acids are very dilute, in others the acids are concentrated. N-methyl morpholine-N-oxide is another solvent that can be used with many polypeptides. Other examples, used either alone or in combination with organic acids or salts, include the following: triethanolamine; dichloromethane; methylene chloride; 1,4-dioxane; acetonitrile; ethylene glycol; diethylene glycol; ethyl acetate; glycerine; propane-1,3-diol; furan; tetrahydrofuran; indole; piperazine; pyrrole; pyrrolidone; 2-pyrrolidone; pyridine; quinoline; tetrahydroquinoline; pyrazole; and imidazole. Combinations of solvents may also be used.

Synthetic polymers may be electrodeposited from, for example, HFIP, methylene chloride, ethyl acetate; acetone, 2-butanone (methyl ethyl ketone), diethyl ether; ethanol; cyclohexane; water; dichloromethane (methylene chloride); tetrahydrofuran; dimethylsulfoxide (DMSO); acetonitrile; methyl formate and various solvent mixtures. HFIP and methylene chloride are desirable solvents. Selection of a solvent will depend upon the characteristics of the synthetic polymer to be electrodeposited.

Selection of a solvent is based in part on consideration of secondary forces that stabilize polymer-polymer interactions and the solvent's ability to replace these with strong polymer-solvent interactions. In the case of polypeptides such as collagen, and in the absence of covalent crosslinking, the principal secondary forces between chains are: (1) coulombic, resulting from attraction of fixed charges on the backbone and dictated by the primary structure (e.g., lysine and arginine residues will be positively charged at physiological pH, while aspartic or glutamic acid residues will be negatively charged); (2) dipole-dipole, resulting from interactions of permanent dipoles; the hydrogen bond, commonly found in polypeptides, is the strongest of such interactions; and (3) hydrophobic interactions, resulting from association of non-polar regions of the polypeptide due to a low tendency of non-polar species to interact favorably with polar water molecules. Therefore, solvents or solvent combinations that can favorably compete for these interactions can dissolve or disperse polypeptides. For example, HFIP and TFE possess a highly polar OH bond adjacent to a very hydrophobic fluorinated region. While not wanting to be bound by the following theories, it is believed that the alcohol portion can hydrogen bond with peptides, and can also solvate charges on the backbone, thus reducing Coulombic interactions between molecules. Additionally, the hydrophobic portions of these solvents can interact with hydrophobic domains in polypeptides, helping to resist the tendency of the latter to aggregate via hydrophobic interactions. It is further believed that solvents such as HFIP and TFE, due to their lower overall polarities compared to water, do not compete well for intramolecular hydrogen bonds that stabilize secondary structures such as an alpha helix. Consequently, alpha helices in these solvents are believed to be stabilized by virtue of stronger intramolecular hydrogen bonds. The stabilization of polypeptide secondary structures in these solvents is believed desirable, especially in the cases of collagen and elastin, to preserve the proper formation of collagen fibrils during electroprocessing. In some embodiments, solvents are selected based on their tendency to induce helical structure in electrospun protein fibers, thereby predisposing monomers of collagen or other proteins to undergo polymerization and form helical polymers that mimic the native collagen fibril. Examples of such solvents include halogenated alcohols, preferably fluorinated alcohols (HFIP and TFE) hexafluoroacetone, chloroalcohols in conjugation with aqueous solutions of mineral acids and dimethylacetamide, preferably containing lithium chloride. HFIP and TFE are especially preferred. In some embodiments, water is added to the solvents.

Additionally, it is often desirable, although not necessary, for the solvent to have a relatively high vapor pressure to promote the stabilization of an electrospinning jet to create a fiber as the solvent evaporates. A relatively volatile solvent is also desirable for electrospraying to minimize coalescence of droplets during and after spraying and formation of dry electroprocessed materials. In embodiments involving higher boiling point solvents, it is often desirable to facilitate solvent evaporation by warming the spinning or spraying solution, and optionally the electroprocessing stream itself, or by electroprocessing in reduced atmospheric pressure. It is also believed that creation of a stable jet resulting in a fiber is facilitated by a low surface tension of the polymer/solvent mixture. Solvent choice can also be guided by this consideration.

In functional terms, solvents used for electroprocessing have the principal role of creating a mixture with collagen and/or other materials to be electroprocessed, such that electroprocessing is feasible. The concentration of a given solvent is often an important consideration in determining the type of electroprocessing that will occur. For example, in electrospraying, the solvent should assist in the dispersion of droplets of electroprocessed material so that the initial jet of liquid disintegrates into droplets. Accordingly, solvents used in electrospraying should not create forces that will stabilize an unconfined liquid column. In electrospinning, interactions between molecules of electroprocessed material stabilize the jet, leading to fiber formation. For electrospun embodiments, the solvent should sufficiently dissolve or disperse the polymer to prevent the jet from disintegrating into droplets and should thereby allow formation of a stable jet in the form of a fiber. In some embodiments, the transition from electrospraying to electrospinning can be determined by examining viscosity measurements (using a Brookfield viscometer) for polymer solutions as a function of concentration. Viscosity increases as concentration of a polymer or other material to be electroprocessed increases. Above a critical concentration associated with extensive chain entanglements of materials, however, the viscosity will increase more rapidly with concentration, as opposed to a more gradual, linear rise with concentration at lower concentrations. Departures from linearity approximately coincide with the transition from electrospraying to electrospinning.

The solubility of any electroprocessed material in a solvent may be enhanced by modifying the material. Any method for modifying materials to increase their solubility may be used. For example, U.S. Pat. No. 4,164,559 to Miyata et al. discloses a method for chemically modifying collagen to increase solubility.

Compositions of the Present Invention

Electroprocessed Collagen

The compositions of the present invention comprise electroprocessed collagen. The invention includes collagen electroprocessed by any means. The electroprocessed collagen may constitute or be formed from any collagen within the full meaning of the term as set forth above in the definition of "protein." As such, it may include collagen fragments, analogs, conservative amino acid substitutions, non-conservative amino acid substitutions, and substitutions with non-naturally occurring amino acids or residues with respect to any type or class of collagen. The collagen used in electroprocessing may be derived from a natural source, manufactured synthetically, produced through genetic engineering, or produced through any other means or combinations thereof. Natural sources include, but are not limited to, collagens produced by or contained within the tissue of living organisms. For example, electroprocessed collagen to be implanted in a matrix can include, but is not limited to, autologous collagen, collagen from a conspecific organism, or collagen from another species. Some collagens that can be used include but are not limited to collagen types I, II, III, IV, V, VI, VII, VIII, IX, X, XI, XII, XIII, XIV, XV, XVI, XVII, XVIII, and XIX. Some preferred collagens include types I and III. Synthetic collagen can include that produced by any artificial means. Numerous methods for producing collagens and other proteins are known in the art. Synthetic collagen can be prepared using specific sequences. For example, genetically engineered collagen can be prepared with specific desired sequences of amino acids that differ from natural collagen. Engineered collagen may be produced by any means, including, for example, peptide, polypeptide, or protein synthesis. For example, cells can be genetically engineered in vivo or in vitro to produce collagen or molecules capable of forming collagen, or subdomains of collagen, and the desired collagen can be harvested. In one illustrative embodiment, desirable sequences that form binding sites on collagen protein for cells or peptides can be included in higher amounts than found in natural collagen. The electroprocessed collagen may also be formed from collagen itself or any other material that forms a collagen structure when electroprocessing. Examples include, but are not limited to, amino acids, peptides, denatured collagen such as gelatin, polypeptides, and proteins. Collagen can be formed either before, during, or after electroprocessing. For example, electroprocessed collagen formed by combining procollagen with procollagen peptidase either before, during, or after electroprocessing is within the invention.

The electroprocessed collagen may be made using any electroprocessing technique, including, but not limited to, electrospinning, electroaerosol, electrospraying or electrosputtering techniques, or any combination thereof. Accordingly, electroprocessed droplets, particles, fibers, fibrils, or combinations thereof are all included in the electroprocessed collagen compositions of the present invention. In one desirable embodiment, collagen is electrospun to form collagen fibers. In some embodiments, electrospun collagen has a repeating, banded pattern when it is examined by electron microscopy. Any type of banding patterns can be used, and the invention is not limited to one or more specific banding pattern, but rather includes any feasible banding pattern as well as embodiments with no pattern at all. In some desirable embodiments, the banded pattern is typical of or similar to collagen fibrils produced by cells in an extracellular matrix. Examples include but are not limited to: embodiments involving collagen types I, II, and/or III in which, the pattern has spacing of about 65-67 nm; embodiments in which the banding pattern of collagen types I, II, and/or III is about 67 nm. While not wanting to be bound by the following statement, the banded pattern characteristic of some electrospun collagens is believed be an important attribute because it is believed in some embodiments to promote or regulate biological activities. This regulation can operate through any type of mechanism associated with the electrospun collagen. In other embodiments, including some embodiments involving electrospun denatured collagen from gelatin, the characteristic banding patterns are absent. In some embodiments, denatured collagen is electrospun into fiber structures that lack the banding patterns.

Several desirable sequences can be incorporated into synthetic collagen. Any sequence that can be incorporated into a collagen molecule may be used. For example, the P-15 site, a 15 amino acid sequence within some collagen molecules, promotes osteoblasts to produce and to secrete hydroxyapatite, a component of bone. Another example of specific sites and sequences within collagen molecules that can be manipulated and processed in a similar fashion includes the RGD binding sites characteristic of the integrin molecule. The RGD site is a sequence of three amino acids (Arg-Gly-Asp) present in many extracellular matrix materials that serves as a binding site for cell adhesion. It is recognized and bound, for example, by integrins. In addition, electroprocessed collagen can be enriched with specific desired sequences before, during, or after electroprocessing. Sequences can be added in linear or other forms. In some embodiments, the RGD sequences are arranged in a cyclic form referred to as cyclo-RGD.

In some embodiments, implanted electroprocessed collagen, especially electrospun collagen, does not trigger an immune or inflammatory response from the host, a response that which may occur with the use of some synthetic materials that release hydrolytic by-products that can alter the local pH. Furthermore, in some embodiments, implanted electroprocessed collagen undergoes normal matrix remodeling after implantation. In one embodiment, a scaffolding of electrospun collagen was substantially remodeled after eight weeks in vivo.

Other Electroprocessed Materials

In some embodiments, the electroprocessed collagen compositions include additional electroprocessed materials. As defined above, other electroprocessed materials can include natural materials, synthetic materials, or combinations thereof. Examples include, but are not limited to, amino acids, peptides, denatured peptides such as gelatin from denatured collagen, polypeptides, proteins, carbohydrates, lipids, nucleic acids, glycoproteins, minerals, lipoproteins, glycolipids, glycosaminoglycans, and proteoglycans.

Figure 2:
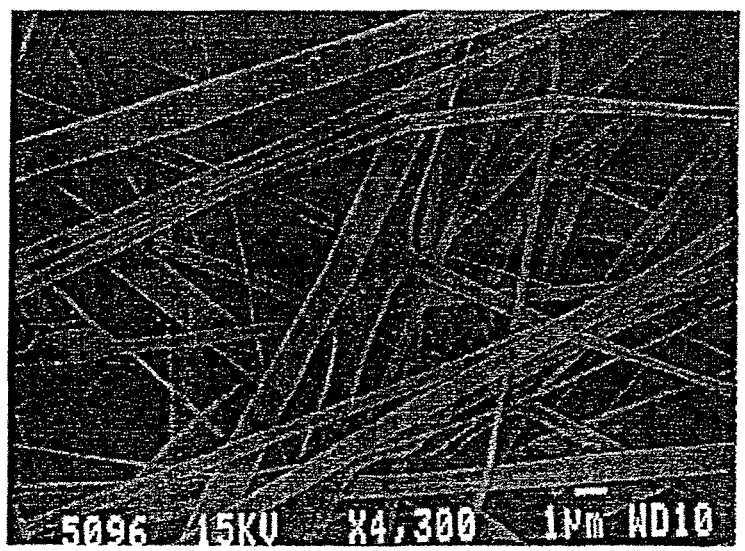
FIG. 2. SEM micrograph of electrospun 45:35:20 type I/III/elastin matrices (size bar=1 um, magnification 4,300×).

Some preferred materials for electroprocessing with collagen are naturally occurring extracellular matrix materials and blends of naturally occurring extracellular matrix materials, including, but not limited to, fibrin, elastin, laminin, fibronectin, chitin, chitosan, alginates hyaluronic acid, chondroitin 4-sulfate, chondroitin 6-sulfate, dermatan sulfate, heparan sulfate, heparin, and keratan sulfate, and proteoglycans. These materials may be manufactured or isolated by any means include isolation from humans or other animals or cells or synthetically manufactured. Some especially preferred natural matrix materials to combine with electroprocessed collagen are fibrin, elastin, and fibronectin. For example, FIG. 1 is a scanning electron micrograph of an electrospun matrix of type I collagen/elastin (80:20). FIG. 2 is a scanning electron micrograph of an electrospun matrix of type I collagen/type III collagen/elastin (55:35:20). Examples of preferred electroprocessed compositions include, but are not limited to: embodiments in which the material is electroprocessed from a solution containing pure or substantially pure Type I collagen; embodiments in which the material is electroprocessed from a solution containing another type of collagen in a pure or substantially pure form (e.g. substantially pure Type II collagen, substantially pure Type III collagen, etc.); embodiments in which the material is electroprocessed from a solution containing more than one type of collagen in varying amounts (e.g. blends of Type I and Type III collagen, blends of Type I and Type II collagen, etc.); and embodiments in which the material is electroprocessed from a solution containing one or more type of collagen along with other natural or synthetic materials or both (e.g. blends of Type I collagen/Type III collagen/elastin in a ratio of approximately 45:35:20; blends of Type I collagen/Type III collagen/elastin in a ratio of approximately 40:40:20; blends of Type I collagen and elastin in a ratio of approximately 80:20; blends of Type I collagen/PGA/PLA in a ratio of approximately 80:10:10, blends of Type I collagen and a PGA/PLA copolymer in a ratio of approximately 80:20.) In some embodiments, the electroprocessed material includes crude extracts of tissue, extracellular matrix material, extracts of non-natural tissue, or extracellular matrix materials alone or in combination. Extracts of biological materials, including, but not limited to, cells, tissues, organs, and tumors may also be electroprocessed.

It is to be understood that these electroprocessed materials may be combined with other materials and/or substances in forming the compositions of the present invention. For example, an electroprocessed peptide may be combined with an adjuvant to enhance immunogenicity when implanted subcutaneously. As another example, an electroprocessed collagen matrix, containing cells, may be combined with an electroprocessed biologically compatible polymer and growth factors to stimulate growth and division of the cells in the collagen matrix.

Synthetic electroprocessed materials include any materials prepared through any method of artificial synthesis, processing, or manufacture. The synthetic materials are preferably biologically compatible for administration in vivo or in vivo. Such polymers include but are not limited to poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), synthetic polycations (such as poly(ethylene imine)), synthetic polyanions (such as poly(styrene sulfonate) and poly(methacrylic acid)), poly(methacrylic acid), polylactic acid (PLA), polyglycolic acids (PGA), poly(lactide-co-glycolides) (PLGA), nylons, polyamides, polyanhydrides, poly(ethylene-co-vinyl alcohol) (EVOH), polycaprolactone, poly(vinyl acetate) (PVA), poly(ethylene oxide) (PEO) and polyorthoesters or any other similar synthetic polymers that may be developed that are biologically compatible. Some preferred synthetic matrix materials include PLA, PGA, copolymers of PLA and PGA, polycaprolactone, poly(ethylene-co-vinyl acetate), EVOH, PVA, and PEO. Matrices can be formed of electrospun fibers, electroaerosol, electrosprayed, or electrosputtered droplets, or a combination of the foregoing.

In embodiments in which natural materials are used, those materials can be derived from a natural source, synthetically manufactured, or manufactured by genetically engineered cells. For example, genetically engineered proteins can be prepared with specific desired sequences of amino acids that differ from the natural proteins.

By selecting different materials for combining with electroprocessed collagen, or combinations thereof, many characteristics of the electroprocessed material can be manipulated. The properties of a matrix comprised of electroprocessed collagen may be adjusted. Electroprocessed collagen and other electroprocessed materials can provide a therapeutic effect when applied. In addition, selection of matrix materials can affect the permanency of an implanted matrix. For example, matrices made of fibrin will degrade more rapidly while matrices made of collagen are more durable and synthetic matrix materials are more durable still. Use of matrices made of natural materials such as proteins also minimize rejection or immunological response to an implanted matrix. Accordingly, selection of materials for electroprocessing and use in substance delivery is influenced by the desired use. In one embodiment, a skin patch of electroprocessed fibrin or collagen combined with healing promoters, analgesics and or anesthetics and anti-rejection substances may be applied to the skin and may subsequently dissolve into the skin. In another embodiment, an electroprocessed collagen implant for delivery to bone may be constructed of materials useful for promoting bone growth, osteoblasts and hydroxyapatite, and may be designed to endure for a prolonged period of time. In embodiments in which the matrix contains substances that are to be released from the matrix, incorporating electroprocessed synthetic components, such as biocompatible substances, can modulate the release of substances from an electroprocessed composition. For example, layered or laminate structures can be used to control the substance release profile. Unlayered structures can also be used, in which case the release is controlled by the relative stability of each component of the construct. For example, layered structures composed of alternating electroprocessed materials are prepared by sequentially electroprocessing different materials onto a target. The outer layers are, for example, tailored to dissolve faster or slower than the inner layers. Multiple agents can be delivered by this method, optionally at different release rates. Layers can be tailored to provide a complex, multi-kinetic release profile of a single agent over time. Using combinations of the foregoing provides for release of multiple substances released, each with a complex profile.

In some embodiments, electroprocessed materials are used to form seamless and complex, three-dimensional shapes by depositing fibrils of electrospun collagen along a defined axis to control the alignment and distribution of cells within a bioengineered organ.

Layering of structures is used in some embodiments to mimic more closely the composition of natural materials. For example, manipulating the amounts of Type I collagen, Type II collagen, and elastin in successive layers is used in some embodiments to mimic gradients or other patterns of distribution across the depth of a structure such as the wall of a blood vessel. Other embodiments accomplish such patterns without layering. For example, altering the feed rates of Type I collagen, Type II collagen and elastin into an electroprocessing apparatus during an electroprocessing run allows for creation of continuous gradients and patterns without layering.

Synthetic materials can be electroprocessed from different solvents. This can be important for the delivery of some materials. In some embodiments, a drug that is be insoluble in the solvents used to electroprocess collagen will be soluble in a solvent used to electroprocess synthetic materials. In such embodiments, using synthetics increases the number of materials that can be combined with the electroprocessed collagen matrix. Polymers may be derivatized in a way to provide such sensitivity. These properties provide flexibility in making and using electroprocessed materials designed to deliver various substances, in vivo and in vitro.

An electroprocessed collagen composition, such as a matrix, can also be composed of specific subdomains of a matrix constituent and can be prepared with a synthetic backbone that can be derivatized. For example, the RGD peptide sequence, and/or a heparin binding domain and/or other sequences, can be chemically coupled to synthetic materials. The synthetic polymer with the attached sequence or sequences can be electroprocessed with the collagen into a construct. This produces a matrix with unique properties. In these examples the RGD site provides a site for cells to bind and interact with the synthetic components of the matrix. The heparin-binding site can be engineered and used as a site for the attachment of peptide growth factors to the synthetic backbone. Angiogenic peptides, genetic material, growth factors, cytokines, enzymes and drugs are other non-limiting examples of substances that can be attached to the backbone of an electroprocessed material to provide functionality. Binding can be direct or indirect (that is, through an intermediate molecule or moiety). Another embodiment of matrix materials that have a therapeutic effect is electroprocessed fibrin. Fibrin matrix material assists in arrest of bleeding. Peptide side chains may also be used to attach molecules to functional groups on polymeric backbones. Molecules and other substances can be attached to a material to be electroprocessed by any technique known in the art.

Substances Combined with Electroprocessed Collagen Compositions

In many desirable embodiments, the electroprocessed collagen is combined with one or more substances. As discussed above, the word "substance" in the present invention is used in its broadest definition. In embodiments in which the electroprocessed collagen compositions of the present invention comprise one or more substances, substances can include any type or size of molecules, cells, objects or combinations thereof. The compositions of the present invention may comprise one substance or any combination of substances.

A desirable embodiment includes cells as a substance combined with the electroprocessed collagen matrix. Any cell can be used. Some preferred examples include, but are not limited to, stem cells, committed stem cells, and differentiated cells. Examples of stem cells include, but are not limited to, embryonic stem cells, bone marrow stem cells and umbilical cord stem cells. Other examples of cells used in various embodiments include, but are not limited to, osteoblasts, myoblasts, neuroblasts, fibroblasts, glioblasts, germ cells, hepatocytes, chondrocytes, keratinocytes, smooth muscle cells, cardiac muscle cells, connective tissue cells, glial cells, epithelial cells, endothelial cells, hormone-secreting cells, cells of the immune system, and neurons. In some embodiments it is unnecessary to pre-select the type of stem cell that is to be used, because many types of stem cells can be induced to differentiate in an organ specific pattern once delivered to a given organ. For example, a stem cell delivered to the liver can be induced to become a liver cell simply by placing the stem cell within the liver. Cells in the matrix can serve the purpose of providing scaffolding or seeding, producing certain compounds, or both.

Embodiments in which the substance comprises cells include cells that can be cultured in vitro, derived from a natural source, genetically engineered, or produced by any other means. Any natural source of prokaryotic or eukaryotic cells may be used. Embodiments in which the matrix is implanted in an organism can use cells from the recipient, cells from a conspecific donor or a donor from a different species, or bacteria or microbial cells. Cells harvested from a source and cultured prior to use are included.

Some embodiments use cells that have been genetically engineered. The engineering involves programming the cell to express one or more genes, repressing the expression of one or more genes, or both. One example of genetically engineered cells useful in the present invention is a genetically engineered cell that makes and secretes one or more desired molecules. When electroprocessed collagen matrices comprising genetically engineered cells are implanted in an organism, the molecules produced can produce a local effect or a systemic effect, and can include the molecules identified above as possible substances. Cells can also produce antigenic materials in embodiments in which one of the purposes of the matrix is to produce an immune response. Cells may produce substances to aid in the following non-inclusive list of purposes inhibit or stimulate inflammation; facilitate healing; resist immunorejection; provide hormone replacement; replace neurotransmitters; inhibit or destroy cancer cells; promote cell growth; inhibit or stimulate formation of blood vessels; augment tissue; and to supplement or replace neurons, skin, synovial fluid, tendons, cartilage (including, but not limited to articular cartilage), ligaments, bone, muscle, organs, dura, blood vessels, bone marrow, and extracellular matrix.

Some embodiments use cells that are abnormal in some way. Examples include cells that have been genetically engineered, transformed cells, and immortalized cells. Genetic engineering involves programming the cell to express one or more genes (including, but not limited to genes transfected into the cell), repress the expression of one or more genes, or both. One example of genetically engineered cells useful in the present invention is genetically engineered cells that make and secrete one or more desired molecules. In some embodiments, when genetically engineered cells are implanted in an organism, the molecules produced cause a local effect or systemic effect. Examples of molecules produced include all molecules identified above as "substances." In some embodiments, cells produce antigenic materials, allowing the electroprocessed material to cause an immune response. Examples of genetically engineered cells used in the present invention include cells that inhibit or stimulate inflammation; facilitate healing; resist immunorejection; provide hormone replacement; replace neurotransmitters; inhibit or destroy cancer cells; promote cell growth; inhibit or stimulate formation of blood vessels; augment tissue; and/or supplement or replace neurons, skin, synovial fluid, tendons, cartilage, ligaments, bone, muscle, organs, dura, blood vessels, bone marrow, and extracellular matrix.

Genetic engineering can involve, for example, adding or removing genetic material to or from a cell, altering existing genetic material, or both. Embodiments in which cells are transfected or otherwise engineered to express a gene can use transiently or permanently transfected genes, or both. Gene sequences may be full or partial length, cloned or naturally occurring.

In many embodiments, cells in an electrospun matrix exhibit characteristics and functions typical of such cells in vivo. Examples include, but are not limited to: osteoblasts on a Type I collagen matrix that differentiate and produce hydroxyapatite; muscle cells in a collagen matrix that arrange into muscle fibers, chondrocytes in a Type II collagen matrix causing formation in the matrix of lacunae of the type characteristic of cartilage in vivo; and immortalized chondrocytes in a matrix of fibrinogen and/or Type II collagen matrix forming cell clusters characteristic of immortalized chondrocytes in vivo. Embodiments in which cells exhibit either normal, abnormal, or a combination of normal and abnormal characteristics are included within the present invention.

In embodiments in which the substances are molecules, any molecule can be used. Molecules may, for example, be organic or inorganic and may be in a solid, semisolid, liquid, or gas phase. Molecules may be present in combinations or mixtures with other molecules, and may be in solution, suspension, or any other form. Examples of classes of molecules that may be used include human or veterinary therapeutics, cosmetics, nutraceuticals, agriculturals such as herbicides, pesticides and fertilizers, vitamins, salts, electrolytes, amino acids, peptides, polypeptides, proteins, carbohydrates, lipids, nucleic acids, glycoproteins, lipoproteins, glycolipids, glycosaminoglycans, proteoglycans, growth factors, hormones, neurotransmitters, pheromones, chalones, prostaglandins, immunoglobulins, monokines and other cytokines, humectants, metals, gases, minerals, plasticizers, ions, electrically and magnetically reactive materials, light sensitive materials, anti-oxidants, molecules that may be metabolized as a source of cellular energy, antigens, and any molecules that can cause a cellular or physiological response. Any combination of molecules can be used, as well as agonists or antagonists of these molecules.

Several preferred embodiments include use of any therapeutic molecule including, without limitation, any pharmaceutical or drug. Examples of pharmaceuticals include, but are not limited to, anesthetics, hypnotics, sedatives and sleep inducers, antipsychotics, antidepressants, antiallergics, antianginals, antiarthritics, antiasthmatics, antidiabetics, antidiarrheal drugs, anticonvulsants, antigout drugs, antihistamines, antipruritics, emetics, antiemetics, antispasmodics, appetite suppressants, neuroactive substances, neurotransmitter agonists, antagonists, receptor blockers and reuptake modulators, beta-adrenergic blockers, calcium channel blockers, disulfuram and disulfuram-like drugs, muscle relaxants, analgesics, antipyretics, stimulants, anticholinesterase agents, parasympathomimetic agents, hormones, anticoagulants, antithrombotics, thrombolytics, immunoglobulins, immunosuppressants, hormone agonists/antagonists, vitamins, antimicrobial agents, antineoplastics, antacids, digestants, laxatives, cathartics, antiseptics, diuretics, disinfectants, fungicides, ectoparasiticides, antiparasitics, heavy metals, heavy metal antagonists, chelating agents, gases and vapors, alkaloids, salts, ions, autacoids, digitalis, cardiac glycosides, antiarrhythmics, antihypertensives, vasodilators, vasoconstrictors, antimuscarinics, ganglionic stimulating agents, ganglionic blocking agents, neuromuscular blocking agents, adrenergic nerve inhibitors, anti-oxidants, vitamins, cosmetics, anti-inflammatories, wound care products, antithrombogenic agents, antitumoral agents, antiangiogenic agents, anesthetics, antigenic agents, wound healing agents, plant extracts, growth factors, emollients, humectants, rejection/anti-rejection drugs, spermicides, conditioners, antibacterial agents, antifungal agents, antiviral agents, antibiotics, tranquilizers, cholesterol-reducing drugs, antitussives, histamine-blocking drugs, monoamine oxidase inhibitor. All substances listed by the U.S. Pharmacopeia are also included within the substances of the present invention.

Other preferred embodiments involve the use of growth factors. Growth factors useful in the present invention include, but are not limited to, transforming growth factor-α ("TGF-α"), transforming growth factor-β ("TGF-β"), platelet-derived growth factors including the AA, AB and BB isoforms ("PDGF"), fibroblast growth factors ("FGF"), including FGF acidic isoforms 1 and 2, FGF basic form 2, and FGF 4, 8, 9 and 10, nerve growth factors ("NGF") including NGF 2.5 s, NGF 7.0 s and beta NGF and neurotrophins, brain derived neurotrophic factor, cartilage derived factor, bone growth factors (BGF), basic fibroblast growth factor, insulin-like growth factor (IGF), vascular endothelial growth factor (VEGF), granulocyte colony stimulating factor (G-CSF), insulin like growth factor (IGF) I and II, hepatocyte growth factor, glial neurotrophic growth factor (GDNF), stem cell factor (SCF), keratinocyte growth factor (KGF), transforming growth factors (TGF), including TGFs alpha, beta, beta1, beta2, and beta3, skeletal growth factor, bone matrix derived growth factors, and bone derived growth factors and mixtures thereof.

Cytokines useful in the present invention include, but are not limited to, cardiotrophin, stromal cell derived factor, macrophage derived chemokine (MDC), melanoma growth stimulatory activity (MGSA), macrophage inflammatory proteins 1 alpha (MIP-1alpha), 2, 3 alpha, 3 beta, 4 and 5, IL-1, IL-2, IL-3, IL-4, IL-5, IL-6, IL-7, IL-8, IL-9, IL-10, IL-11, IL-12, IL-13, TNF-α, and TNF-β. Immunoglobulins useful in the present invention include, but are not limited to, IgG, IgA, IgM, IgD, IgE, and mixtures thereof. Some preferred growth factors include VEGF (vascular endothelial growth factor), NGFs (nerve growth factors), PDGF-AA, PDGF-BB, PDGF-AB, FGFb, FGFa, and BGF.

Other molecules useful as substances in the present invention include, but are not limited to, growth hormones, leptin, leukemia inhibitory factor (LIF), tumor necrosis factor alpha and beta, endostatin, angiostatin, thrombospondin, osteogenic protein-1, bone morphogenetic proteins 2 and 7, osteonectin, somatomedin-like peptide, osteocalcin, interferon alpha, interferon alpha A, interferon beta, interferon gamma, interferon 1 alpha, and interleukins 2, 3, 4, 5 6, 7, 8, 9, 10, 11, 12, 13, 15, 16, 17 and 18.

Embodiments involving amino acids, peptides, polypeptides, and proteins may include any type of such molecules of any size and complexity as well as combinations of such molecules. Examples include, but are not limited to, structural proteins, enzymes, and peptide hormones. These compounds can serve a variety of functions. In some embodiments, the matrix may contain peptides containing a sequence that suppresses enzyme activity through competition for the active site. In other applications antigenic agents that promote an immune response and invoke immunity can be incorporated into a construct.

For substances such as nucleic acids, any nucleic acid can be present. Examples include, but are not limited to deoxyribonucleic acid (DNA), cnt-DNA, and ribonucleic acid (RNA). Embodiments involving DNA include, but are not limited to, cDNA sequences, natural DNA sequences from any source, and sense or anti-sense oligonucleotides. For example, DNA can be naked (e.g., U.S. Pat. Nos. 5,580,859; 5,910,488) or complexed or encapsulated (e.g., U.S. Pat. Nos. 5,908,777; 5,787,567). DNA can be present in vectors of any kind, for example in a viral or plasmid vector. In some embodiments, nucleic acids used will serve to promote or to inhibit the expression of genes in cells inside and/or outside the electroprocessed matrix. The nucleic acids can be in any form that is effective to enhance uptake into cells.

Substances in the electroprocessed collagen compositions of the present invention also comprise objects. Examples of objects include, but are not limited to, cell fragments, cell debris, organelles and other cell components, tablets, and viruses as well as vesicles, liposomes, capsules, nanoparticles, and other structures that serve as an enclosure for molecules. In some embodiments, the objects constitute vesicles, liposomes, capsules, or other enclosures that contain compounds that are released at a time after electroprocessing, such as at the time of implantation or upon later stimulation or interaction. In one illustrative embodiment, transfection agents such as liposomes contain desired nucleotide sequences to be incorporated into cells that are located in or on the electroprocessed material or matrix. In other embodiments, cell fragments, specific cell fractions or cell debris are incorporated into the matrix. The presence of cell fragments is known to promote healing in some tissues.

Magnetically or electrically reactive materials are also examples of substances that are optionally included within the electroprocessed collagen compositions of the present invention. Examples of magnetically active materials include but are not limited to ferrofluids (colloidal suspensions of magnetic particles), and various dispersions of electrically conducting polymers. Ferrofluids containing particles approximately 10 nm in diameter, polymer-encapsulated magnetic particles about 1-2 microns in diameter, and polymers with a glass transition temperature below room temperature are particularly useful. Examples of electrically active materials are polymers including, but not limited to, electrically conducting polymers such as polyanilines and polypyrroles, ionically conducting polymers such as sulfonated polyacrylamides are related materials, and electrical conductors such as carbon black, graphite, carbon nanotubes, metal particles, and metal-coated plastic or ceramic materials.

In other embodiments, some substances in the electroprocessed collagen materials or matrix supplement or augment the function of other substances. For example, when the composition comprises cells that express a specific gene, the composition can contain oligonucleotides that are taken up by the cells and affect gene expression in the cells. Fibronectin is optionally incorporated into the matrix to increase cellular uptake of oligonucleotides by pinocytosis.

As discussed in detail above, the electroprocessed material itself can provide a therapeutic effect. The invention thus includes embodiments involving methods of causing a therapeutic effect through delivery of an electroprocessed material to a location without incorporating additional substances in the electroprocessed material. Embodiments in which the matrix material alone is delivered as well as those in which other substances are included in the matrix are within the scope of the present invention.

Stability and Storage of the Electroprocessed Collagen Compositions

The stability of the electroprocessed collagen compositions of the present invention comprising electroprocessed collagen, also allows for long term storage of the compositions between formation and use. Stability allows greater flexibility for the user in embodiments in which a substance is applied after formation of the electroprocessed material, for example by soaking and spraying. A formed electroprocessed matrix can be fabricated and stored, and then the exact substance composition to be added in a specific application can be prepared and tailored to a specific need shortly before implantation or application. This feature allows users greater flexibility in both treatment options and inventory management. In many embodiments, electroprocessed collagen is dry once it is electroprocessed, essentially dehydrated, thereby facilitating storage in a dry or frozen state. Further, the electroprocessed collagen compositions are substantially sterile upon completion, thereby providing an additional advantage in therapeutic and cosmetic applications.

Storage conditions for the electroprocessed collagen compositions of the present invention will depend on the electroprocessed materials and substances therein. In some embodiments involving proteins, for example, it may be necessary or desirable to store the compositions at temperatures below 0° C., under vacuum, or in a lyophilized condition. Other storage conditions can be used, for example, at room temperature, in darkness, in vacuum or under reduced pressure, under inert atmospheres, at refrigerator temperature, in aqueous or other liquid solutions, or in powdered form. Persons of ordinary skill in the art recognize appropriate storage conditions for the materials and substances contained in the compositions and will be able to select appropriate storage conditions.

The electroprocessed collagen compositions of the present invention and formulations comprising those compositions may be sterilized through conventional means known to one of ordinary skill in the art. Such means include, but are not limited to, filtration, radiation, and exposure to sterilizing chemical agents such as peracetic acid or ethylene oxide gas. Heat may also be used in embodiments in which the application of heat will not denature the collagen. The compositions the present invention may also be combined with bacteriostatic agents, such as thimerosal, to inhibit bacterial growth.

Formulations comprising the electroprocessed collagen compositions of the present invention may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets commonly used by one of ordinary skill in the art. Preferred unit dosage formulations are those containing a dose or unit, or an appropriate fraction thereof, of the administered ingredient. It should be understood that in addition to the ingredients particularly mentioned above, the formulations of the present invention may include other agents commonly used by one of ordinary skill in the art.

The electroprocessed collagen compositions of the present invention may be packaged in a variety of ways depending upon the method used for administering the composition. Generally, an article for distribution includes a container which contains the composition or a formulation comprising the composition in an appropriate form. Suitable containers are well-known to those skilled in the art and include materials such as bottles (plastic and glass), sachets, ampules, plastic bags, metal cylinders, and the like. The container may also include a tamper-proof assemblage to prevent indiscreet access to the contents of the package. In addition, the container has deposited thereon a label which describes the contents of the container. The label may also include appropriate warnings.

Other Features of the Electroprocessed Collagen Compositions

The electroprocessed collagen compositions of the present invention have many beneficial features. Some features allow for use as an implant within or replacement of tissues or organs of the body of an organism. In many preferred embodiments, the electroprocessed materials form a matrix, preferably a matrix similar to an extracellular matrix. For example, the type of collagen selected can be based on the similarity to tissue in which the composition will be implanted, or, in the case of a prosthetic, the type of tissue, structure, or organ being replaced, repaired, or augmented. In such embodiments, the electroprocessed material is combined with other extracellular matrix materials to more closely mimic tissues. Such combination can occur before, during, or after formation of the matrix. Some extracellular materials are electroprocessed into a matrix along with the collagen or formed through other means. In some embodiments matrix materials are added to electroprocessed collagen once the matrix has been fabricated.

The electroprocessed collagen compositions of the present invention have many features that make them suitable for formation of extracellular matrices. The fibril structure and banding of electrospun collagen is similar to naturally occurring collagen. The density and structure of matrices formed by this method are greater than those achieved by known methods and are more similar to that of natural extracellular matrices.

In embodiments involving electrospun collagen, fibers are produced with much lower diameters than those that can be produced by known manufacturing processes. Electrospun collagen fibers have been observed to have cross-sectional diameters ranging from several microns down to below 100 nanometers. Electrospun fiber diameter can be manipulated by changing, for example, the composition (both in terms of sources and types of collagen and blending with other materials) and concentration of collagen and other materials to be electrospun. In many electrospinning embodiments, fiber diameter increases as the concentration present in the starting solutions increases. In some embodiments, fiber diameter increases as the viscosity of the starting solution increases. This can be a useful method of manipulation because inflammatory potential in some embodiments is inversely related to fiber diameter in a tissue-engineering scaffold. In some embodiments, the addition and removal of molecules that regulate or affect fiber formation can be added to manipulate collagen fiber formation. Many protcoglycans, for example, are known to regulate fiber formation, including affecting the diameter of the fibers. A wide range of fiber diameters are achievable in the practice of the present invention. Examples include, but are not limited to: Type I collagen with individual filament diameters ranging from about 100 to about 730 nm; Type I collagen fibers with an average diameter of 100±40 nm; Type II collagen fibers with an average diameter of 1.0 µm; Type II collagen fibers with an average diameter of 3±2.5 µm; Type II collagen fibers with an average diameter of 1.75±0.9 µm; Type II collagen fibers with an average diameter of 110±90 nm; Type III collagen fibers with average diameters of 250±150 nm; an electrospun blend of Type I and Type III collagen fibers with an average diameter of 390±290 nm; and a blend of Type I collagen/Type III collagen/elastin (45:35:20) having a diameter of 800±700 nm. Examples also include electrospun non-woven matrices about 200-250 microns thick and composed of fibrils of about 1 to about 5 µm in diameter, made separately from each of the following materials: electrospun type I collagen; electrospun gelatin; electrospun poly(glycolic) acid (PGA); electrospun poly(lactic) acid (PLA); electrospun PGA/PLA co-polymer; an electrospun blend of type I collagen and PGA/PLA co-polymer; and, an electrospun blend of gelatin and PGA/PLA co-polymers. Ranges of larger fiber sizes are also possible. In one desirable embodiment, the fibers range between about 10 nm and about 100 µm in average diameter. In another desirable embodiment, the fibers range between about 50 nm and about 1 µm in average diameter. In another desirable embodiment, the fibers range between about 100 nm and about 1 µm in average diameter. In one preferred embodiment, the diameters of the electroprocessed material are similar to that of extracellular matrix materials in vivo. The foregoing discussion regarding possible fiber diameter ranges is not limited to collagen, or to specific types of collagen, but applies to all types of electroprocessed materials, including all types of collagen, all other types of natural materials, and all types of synthetic materials. It is to be understood that the invention includes electroprocessed fibers and materials of any diameter, and that none of the above diameters or ranges is intended to be limiting. Examples of preferred embodiments involving electrospun collagen of a specific type and specific diameter include, but are not limited to: electrospun Type I collagen fibers with an average diameter between about 50 nm and about 10 µm, more preferably between about 50 nm and about 1 µm; electrospun Type II collagen fibers within an average fiber diameter between about 10 nm and about 80 nm; electrospun Type III collagen fibers within an average fiber diameter between about 30 nm and about 150 nm. In many embodiments, the electrospun material forms as a continuous fiber such that spun materials show no evidence of free ends upon microscopic examination. Other embodiments do not involve such formation of a continuous fiber.

The present invention permits design and control of pore size in an electroprocessed material through manipulation of the composition of the material and the parameters of electroprocessing. In some embodiments, the electroprocessed material has a pore size that is small enough to be impermeable to one or more types of cells. In some embodiments, for example, the pore size is such that the electroprocessed material is impermeable to red blood cells. In some embodiments, the pore size is such that the electroprocessed material is impermeable to platelets. In one embodiment, the average pore diameter is about 500 nanometers or less. In another embodiment, the average pore diameter is between about 500 nanometers and about 1 micron. In another embodiment, the average pore diameter is about 1 micron or less. In another embodiment, the average pore diameter is about 2 microns or less. In another embodiment, the average pore diameter is about 5 microns or less. In another embodiment, the average pore diameter is about 8 microns or less. In another embodiment, the average pore diameter is about 10 microns or less. Some embodiments have pore sizes that do not impede cell infiltration at all. One preferred embodiment has a pore surface area between about 0.1 and about 100 $\mu m^2$. A further preferred embodiment has a pore surface area between about 0.1 and about 50 $\mu m^2$. A further preferred embodiment has a pore surface area between about 1.0 $\mu m^2$ and about 25 $\mu m^2$. A further preferred embodiment has a pore surface area between about 1.0 $\mu m^2$ and about 5 $\mu m^2$. Infiltration can also be accomplished with implants with smaller pore sizes. For porous structures, the interaction is dependent on the size, size distribution, and continuity of pores within the structure of the device. It was previously thought that pore size must be greater than about 10 microns for cells to be capable of migrating into, out of, or through the structure. It has been observed, however, that implants comprised of electrospun nanofibers of at least some types of natural proteins are not subject to this limitation. In one embodiment significant cellular migration occurred into an electrospun collagen/elastin with an average pore size of 3.7 microns. Infiltration can also be accomplished with implants with smaller pore sizes. Pore size of an electroprocessed collagen matrix can be readily manipulated through control of process parameters, for example by controlling fiber deposition rate through electric field strength and mandrel motion, by varying solution concentration (and thus fiber size). Porosity can also be manipulated by mixing porogenic materials, such as salts or other extractable agents, the of which will leave holes of defined sizes in the matrix. If desired, the degree to which cells infiltrate a matrix can be controlled to a degree by the amount of cross-linking present in the matrix. A highly cross-linked matrix is not as rapidly infiltrated as a matrix with a low degree of cross-linking. Adding synthetic materials to a matrix can also limit the degree to which cells will infiltrate the material.

Electroprocessed collagen has the further advantage of having greater structural strength than known collagen implants, and of retaining that structural strength after implantation. Electroprocessed matrices have greater structural integrity than the collagen gels used in current implants. They also show less susceptibility to reformation and resorption after implantation than known collagen matrix technologies. Furthermore, the present invention includes methods of controlling the degree to which the electroprocessed collagen will be resorbed. In some embodiments electrospun collagen can be resorbed quite quickly, in a period of 7-10 days or shorter. In other embodiments, features such as extensive cross-linking of collagen fibrils is used to make the matrix very stable and able to last months to years. Variation of crosslinking also provides a further ability to mimic natural tissue. Natural collagens within the body exhibit differing degrees of cross-linking and biological stability. The degree of cross-linking in native collagens may vary as a function of age, physiological status and in response to various disease processes.

Crosslinking is one of many factors that permit control of the mechanical properties of the electroprocessed matrix. A number of embodiments exist. Examples include but are not limited to: a dry sample of Type I collagen electrospun fiber scaffold, crosslinked by exposure to glutaraldehyde vapor for approximately 2.5 hours, having an elastic modulus of 52 MPa and a peak stress of 1.5 MPa; a Type I collagen electrospun fiber scaffold, also crosslinked by exposure to glutaraldehyde vapor for approximately 2.5 hours, then hydrated in PBS for three hours, having an elastic modulus of 0.2 MPa with a peak stress of 0.1 MPa; and a Type I collagen electrospun fiber scaffold, crosslinked by exposure to glutaraldehyde vapor for 24 hours, then hydrated in PBS for three hours, having a modulus of 1.5 MPa with a peak stress of 0.25 MPa; uncrosslinked Type II collagen scaffolds revealed a tangent modulus of 172.5 MPa and an ultimate tensile strength of 3.298 MPa; In preferred embodiments, mechanical properties of the electroprocessed matrix are within ranges found within natural extracellular matrix materials and tissues. Examples include, but are not limited to, matrices with an elastic modulus between about 0.5 and about 10 MPa when hydrated and matrices with an elastic modulus between about 2 and about 10 MPa when hydrated. These values for elastic modulus and peak stress are not intended to be limiting, and electroprocessed matrices with any type of mechanical properties are within the scope of this invention.

The ability to combine electroprocessed collagen compositions with other electroprocessed materials provides numerous additional advantages. Preparing a composition or construct comprising electroprocessed collagen and additional electroprocessed extracellular matrix materials can further enhance the ability to mimic the extracellular matrix. In some embodiments, electroprocessed collagen can be combined with electroprocessed materials such as fibrin, elastin, laminin, fibronectin, integrin, hyaluronic acid, chondroitin 4-sulfate, chondroitin 6-sulfate, dermatan sulfate, heparin sulfate, heparin, and keratan sulfate, and proteoglycans in appropriate relative amounts to mimic the composition of extracellular matrix materials. Where appropriate, substances comprising extracellular materials can be prepared by means other than electroprocessing and combined with the electroprocessed collagen. In some embodiments, more crude extracts of collagen isolated from the connective tissues can be electroprocessed. In such embodiments, the matrix contains a variety of structural and regulatory elements that may be needed to promote activities such as healing, regeneration, and cell differentiation.

Other electroprocessed materials can be included in the matrix to provide other matrix properties. One example is the ability to control the persistence or biodegradation of the implanted matrix. Fibrin as a matrix material tends to degrade faster when implanted than collagen, while some synthetic polymers tend to degrade more slowly. Controlling the relative content of these materials will affect the rate at which the matrix degrades. As another example, materials may be included to increase the susceptibility of a matrix or construct formed from a matrix to heat sealing, chemical sealing, and application of mechanical pressure or a combination thereof. It has been observed that inclusion of synthetic polymers enhances the ability of matrices to be cauterized or heat sealed. The inclusion of electrically or magnetically reactive polymers in matrix materials is another example. In some embodiments, such polymers are used to prepare matrices that are conductive, that provide a piezoelectric effect, or that alter the shape, porosity and/or density of the electroprocessed material in response to an electric or magnetic field. Another example is the use of matrix material known to have therapeutic effects. For example, fibrin matrix material assists in arrest of bleeding. Fibrin is a component of the provisional matrix that is laid down during the early stages of healing and may also promote the growth of vasculature in adjacent regions, and in many other ways is a natural healing promoter.

The ability to incorporate substances into an electroprocessed composition allows for additional benefits. One such benefit is even closer mimicry of tissue and greater compatibility for implants. In some preferred embodiments, stem cells, committed stem cells that will differentiate into the desired cell type, or differentiated cells of the desired type, are incorporated to more closely mimic tissue. Furthermore, the methods available for encapsulating or otherwise combining cells with electroprocessed collagen leads to greater cell density in the matrix than that achievable by known methods. This density is enhanced further by the improved cell infiltration discussed above.

The ability of compositions of the present invention to mimic natural materials minimizes the risk of immune rejection of an implanted matrix. For example, autologous material can be used. However, the close resemblance to natural materials has allowed avoidance of immune reaction even in some embodiments in which heterologous materials are used. For example, electrospun cylinders of bovine Type I collagen (25 mm long by 2 mm wide) implanted into the rat vastus lateralis muscle showed no immune response after 7-10 days. Similar constructs composed of electrospun Type I collagen were supplemented with satellite muscle cells and implanted. Similar results occurred, no evidence of inflammation or rejection and the implants were densely populated. Furthermore, some embodiments of the matrices have been observed to avoid encapsulation of implants by recipient tissue, a common problem with implants. In embodiments in which encapsulation is desired, matrix structure is altered to promote inflammation and encapsulation.

Substances that can provide favorable matrix characteristics also include drugs and other substances that can produce a therapeutic or other physiological effect on cells and tissues within or surrounding an implant. Any substance may be used. In many preferred embodiments, substances are included in the electroprocessed collagen matrix that will improve the performance of the implanted electroprocessed matrix. Examples of substances that can be used include but are not limited to peptide growth factors, antibiotics, and/or anti-rejection drugs. Chemicals that affect cell function, such as oligonucleotides, promoters or inhibitors of cell adhesion, hormones, and growth factor are additional examples of substances that can be incorporated into the electroprocessed collagen material and the release of those substances from the electroprocessed material can provide a means of controlling expression or other functions of cells in the electroprocessed material. Alternatively, cells that are engineered to manufacture desired compounds can be included. The entire construct is, for example, cultured in a bioreactor or conventional culture or placed directly in vivo. For example, neovascularization can be stimulated by angiogenic and growth-promoting factors, administered, as peptides, proteins or as gene therapy. Angiogenic agents can be incorporated into the electroprocessed collagen matrix. Alternatively, where neovascularization is not desired, antiangiogenic materials, such as angiostatin, may be included in the electroprocessed collagen matrix. Nerve growth factors can be electrospun into the electroprocessed collagen matrix to promote growth or neurons into the matrix and tissue. In a degradable electroprocessed collagen matrix, the gradual degradation/breakdown of the matrix will release these factors and accelerate growth of desired tissues. Substances can be incorporated into the electroprocessed collagen matrix to regulate differentiation of cells in the matrix. Oligonucleotides and peptides drugs such as retinoic acid are examples of such substances. Oligonucleotide DNA or messenger RNA sequences coding for specific proteins in the sense and antisense direction can also be used. For example, where expression of a protein is desired, sense oligonucleotides can be provided for uptake by cells and expression. Antisense oligonucleotides can be released, for example, to suppress the expression gene sequences of interest. Implants can be designed such that the substances affect cells contained within the matrix, outside the matrix or both.

Several methods exist for studying and quantifying specific characteristics of the matrix materials of the present invention. The fiber diameter and pore dimensions (porosity) for collagen-based matrices can be determined, for example, by SEM micrograph that are digitized and analyzed with UTH-SCSA ImageTool 2.0 (NIH Shareware). Water permeability, a characteristic that differs from porosity, may also be studied using standard methods. Atomic force microscopy can also be used to prepare three-dimensional images of surface topography of biological specimens in ambient liquid or gas environments and over a large range of temperatures. This tool allows determination of relationship and interaction between matrix components. Construct composition analysis can include, for example, histology analysis to determine the degree of cellular distribution through the constructs interstitial space. To assist this analysis, cells may be stained with any known cell staining technique (for example, hematoxylin and eosin and Masson's trichrome). Cell proliferative activity of cells can be studied, for example, by labeling cells biosynthetically with a label that is incorporated into calls actively undergoing DNA synthesis (for example, with bromodeoxyurdine) and using anti-label antibodies to determine the extent to which cells are undergoing nuclear division. Cellular density may be determined, for example, by measuring the amount of DNA in enzyme-digested samples utilizing known techniques. Degree of degradation or remodeling of the collagen matrix by cells may be determined by, for example, measuring expression and activity of matrix metalloproteinases from cells. One way of measuring functionality of cells in electroprocessed collagen matrices is by measuring various physiological endpoints characteristic of the tissues. For example, muscle cells may be stimulated with an electrical signal or challenged with chemical agents or drugs, for example carbachol, to determine the contractability of a construct. Function of cells in an endocrine construct can be determined by measuring production of the desired hormones. One skilled in the art will understand that the foregoing list is not exhaustive and numerous parameters and endpoints can be used in characterizing tissues and matrices using existing methods.

Methods of Making the Electroprocessed Collagen Compositions Electroprocessing

The methods of making the electroprocessed collagen compositions include, but is not limited, to electroprocessing collagen and optionally electroprocessing other materials, substances or both. As defined above, one or more electroprocessing techniques, such as electrospin, electrospray, electroaerosol, electrosputter, or any combination thereof, may be employed to make the electroprocessed collagen and matrices in the compositions of the present invention. In the most fundamental sense, the electroprocessing apparatus for electroprocessing material includes a electrodepositing mechanism and a target substrate. The electrodepositing mechanism includes a reservoir or reservoirs to hold the one or more solutions that are to be electroprocessed or electrodeposited. The reservoir or reservoirs have at least one orifice or nozzle to allow the streaming of the solution from the reservoirs. Although the terms "orifice" and "nozzle" are used throughout, these term are not intended to be limiting, and refer generically to any location from which solutions may stream during electroprocessing. One or a plurality of nozzles may be configured in an electroprocessing apparatus. If there are multiple nozzles, each nozzle is attached to one or more reservoirs containing the same or different solutions. Similarly, there can be a single nozzle that is connected to multiple reservoirs containing the same or different solutions. Multiple nozzles may be connected to a single reservoir. Because different embodiments involve single or multiple nozzles and/or reservoirs, any references herein to one or nozzles or reservoirs should be considered as referring to embodiments involving single nozzles, reservoirs, and related equipment as well as embodiments involving plural nozzles, reservoirs, and related equipment. The size of the nozzles can be varied to provide for increased or decreased flow of solutions out of the nozzles. One or more pumps used in connection with the reservoirs can be used to control the flow of solution streaming from the reservoir through the nozzle or nozzles. The pump can be programmed to increase or decrease the flow at different points during electroprocessing. In this invention pumps are not necessary but provide a useful method to control the rate at which material is delivered to the electric field for processing. Material can be actively delivered to the electric field as a preformed aerosol using devices such as air brushes, thereby increasing the rate of electrodeposition and providing novel combinations of materials. Nozzles may be programmed to deliver material simultaneously or in sequence.

The electroprocessing occurs due to the presence of a charge in either the orifices or the target, while the other is grounded. In some embodiments, the nozzle or orifice is charged and the target is shown to be grounded. Those of skill in the electroprocessing arts will recognize that the nozzle and solution can be grounded and the target can be electrically charged. The creation of the electrical field and the effect of the electrical field on the electroprocessed materials or substances that will form the electroprocessed composition occur whether the charge is found in the solution or in the grounded target. In different embodiments, the space between the target and the nozzle or source of the materials can contain air or selected gases. In various embodiments, the space can be maintained under a vacuum or below atmospheric pressure or above normal atmospheric pressure. Solvents used in electroprocessing typically evaporate during the process. This is considered advantageous because it assures that the electroprocessed materials are dry. In embodiments using water or other less volatile solvents, electroprocessing may optionally occur in a vacuum or other controlled atmosphere (for example, an atmosphere containing ammonia) to assist evaporation. Electroprocessing can be oriented varying ways with respect to gravity forces or occur in a zero gravity environment.

The substrate can also be used as a variable feature in the electroprocessing of materials used to make the electroprocessed composition. Specifically, the target can be the actual substrate for the materials used to make electroprocessed matrix, or electroprocessed matrix itself is deposited. Alternatively, a substrate can be disposed between the target and the nozzles. For instance, a petri dish can be disposed between nozzles and a target, and a matrix can be formed in the dish. Other variations include but are not limited to non-stick surfaces between the nozzles and target and placing tissues or surgical fields between the target and nozzles. The target can also be specifically charged or grounded along a preselected pattern so that the solution streamed from the orifice is directed into specific directions. The electric field can be controlled by a microprocessor to create an electroprocessed matrix having a desired geometry. The target and the nozzle or nozzles can be engineered to be movable with respect to each other, thereby allowing additional control over the geometry of the electroprocessed matrix to be formed. The entire process can be controlled by a microprocessor that is programmed with specific parameters that produce a specific preselected electroprocessed matrix. It is to be understood that any electroprocessing technique may be used, alone or in combination with another electroprocessing technique, to make the compositions of the present invention.

Forms of electroprocessed collagen include but are not limited to preprocessed collagen in a liquid suspension or solution, gelatin, particulate suspension, or hydrated gel. Where fibrin is also electroprocessed, the fibrin may be used as a preformed gel electroprocessed by subjecting it to pressure, for example by using a syringe or airbrush apparatus with a pressure head behind it to extrude the fibrin gel into the electrical field. In general, when producing fibers using electroprocessing techniques, especially electrospinning, it is preferable to use the monomer of the polymer fiber to be formed. In some embodiments it is desirable to use monomers to produce finer filaments. In other embodiments, it is desirable to include partial fibers to add material strength to the matrix and to provide additional sites for incorporating substances. Matrix materials such as collagen in a gelatin form may be used to improve the ability of the material to dissolve. Acid extraction method can be used in preparing such gels to maintain the structure of the monomeric subunits. Units can then be treated with enzymes to alter the structure of the monomers.

In embodiments in which two materials combine to form a third material, the solutions containing these components can be mixed together immediately before they are streamed from an orifice in the electroprocessing procedure. In this way, the third material forms literally as the microfibers or microdroplets are formed in the electrospinning process. Alternatively, such matrices can be formed by electrospraying a molecule that can form matrix materials into a moist or otherwise controlled atmosphere of other molecules necessary to allow formation of the matrix to form filaments within the electric field.

Alternatively, in embodiments in which two or more matrix materials are combined to form a third, the matrix materials can be electroprocessed in conjunction with or separately from each other. In some desirable embodiments, this occurs under conditions that do not allow the two molecules to form the third molecule until the desired time. This can be accomplished several ways. Alternatively, molecules can be mixed with a carrier, such as PEO, or other synthetic or natural polymers such as collagen. The carrier acts to hold the reactants in place until they are initiated.

As stated above, it is to be understood that carriers can be used in conjunction with matrix materials. Different materials, such as extracellular matrix proteins, and or substances, can be mixed with PEG or other known carriers that form filaments. For example, collagen and fibrinogen and can be mixed with PEG or other known carriers that form filaments. This produces “hairy filaments” with the hair being collagen, fibrin, or other matrix material. The “hairs” cross-link the surrounding matrix carrier into a gel, or provide reactive sites for cells to interact with the substance within the matrix carrier, such as immunoglobulins. This approach can be used for forming a matrix or gelling molecules that do not normally gel.

Alternatively, the electroprocessed collagen can be sputtered to form a sheet. Other molecules that form sheets include PGA, PLA, a copolymer of PGA and PLA, collagen, and fibronectin. In some embodiments, a sheet is formed with two or more materials that can combine to form a third material. This sheet can be placed in a wet environment to allow conversion to the third material.

In addition to the multiple equipment variations and modifications that can be made to obtain desired results, similarly the electroprocessed collagen solution can be varied to obtain different results. For instance, any solvent or liquid in which the material is dissolved, suspended, or otherwise combined without deleterious effect on the process or the safe use of the matrix can be used. Materials or the compounds that form materials can be mixed with other molecules, monomers or polymers to obtained desired results. In some embodiments, polymers are added to modify the viscosity of the solution. In still a further variation, when multiple reservoirs are used, the ingredients in those reservoirs are electroprocessed separately or joined at the nozzle so that the ingredients in the various reservoirs can react with each other simultaneously with the streaming of the solution into the electric field. Also, when multiple reservoirs are used, the different ingredients in different reservoirs can be phased in temporally during the processing period. These ingredients may include substances.

Embodiments involving alterations to the electroprocessed collagen itself are within the scope of the present invention. Some materials can be directly altered, for example, by altering their carbohydrate profile or the amino acid sequence of a protein, peptide, or polypeptide. Also, other materials can be attached to the matrix materials before, during or after electroprocessing using known techniques such as chemical cross-linking or through specific binding interactions. Further, the temperature and other physical properties of the process can be modified to obtain different results. The matrix may be compressed or stretched to produce novel material properties. Still further chemical variations are possible.

Electroprocessing using multiple jets of different polymer solutions and/or the same solutions with different types and amounts of substances (e.g., growth factors) can be used to prepare libraries of biomaterials for rapid screening. Such libraries are desired by those in the pharmaceutical, advanced materials and catalyst industries using combinatorial synthesis techniques for the rapid preparation of large numbers (e.g., libraries) of compounds that can be screened. For example, the minimum amount of growth factor to be released and the optimal release rate from a fibrous collagen scaffold to promote the differentiation of a certain type of cell can be investigated using the compositions and methods of the present invention. Other variables include type of collagen, and fiber diameter. Electroprocessing permits access to an array of samples on which cells can be cultured in parallel and studied to determine selected compositions which serve as promising cell growth substrates.

Figure 3:
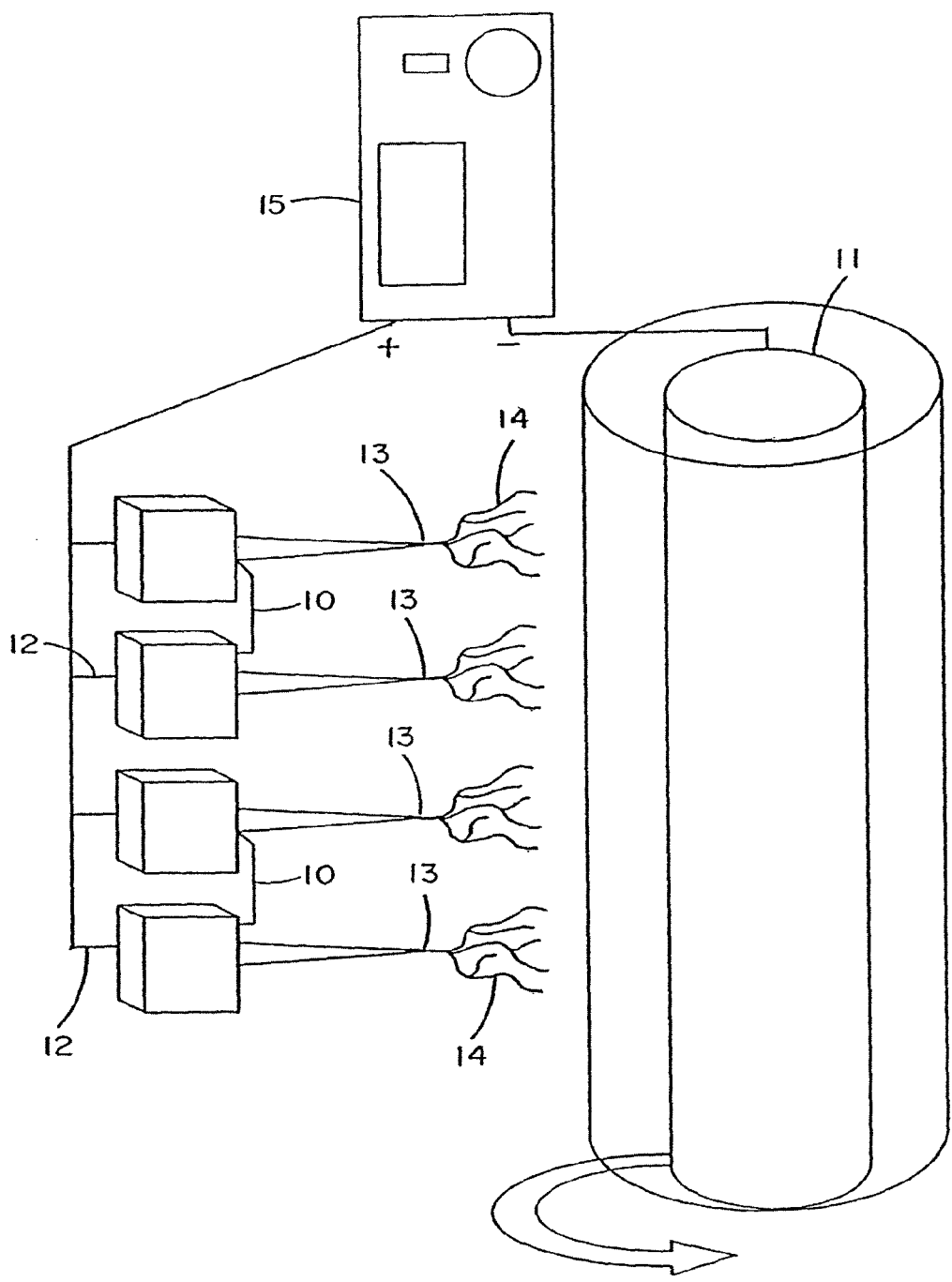
FIG. 3. is a schematic drawing of an embodiment of an electroprocessing device including the electroprocessing equipment and a rotating wall bioreactor.

Various effective conditions can be used to electroprocess a collagen matrix. While the following is a description of a preferred method, other protocols can be followed to achieve the same result. Referring to FIG. 3, in electrospinning collagen fibers, micropipettes 10 are filled with a solution comprising collagen and suspended above a grounded target 11, for instance, a metal ground screen placed inside the central cylinder of the RCCS bioreactor. Although this embodiment involves two micropipettes acting as sources of materials, the present invention includes embodiments involving only one source or more than two sources. A fine wire 12 is placed in the solution to charge the solution in each pipette tip 13 to a high voltage. At a specific voltage determined for each solution and apparatus arrangement, the solution suspended in each pipette tip is directed towards the grounded target. This stream 14 of materials may form a continuous filament, for example when collagen is the material, that upon reaching the grounded target, collects and dries to form a three-dimensional, ultra thin, interconnected matrix of electroprocessed collagen fibers. Depending upon reaction conditions a single continuous filament may be formed and deposited in a non-woven matrix.

Figure 4:
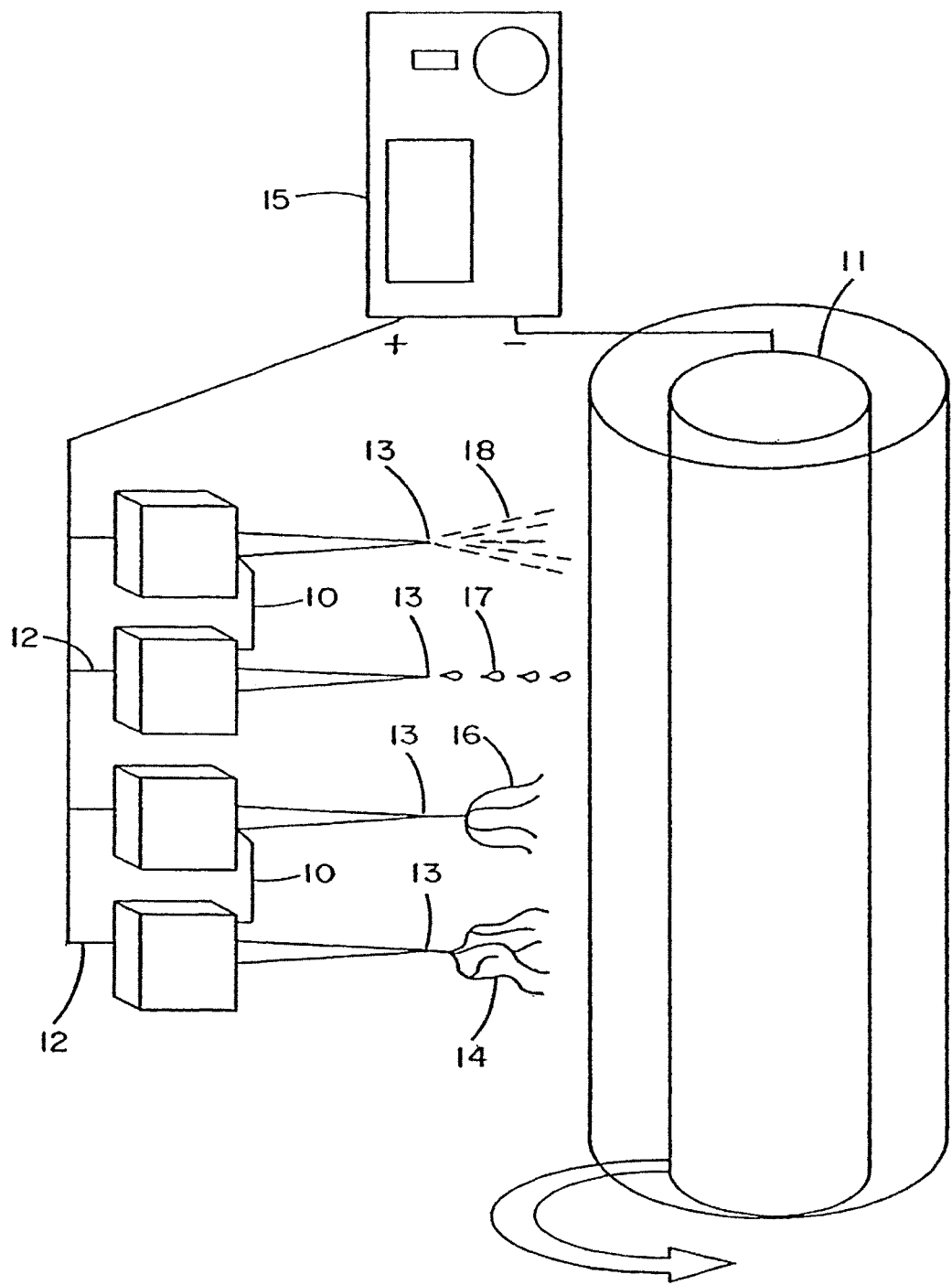
FIG. 4. is a schematic drawing of an embodiment of an electroprocessing device including the electroprocessing equipment and a rotating wall bioreactor.

As noted above, combinations of electroprocessing techniques and substances are used in some embodiments. Referring now to FIG. 4 micropipette tips 13 are each connected to micropipettes 10 that contain different materials or substances. The micropipettes are suspended above a grounded target 11. Again, fine wires 12 are used to charge the solutions. One micropipette produces a stream of collagen fibers 14. Another micropipette produces a steam of electrospun PLA fibers 16. A third micropipette produces an electroaerosol of cells 17. A fourth micropipette produces an electrospray of PLA droplets 18. Although the micropipettes are attached to the same voltage supply 15, PLA is electrosprayed rather than electrospun from the fourth micropipette due to variation in the concentration of PLA in the solutions. Alternatively, separate voltage supplies (not shown) can be attached to each micropipette to allow varying electroprocessing methods to be used through application of different voltage potentials.

Figure 5:
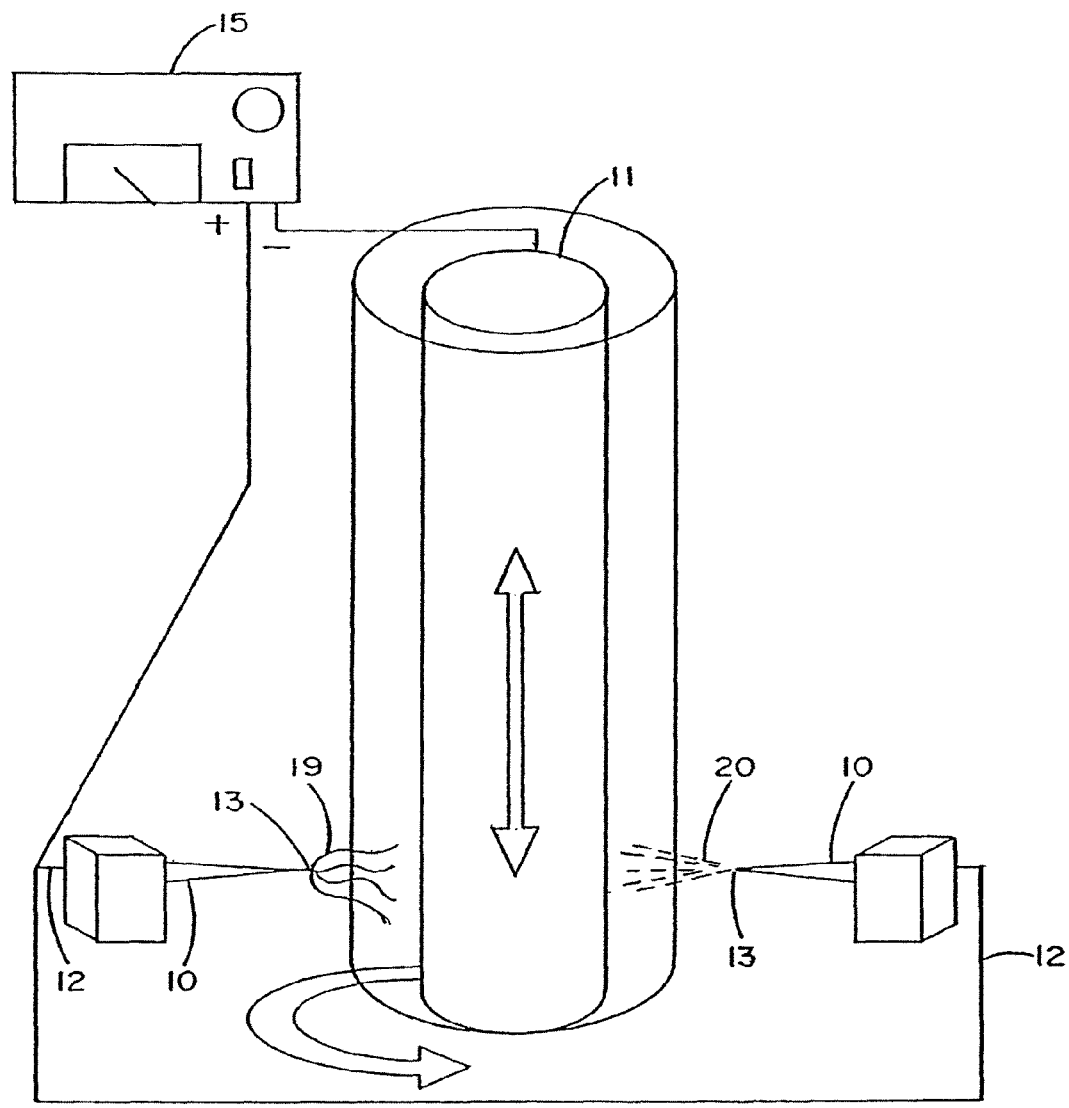
FIG. 5. is a schematic drawing of another embodiment of an electroprocessing device including the electroprocessing equipment and a rotating wall bioreactor.

Similarly, referring now to FIG. 5, collagen material can be applied as electrospun collagen fibers 19 from one of the two micropipettes and electrosprayed collagen droplets 20 from the other micropipette disposed at a different angle with respect to the grounded substrate 11. Again, the micropipette tips 13 are attached to micropipettes 10 that contain varying concentrations of materials and thus produce different types of electroprocessed streams despite using the same voltage supply 15 through fine wires 12.

Minimal electrical current is involved in this process, and, therefore, electroprocessing, in this case electrospinning, does not denature the collagen and other materials that are electroprocessed, because the current causes little or no temperature increase in the solutions during the procedure. In melt electroprocessing, there is some temperature increase associated with the melting of the material. In such embodiments, care is exercised to assure that the materials or substances are not exposed to temperatures that will denature or otherwise damage or injure them.

An electroaerosoling process can be used to produce a dense, matte-like matrix of electroprocessed droplets of material. The electroaerosoling process is a modification of the electrospinning process in that the electroaerosol process utilizes a lower concentration of matrix materials or molecules that form electroprocessed materials during the procedure. Instead of producing a splay of fibers or a single filament at the charge tip of the nozzle, small droplets are foamed. These droplets then travel from the tip to the substrate to form a sponge-like matrix composed of fused droplets. In some embodiments, the droplets are less than 10 microns in diameter. In other embodiments a construct composed of fibrils with droplets, like "beads on a string" may be produced. Droplets may range in size from 100 nanometers to 10 microns depending on the polymer and solvents.

As with the electrospinning process described earlier, the electroaerosol process can be carried out using various effective conditions. The same apparatus that is used in the electrospinning process, for instance as shown in FIG. 5 is utilized in the electroaerosol process. The differences from electrospinning include the concentration of the materials or substances that form matrix materials placed in solution in the micropipette reservoir and/or the voltage used to create the stream of droplets.

One of ordinary skill in the art recognizes that changes in the concentration of materials or substances in the solutions requires modification of the specific voltages to obtain the formation and streaming of droplets from the tip of a pipette.

The electroprocessing process can be manipulated to meet the specific requirements for any given application of the electroprocessed compositions made with these methods. In one embodiment, the micropipettes can be mounted on a frame that moves in the x, y and z planes with respect to the grounded substrate. The micropipettes can be mounted around a grounded substrate, for instance a tubular mandrel. In this way, the materials or molecules that form materials streamed from the micropipettes can be specifically aimed or patterned. Although the micropipettes can be moved manually, the frame onto which the micropipettes are mounted is preferably controlled by a microprocessor and a motor that allow the pattern of streaming collagen to be predetermined by a person making a specific matrix. Such microprocessors and motors are known to one of ordinary skill in the art. For instance, matrix fibers or droplets can be oriented in a specific direction, they can be layered, or they can be programmed to be completely random and not oriented.

In the electrospinning process, the stream or streams can branch out to form fibers. The degree of branching can be varied by many factors including, but not limited to, voltage, ground geometry, distance from micropipette tip to the substrate, diameter of micropipette tip, and concentration of materials or compounds that will form the electroprocessed materials. As noted, not all reaction conditions and polymers may produce a true multifilament, under some conditions a single continuous filament is produced. Materials and various combinations can also be delivered to the electric field of the system by injecting the materials into the field from a device that will cause them to aerosol. This process can be varied by many factors including, but not limited to, voltage (for example ranging from about 0 to 30,000 volts), distance from micropipette tip to the substrate (for example from 0-40 cm), the relative position of the micropipette tip and target (i.e. above, below, aside etc.), and the diameter of micropipette tip (approximately 0-2 mm). Several of these variables are well-known to those of skill in the art of electrospinning microfiber textile fabrics.

The geometry of the grounded target can be modified to produce a desired matrix. By varying the ground geometry, for instance having a planar or linear or multiple points ground, the direction of the streaming materials can be varied and customized to a particular application. For instance, a grounded target comprising a series of parallel lines can be used to orient electrospun materials in a specific direction. The grounded target can be a cylindrical mandrel whereby a tubular matrix is formed. Most preferably, the ground is a variable surface that can be controlled by a microprocessor that dictates a specific ground geometry that is programmed into it. Alternatively, for instance, the ground can be mounted on a frame that moves in the x, y, and z planes with respect to a stationary micropipette tip streaming collagen.

The substrate onto which the materials are streamed, sprayed or sputtered can be the grounded target itself or it can be placed between the micropipette tip and the grounded target. The substrate can be specifically shaped, for instance in the shape of a nerve guide, skin patch, fascial sheath, or a vascular graft for subsequent use in vivo. The electroprocessed compositions can be shaped to fit a defect or site to be filled. Examples include a site from which a tumor has been removed, an injury site in the skin (a cut, a biopsy site, a hole or other defect) and a missing or shattered piece of bone. The electroprocessed compositions may be shaped into shapes useful for substance delivery, for example, a skin patch, a lozenge for ingestion, an intraperitoneal implant, a subdermal implant, the interior or exterior lining of a stent, a cardiovascular valve, a tendon, a cornea, a ligament a dental prosthesis, a muscle implant, or a nerve guide. Electroprocessing allows great flexibility and allows for customizing the construct to virtually any shape needed. Many matrices are sufficiently flexible to allow them to be formed to virtually any shape. In shaping matrices, portions of the matrix may be sealed to one another by, for example, heat sealing, chemical sealing, and application of mechanical pressure or a combination thereof. An example of heat sealing is the use of crosslinking techniques discussed herein to form crosslinking between two portions of the matrix. Sealing may also be used to close an opening in a shaped matrix. Suturing may also be used to attach portions of matrices to one another or to close an opening in a matrix. It has been observed that inclusion of synthetic polymers enhances the ability of matrices to be heat sealed.

Other variations of electroprocessing, particularly electrospinning and electroaerosoling include, but are not limited to the following:

1. Using different solutions to produce two or more different fibers or droplets simultaneously (fiber or droplet array). In this case, the single component solutions can be maintained in separate reservoirs.

2. Using mixed solutions (for example, materials along with substances such as cells, growth factors, or both) in the same reservoir(s) to produce fibers or droplets composed of electroprocessed materials as well as one or more substances (fiber composition "blends"). Nonbiological but biologically compatible material can be mixed with a biological molecule.

3. Utilizing multiple potentials applied for the different solutions or the same solutions.

4. Providing two or more geometrically different grounded targets (i.e. small and large mesh screens).

5. Placing the mold or mandrel or other ungrounded target in front of the grounded target.

6. Applying agents such as Teflon onto the target to facilitate the removal of electroprocessed materials from the target (i.e. make the material more slippery so that the electroprocessed materials do not stick to the target).

7. Forming an electroprocessed material that includes materials applied using multiple electroprocessing methods. For example, electrospun fibers and electroaerosol droplets in the same composition can be beneficial for some applications depending on the particular structure desired. This combination of fibers and droplets can be obtained by using the same micropipette and solution and varying the electrical charge; varying the distance from the grounded substrate; varying the polymer concentration in the reservoir; using multiple micropipettes, some for streaming fibers and others for streaming droplets; or any other variations to the method envisioned by those of skill in this art. The fibers and droplets can be layered or mixed together in same layers. In applications involving multiple micropipettes, the micropipettes can be disposed in the same or different directions and distances with reference to the target.

8. Using multiple targets.

9. Rotating targets or mandrels during electroprocessing to cause the electroprocessed materials to have a specific polarity or alignment.

10. Use of processing aids. Any processing aid as defined above may be used.

All these variations can be done separately or in combination to produce a wide variety of electroprocessed materials and substances.

In one embodiment, the addition of 0.75 NaOH to a TFE solvent promotes formation of a solution or suspension of a material to be electroprocessed.

In some embodiments, the pH of the solution is manipulated to control the pH of the resulting electroprocessed material. In one embodiment, hydrochloric acid is added to the electroprocessing solutions immediately prior to electroprocessing. In some embodiments, the pH solution is adjusted to values ranging from 4 to 14. In other embodiments, a buffer is added to the solvent prior to electroprocessing to control pH. Examples of such buffers include, but are not limited to HEPES, MOPS, PBS and other phosphate based buffers.

The various properties of the electroprocessed materials can be adjusted in accordance with the needs and specifications of the cells to be suspended and grown within them. The porosity, for instance, can be varied in accordance with the method of making the electroprocessed materials or matrix. Electroprocessing a particular matrix, for instance, can be varied by fiber (droplet) size and density. If the cells to be grown in the matrix require a great deal of nutrient flow and waste expulsion, then a loose matrix can be created. On the other hand, if the tissue to be made requires a very dense environment, then a dense matrix can be designed. Porosity can be manipulated by mixing salts or other extractable agents. Removing the salt will leave holes of defined sizes in the matrix.

In one embodiment for electroprocessing collagen, the appropriate approximate ranges are: voltage 0-30,000 volts; pH 7.0 to 8.0; temperature 20 to 42° C.; and collagen 0 to 5 mg/ml. One embodiment for electrospraying collagen uses collagen at a concentration of 0.008 g/1.0 ml acid extracts of Type I collagen (calfskin) dissolved in HFIP, electroprocessed from a syringe at a 25 kV at a distance from the target of 127 mm and a syringe pump rate of 10 ml/hr. At this concentration the collagen did not exhibit any evidence of electrospinning (fiber formation) and, regardless of the input voltage, the polymer solution formed electrosprayed droplets and leakage from the syringe tip. One embodiment for elastin uses elastin from Ligamentum Nuchae dissolved in 70% isopropanol/water at a concentration of 250 mg/ml. The solution is then agitated to ensure mixing and loaded into a 1 ml syringe. Once loaded, the syringe is placed onto a syringe pump and set at a flow rate of 10 ml/hr. A mandrel is placed 7 inches from the syringe tip and rotated at a selected speed. The pump and power supply are then turned on and the voltage is set for 24,000 kilovolts. Electroprocessed collagen matrices of varying properties can be engineered by shifting the pH, changing the ionic strength (e.g. addition of organic salts), or adding additional polymeric substrates or cationic materials.

The material to be electroprocessed can be present in the solution at any concentration that will allow electroprocessing. In one desirable embodiment, the materials to be electroprocessed are present in the solution at concentrations between 0 and about 1.000 g/ml. In another desirable embodiment, the materials to be electroprocessed are present in the solution at concentrations between 0 and about 0.100 g/ml. In another desirable embodiment, the materials to be electroprocessed are present in the solution at concentrations between 0 and about 0.085 g/ml. In another desirable embodiment, the materials to be electroprocessed are present in the solution at concentrations between 0 and about 0.045 g/ml. In another desirable embodiment, the materials to be electroprocessed are present in the solution at concentrations between 0 and about 0.025 g/ml. In another desirable embodiment, the materials to be electroprocessed are present in the solution at concentrations between 0 and about 0.005 g/ml. Examples of desirable embodiments also include, without limitation, those in which the materials to be electroprocessed are present in the solution at concentrations in each of the following ranges: between approximately 0.025 g/ml and approximately 0.045 g/ml; between approximately 0.045 g/ml and approximately 0.085 g/ml; between approximately 0.085 g/ml and approximately 0.100 g/ml; and between approximately 0.100 g/ml; and approximately 1.000 g/ml.

Some specific examples of desirable embodiments include: Type I collagen electrospun from a concentration of approximately 0.083 g/ml in 1,1,1,3,3,3 hexafluoro-2-isopropanol (HFIP); Type III collagen electrospun from a concentration of approximately 0.04 g/ml in HFIP; Type I collagen at a concentration of 0.0393 g/ml in HFIP; a solution containing 0.1155 grams collagen and 0.1234 grams of elastin from ligamentum nuchae in 5 ml HFIP; Type II collagen at a concentration of 0.100 g/ml in HFIP; Type II collagen at a concentration of 0.04 g/ml in HFIP; type I collagen at a concentration of 0.100 g/ml in 2,2,2-Trifluoroethanol (TFE); elastin electrospun from a solution of 70% isopropanol and 30% water containing 250 mg/ml of elastin; A blend of Type I and Type III collagens at a total concentration of about 0.06 g/ml (Type I at 0.08 g/ml and Type III at 0.04 g/ml) in HFIP; blends of elastin and numerous collagen types at a total concentration of 0.075 g/ml; and 5 mg/ml collagen from an aqueous solution electroprocessed in a vacuum chamber.

Methods of Combining Substances with Electroprocessed Materials

Substances can be combined with the electroprocessed collagen by a variety of means. In some embodiments, the substance comprises molecules to be released from or contained within the electroprocessed collagen and other material and is therefore added to or incorporated within the matrix of electroprocessed material. Substances can be mixed in the solvent carriers or solutions of materials for electroprocessing. In this system materials can be mixed with various substances and directly electroprocessed. The resulting composition comprising an electroprocessed matrix and substance can be topically applied to a specific site and the substances released from the material as a function of the material undergoing breakdown in the surrounding environment. Substances may also be released from the electroprocessed compositions of the present invention through diffusion.

The state of the electroprocessed collagen and other electroprocessed material in relation to the incorporated substances is dictated and can be controlled by the chemistry of the system and varies based on the selection of matrix materials, solvent(s) used, and solubility of the matrix materials in those solvents. These parameters can be manipulated to control the release of the substances (or other elements) into the surrounding environment. If substances to be incorporated into the electroprocessed material are not miscible with the material, separate solvent reservoirs for the different components can be used. Thus, substances that are not miscible with collagen solutions can be mixed into solvent carriers for other materials to be electroprocessed along with the collagen from, for example, separate reservoirs. Mixing in such an embodiment occurs prior to, during, and/or after deposition on the target, or a combination thereof. It is to be understood that substances may be entrapped or entangled within an electroprocessed material, bonded to a material before the material undergoes electroprocessing, or bound to specific sites within the matrix material.

In a variation of this embodiment, the substance is a particle or aggregate comprising a matrix of compounds or polymers such as alginate that, in turn, contain one or more compounds that will be released from the electroprocessed material. Substances such as drugs or cells can be combined with alginate by, for example, combining a drug suspension or drug particulate in the alginate in the presence of calcium. Alginate is a carbohydrate that forms aggregates when exposed to calcium. The aggregates can be used to trap drugs. The aggregates dissolve over time, releasing the substances trapped in alginate. The particles, which are then incorporated within the larger electroprocessed matrix, are biologically compatible but relatively stable and will degrade gradually. In some embodiments, the electroprocessed materials resemble a string of pearls. This is a physical aspect of the electroprocessing. If the concentration of materials to be electroprocessed is low, electrospraying of beads occurs. As the concentration increases there are some beads and some fibers. A further increase in concentration of materials to be electroprocessed leads to predominantly or all fibers. Therefore, the appearance of the pearls on a string is a transition phase.

If a substance does not bind or interact with an electroprocessed matrix material, the drug can be entrapped in PGA or PLA pellets or electroaerosoled to produce pellets in the electrospun material. Several drugs (for example, penicillin) can be trapped in this manner. The pellets or electroaerosoled droplets containing the substance begin to dissolve after administration to deliver the entrapped material. Some agents can be coupled to synthetic, or natural polymer by a covalent bond, prior to or after spinning.

In other embodiments, the substance is electroprocessed. Substances can be electroprocessed from the same orifice as the collagen and/or other materials being electroprocessed or from different orifices. Substances can also be subjected to the same or a different type of electroprocessing as the material. A molecule can be bonded to the electroprocessed collagen or other materials in the collagen matrix directly or through linking to a molecule that has an affinity for the material. An example of this embodiment involves bonding polypeptide substances to heparin, which has an affinity for collagen. This embodiment allows release rates to be controlled by controlling the rate of degradation of the material, for example by enzymatic or hydrolytic breakdown.

In other embodiments, the electroprocessed collagen can entrap substance during the electrodeposition process. This can be accomplished by disposing substances in the space between the source of the electroprocessed stream and the target for the electroprocessed material. Placing such substances in the space between the source and target can be accomplished by a number of methods, including, but not limited to, suspending in air or other gases, dripping, spraying, or electroprocessing the substances. The substances can be present in that space in, for example, particulate, aerosol, colloidal, or vapor form. In these embodiments, the electroprocessed material or matrix will physically entrap the substances. This embodiment can also be used to encapsulate larger particles, such as cells, large particles, or tablets. For example, if a tablet is dropped through the matrix as it forms, the tablet is surrounded by the matrix. If a small object, is dropped through the matrix as it forms, or is placed in an aerosol within the matrix, the object may be trapped between filaments, within filaments or attached to the outside of the filaments. For example, by suspending objects in a solution or within a matrix, the objects can become part of an electrospun matrix during fabrication of the filaments. Alternatively, encapsulation can occur by dropping substances onto or through a matrix material stream as a matrix forms. The objects thus become surrounded by a matrix of electroprocessed material. These embodiments can be used to incorporate within a matrix substances that are not soluble and/or are too large to form a suspension in the solvent used for the production of the material. For substances in a mist or vapor form, controlling distribution and composition of substances in the space between the source and target can be used to alter the physical and chemical properties of the electroprocessed material and the pattern of distribution of the substances in the electroprocessed material. For all of the foregoing embodiments, the substances can be placed in the electroprocessed material in capsules, vesicles, or other containments for subsequent release. Since the solvent carrier often evaporates in the electroprocessing technique as the electroprocessed material forms, such as a filament, substances may be placed in the electroprocessed matrix and solvent toxicity is greatly reduced or eliminated.

In many embodiments the substance comprises cells. Cells can be combined with an electroprocessed collagen matrix by any of the means noted above for combining small objects in a matrix. Cells can, for example, be suspended in a solution or other liquid that contains the collagen, disposed in the area between the solutions and target, or delivered to a target or substrate from a separate source before, during, or after electroprocessing. Cells can be dripped through the matrix, onto the matrix as it deposits on the target or suspended within an aerosol as a delivery system for the cells to the electroprocessed material. The cells can be delivered in this manner while the matrix is being formed. As an example, cardiac fibroblasts were suspended in phosphate-buffered saline (PBS) at a concentration of approximately one million cells per milliliter. The suspension of cells was placed within a reservoir of a Paasche air brush. To test the efficacy of using this type of device to deliver cells, the cell suspension was initially sprayed onto a 100 mm culture dish. Some of the cells survived, attached to the dish and spread out over the substratum. In a second trial, the culture dish was located further away from the air brush and the experiment was repeated. Cells were observed on the dish. They appeared to be flattened by the impact and were partially spread out over the surface of the substratum. Culture media was added to the dish and the cells were placed into an incubator. After one hour of culture, the cells were inspected again, and many were found to have spread out further over the substratum. These results demonstrate that a simple airbrush device can be used to place cells into an aerosol droplet and deliver them on demand to a surface or site of interest. Cell viability can be improved by restricting this technique to cells that are resistant to the shear forces produced in the technique, developing a cell suspension with additives that cushions the cells or refining the aerosolizing device to produce a more laminar flow. In addition, directing the cell aerosol into matrix materials as the matrix is forming in the space between the target or mandrel and the source(s) of molecules being electroprocessed produces the effect of cushioning the cells. While not wanting to be bound by the following statement, it is believed that the cells will be trapped in the storm of filaments or other bodies produced by electrospinning or electroprocessing and pulled onto the mandrel. This situation may be less traumatic to the cells than directly spraying the cells onto a solid surface.

In some embodiments, the cells are added either before or at the same time as the collagen, and other materials that are electroprocessed are brought together. In this way, the cells are suspended throughout the three-dimensional matrix.

Cells can be added as the filaments are produced in the space between the target and polymer source. This is accomplished by dripping the cells onto the target, dripping the cells into the electroprocessed collagen matrix as it forms, aerosoling the cells into the collagen matrix or onto the target or electrospraying the cells into the collagen matrix as it condenses and forms near or on the grounded target. In another embodiment, cells are sprayed or dribbled into a forming electroprocessed material or matrix, and are thereby trapped as the electroprocessed material crosses the air gap between the source solutions and target.

An alternative method to deliver cells to electroprocessed collagen involves electroaerosol delivery of the cells. Cells can be deposited by electrostatic spraying at, for example, 8 kV directly onto standard polystyrene culture dishes, suggesting that electrostatic cell spraying is a viable approach. Cardiac fibroblasts in phosphate buffered saline (PBS) have been electroaerosoled up to a 20 Kv potential difference. In another example, Schwann cells (rat) were plated on a PS petri dish by conventional methods after one day. Schwann cells were also electrosprayed onto a PS petri dish with a metal ground plate behind the dish at 10 kV after one day. Both samples grew to almost confluence after one week. The electroaerosol approach provides some distinct advantages. First, the shear forces produced during the delivery phase (i.e. the production of the aerosol) appear to be much less traumatic to the cells. Second, the direction of the aerosol can be controlled with a high degree of fidelity. In essence the cell aerosol can be painted onto the surface of interest. This allows the cell to be targeted to specific sites. In electroaerosol delivery, cells are suspended in an appropriate media (e.g. culture media, physiological salts, etc.) and charged to a voltage, and directed towards a grounded target. This process is very similar to that used in electroprocessing, particularly electrospinning. The produces a fine mist of cells trapped within the droplets as they are produced and directed at the grounded target.

Cells can be delivered using aerosol and electroaerosol techniques onto electroprocessed collagen. The electroaerosol of cells can be delivered in parallel (i.e. alongside) the electroprocessing material or from a separate site. The cells can be delivered to the storm of filaments or particles produced within the air gap in the electrodeposition process or directed at the target. The cells and electroprocessed material also can be delivered in an alternating sequence to the target, i.e. electrodeposit the material, aerosol the cells, electrodeposit the material, aerosol the cells. This allows for the discrete layering of the construct in separate layers. Furthermore, a vapor source can be provided that directs water onto the mandrel of target used to collect the cells. Providing this moisture improves cell viability by keeping the cells from dehydrating during processing. Cells can be added to the electroprocessed collagen at any time or from any orientation in any aerosol strategy. Again the advantage of the process in general is that collagen, for example, collects in a dried state on the target mandrel. Accordingly, although some solvents for collagen may be toxic, they are lost from the system before the filaments collect on the target.

Cells can also be trapped within a carrier prior to producing an aerosol. For example, cells can be encapsulated within a material like alginate. The encapsulated cells are physically protected from shear and trauma during processing. Cells delivered in this form to the electroprocessed material will have higher viability when sprayed or electrostatically seeded.

Electroprocessed collagen can also be delivered directly to a desired location. For example, an electroprocessed material can be produced directly onto a skin wound, with or without substances such as molecules or cells. Additional cells or materials can then be aerosolized onto or into the wound site. Other surgical sites can also be amenable the delivery of materials using various electrodeposition techniques or combinations thereof of these methods.

Magnetically and electrically active materials can be electroprocessed, including, for example, preparing conducting polymer fibers produced by electrospinning. In addition, conducting polymers can be prepared in-situ in the matrix by, for example, incorporation of a monomer (e.g., pyrrole) followed by treatment with polymerization initiator and oxidant (e.g., $FeCl_3$). Finally, conducting polymers can be grown in the material after electroprocessing by using a matrix-coated conductor as the anode for electrochemical synthesis of, for example, polypyrrole or polyaniline. Collagen or other materials to be electroprocessed can be added to an aqueous solution of pyrrole or aniline to create a conducting polymer at the anode with the entrapped electroprocessed material-forming compounds, which can then be treated with other compounds to allow formation of the material to occur.

More than one method for combining the substances with electroprocessed collagen can be used in a single embodiment or application. Combining methods can be especially useful in embodiments in which the electroprocessed collagen will release one or more substances, and even more so when the released substances are intended to have complex release kinetics, although such combinations are not limited to those embodiments.

Shapes of Electroprocessed Materials and Matrices

The present invention also provides a method for manufacturing a collagen-containing extracellular matrix having a predetermined shape. The method includes pre-selecting a mold adapted to make the predetermined shape and filling the mold with collagen or collagen forming molecules using electroprocessing techniques. In other examples of embodiments, the method comprises pre-selecting a mold or mandrel adapted to make the predetermined shape wherein the mold comprises a grounded target substrate and the shape of the matrix is dictated by the outer dimensions of the mandrel. Then, one or more electrically charged solutions comprising collagen, or molecules capable of forming collagen, are streamed onto the grounded target substrate under conditions effective to deposit the collagen on the substrate to form the extracellular matrix having the predetermined shape. The collagen streamed onto the substrate may comprise electrospun fibers or electroaerosol droplets. The formed matrix having a shape of the substrate is then allowed to cure and removed from the mandrel. The substrate can be specifically shaped, for instance in the shape of a nerve guide, skin or muscle patch, fascial sheath, vertebral disc, knee meniscus, ligament, tendon, or a vascular graft for subsequent use in vivo. The collagen matrix can be shaped to fit a defect or site to be filled. For example a site where a tumor has been removed, or an injury site in the skin (a cut, a biopsy site, a hole or other defect) or to reconstruct or replace a missing or shattered piece of bone. Electroprocessing allows great flexibility and makes it possible to customize the construct to virtually any shape needed. Some preferred examples include a cylindrical shape, a flattened oval shape, a rectangular envelope shape (like a mailing envelope), or any other desired shape. Collagen can be formed to virtually any shape. Complex shapes such as chambered organs can be formed. The overall three-dimensional geometric shape of the platform is determined by the ultimate design and type of tissue to be bioengineered.

Several methods exist for preparing a specifically shaped mold. For instance, a particular type of organ or tissue that is desired to be replaced has a specific shape, such as a skin patch to fit a biopsy site or a large scalp area following a wide area removed after discovering a malignant melanoma. That shape is reproduced and created inside a mold designed to mimic that shape.

This mold can be filled by electrodepositing the collagen into the mold. In this way, the collagen matrix exactly mimics the mold shape. Creating an extracellular collagen matrix that has a specific shape can be very important in creating a new organ. The shape of the matrix can induce cells seeded into the collagen matrix to differentiate in a specific manner. Growth factors or other substances may be incorporated as discussed elsewhere herein. This can result in a more effective, more natural-like organ or tissue being created. Hollow matrices to be filled with desirable materials such as cells or to replace hollow organs or structures can also be made. For a cylindrical-shaped bioengineering platform or any other shape of construct in which an enclosed area is desired, a suture, glue, staple or heat seal or some other method may be used to seal one end of the bioengineering platform. This results in a hollow platform that is closed on one end and open on the other. The electrodeposited collagen-containing platform can now be filled with cells or other materials, or cells or other materials may be placed on the outer surface of the construct. For example, a mixture of collagen from the electroprocessing procedure, or other materials such as cells, or molecules such as drugs or growth factors may be placed within the platform. The free and open end of the envelope that was used to fill the construct with material can be sutured, glued or heat sealed shut to produce an enclosed bioengineering platform. Mixing cells with the material during electroprocessing results in cells being distributed throughout the matrix so that they do not have to migrate into the gel. As noted above, however, electroprocessed collagen has been shown to promote infiltration.

Further shaping can be accomplished by manual processing of the formed matrices. For example, multiple formed matrices can be sutured, sealed, stapled, or otherwise attached to one another to form a desired shape. Alternatively, the physical flexibility of many matrices allow them to be manually shaped to a desired structure.

Patterns of Distribution for Electroprocessed Collagen and Other Electroprocessed Materials and Substances Many embodiments of the present invention involve means for manipulating the pattern or distribution of electroprocessed collagen and/or substances within an electroprocessed material. For example, an electroprocessing target can also be specifically charged or grounded along a preselected pattern so that electroprocessed materials streamed toward the target are directed into specific directions or distributions on the target or on a substrate. The electric field can be controlled by a microprocessor to create a matrix having a desired geometry. The target and the electroprocessing nozzle or nozzles can be movable with respect to each other and to the target thereby allowing additional control over the geometry of the electroprocessed material to be formed. In embodiments in which substances are electroprocessed, this manipulation will also allow control of the distribution of substances within the electroprocessed materials. For example an electroprocessed collagen matrix can be prepared on a mandrel, and substances from a separate reservoir can be sprayed, dripped, electroprocessed in a specific pattern over the existing matrix. This may also be accomplished by simultaneously electrospraying a matrix from one source and a substance from another source. In this example the matrix source may be stationary and the substance source is moved with respect to the target mandrel.

Other features that allow establishment of such a pattern include, but are not limited to, the ability to deposit multiple layers of the same or different materials, combining different electroprocessing methods, the use multiple orifices with different contents for electroprocessing, and the existence of numerous methods for combining substances with the materials. For example, a gradient of substances can be created along a electroprocessed material. In embodiments in which the matrix is shaped into a cylindrical construct, for example, the gradient can be prepared along the long axis of a construct (left to right) or the perpendicular axis (inside to out). This configuration is used to provide a chemoattractant gradient to guide the movement of cells within a specified site. Thus, for example, in some embodiments in which neovascular agents are prepared in a perpendicular gradient along a collagen-based construct, the agents can be concentrated on the dorsal surface of a sheet of the material. The ventral side can be placed against a wound and the higher concentration of angiogenic materials on the dorsal surface of the construct will increase the migration of endothelial cells through the electrospun material. Again, embodiments with complex patterns can use a microprocessor programmed with the specific parameters to obtain a specific, preselected electroprocessed pattern of one or more electroprocessed polymers, optionally with one or more substances.

Additional Processing of Electroprocessed Collagen Materials

Electroprocessed collagen and other electroprocessed materials may be further processed to affect various properties. In some embodiments electroprocessed material is cross-linked. In some embodiments, cross-linking will alter, for example, the rate at which the electroprocessed material degrades or the rate at which a substance contained in an electroprocessed matrix is released from the electroprocessed material by increasing structural rigidity and delaying subsequent dissolution of the electroprocessed material. Electroprocessed collagen and other materials are crosslinked simultaneously with their formation by forming them in the presence of cross-linking agents or treated with cross-linking agents after electrodeposition. Any technique known to one of ordinary skill in the art for cross-linking materials may be used. Examples of techniques include application of cross-linking agents and application of certain cross-linking radiations. Examples of cross-linking agents that work with one or more proteins include but are not limited to condensing agents such as aldehydes e.g., glutaraldehyde, carbodiimide EDC (1-ethyl-3(3 dimethyl aminopropyl)), photosensitive materials that cross link upon exposure to specific wavelengths of light, osmium tetroxide, carbodiimide hydrochloride, and NHS (n-hydroxysuccinimide), and Factor XIIIa. Glutaraldehyde is a desirable crosslinking agent for collagen. Ultraviolet radiation is one example of radiation used to crosslink matrix materials in some embodiments. Natural materials can be cross-linked with other natural materials. For example, collagen can be cross-linked and or stabilized by the addition of fibronectin and or heparin sulfate. For some polymers heat can be used to alter the matrix and cross link elements of the matrix by fusing adjacent components of the construct. As another example, collagen may be cross-linked using natural processes mediated by cellular elements. For example, electrospun collagen can be cross-linked by the lysyl oxidase enzymatic cascade. Synthetic polymers may also be partially solubilized to alter the structure of the material, for example brief exposure of some synthetics to alcohols or bases can partially dissolve and anneal adjacent filaments together. Some polymers may be cross-linked using chemical fusion or heat fusion techniques. Synthetic polymers generally can be cross-linked using high energy radiation (e.g., electron beams, gamma rays). These typically work by the creation of free radicals on the polymer backbone which then couple, affording cross links. Backbone free radicals can also be generated via peroxides, azo compounds, aryl ketones and other radical-producing compounds in the presence of heat or light. Reduction-oxidation reactions that produce radicals (e.g., peroxides in the presence of transition metal salts) can also be used. In many cases, functional groups on polymer backbones or side chains can be reacted to form cross-links For example, polysaccharides can be treated with diacylchlorides to form diester cross-links. Cross-linking may also occur after application of a matrix where desirable. For example, a matrix applied to a wound may be cross-linked after application to enhance adhesion of the matrix to the wound.

One preferred crosslinking agent for electroprocessed collagen is glutaraldehyde. In some embodiments using a Type I collagen/Type III collagen/elastin (45:35:20) matrix, exposing the matrix to glutaraldehyde vapor under appropriate conditions for at least about 10 minutes provided a satisfactory degree of cross-linking. In general longer intervals of glutaraldehyde cross-linking increase the stability of the matrix, but reduce cellular infiltration. A desirable range is exposure for between about 10 and about 20 minutes. Exposure was accomplished by preparing a gas chamber made by placing a sterile 10 cm$^2$ petri dish with its top removed into the center of a 35 cm$^2$ petri dish with its top remaining Approximately 4 ml of the 3% glutaraldehyde solution was placed into the smaller dish and the collagen mats were placed in the in the larger dish toward the edges. The 3% glutaraldehyde solution was made by mixing 50% glutaraldehyde with distilled water and 0.2 M sodium cacodylate buffer.

In some embodiments in which crosslinking involves the use of crosslinking agents having aldehyde groups, crosslinking may be followed by treatment with materials for the purpose of blocking unreacted aldehyde groups. Examples include, but are not limited to, treatment with glycine (for example a 0.01 to 0.1 Molar solution) or treatment with protein compositions such as bovine serum albumin or milk powder.

Additional substances can be applied to the electroprocessed material after formation, for example by soaking the electroprocessed material in the substance or a solution containing the substance or by spraying the solution or substance onto the electroprocessed material. Collagen matrices placed in contact with cells in vitro or in vivo, will be infiltrated by cells migrating into the matrix. Any in vitro method for seeding matrices with cells can be used. Examples include for example, placement in a bioreactor or use of electrostatic cell seed techniques such as those disclosed in U.S. Pat. No. 6,010,573 to Bowlin et al., U.S. Pat. No. 5,723,324 to Bowlin et al., and U.S. Pat. No. 5,714,359 to Bowlin et al. Electroprocessed matrices may also be sterilized using known sterilization methods. For example the electroprocessed material can be immersed in a 70% alcohol solution. Another preferred sterilization method is the peracetic acid sterilization procedure known for collagen-based tissues.

Physical processing of the formed electroprocessed material is also possible. The electroprocessed matrix may be milled into a powder or milled and prepared as a hydrated gel composed of banded fibrils. In some embodiments, mechanical forces, such as compression, applied to an electroprocessed material hasten the breakdown of the matrix by altering the crystalline structure of the material. Structure of the matrix is thus another parameter that can be manipulated to affect release kinetics. Polyurethanes and other elastic materials such as poly(ethylene-co-vinyl acetate), silicones, and polydienes (e.g., polyisoprene), polycaprolactone, polyglycolic acid and related polymers are examples of materials whose release rate can be altered by mechanical strain.

In some embodiments, an electroprocessed material is treated with ammonia vapors for varying lengths of time to control the physical state and porosity of the matrix. In one embodiment, a brief exposure (less than 1 hour) of an electrospun matrix to ammonia vapors anneals or cross-links the fibers of a matrix composed of electrospun collagen or gelatin together. Longer exposure to ammonia vapors results in the melding of the matrix into a more film-like or sheet-like structure. In some embodiments, this processing method is used to trap substances within an electrospun matrix. In one embodiment, substances that cannot be electroprocessed along with the collagen because they are too large or otherwise not compatible with the solvents used in electroprocessing are applied in a dry state to a dry electrospun matrix of collagen. Treating the matrix with ammonia alters the filaments and melds or crosslinks them together. This results in the physical trapping of the substances within the matrix. In some embodiments, a brief ammonia treatment is used to capture the material and bind it to the surface. In other embodiments, a longer treatment incorporates the material within the electroprocessed materials. In some embodiments, this method is used to develop an antigen delivery device in which antigens of interest are trapped within the matrix for delivery. In other embodiments, this processing is used to control the porosity of the matrix or to shape the material around objects with complex shapes.

Further Processing of Engineered Tissues Containing Electroprocessed Collagen

Once the electroengineered tissue containing electroprocessed collagen and cells is assembled, the tissue can be inserted into a recipient. Alternatively, the structure can be placed into a culture to enhance the cell growth. Different types of nutrients and growth factors can be added to a culture (or administered to a recipient) in order to promote a specific type of growth of the engineered tissue. In one example, specifically in connection with the preparation of an engineered muscle tissue, the electroengineered tissue containing collagen and cells can be mechanically or passively strained or electrically preconditioned (stimulating electrically sensitive cells, such as cardiac and skeletal muscle cells to contract by electrical depolarization) in order to stimulate the alignment of cells to form a more functional muscle implant. Applying strain also increases the tensile strength of the implant. For example, forceful contraction or stretching of cells will lead to hypertrophy as if they were subjected to stretch. In a skin patch, application of mechanical stress may facilitate orientation of the skin for use in an area such as the scalp that is exposed to significant stretching force. Other tissues that may benefit from the application of strain include, but are not limited to, muscle tissues, ligament tissues, and tendon tissues. Passive strain in this context refers to a process in which strain is induced by the cells themselves as they contract and reorganized a matrix. This is typically induced by fixing the ends of the electroengineered collagen matrix. As the cells contract and alter the matrix the fixed ends of the matrix remain in place and thereby strain the cells as they "pull" against the isometric load. The strain not only aligns the cells, it sends signals to them with respect to growth and development. The construct can also be strained externally, i.e. the construct can be prepared and then stretched to cause mechanical alignment. Stretch is typically applied in gradual fashion over time. The collagen can also be stretched to cause alignment in the matrix before the cells are added to the construct (i.e. form the matrix, stretch the matrix and then add the cells). Any known method for applying mechanical or passive physical strain to tissues may be used.

An additional way to combine electroprocessed collagen matrices with cells for implantation is to prepare constructs, then add cells to the constructs. Cells can be placed in a lumen or space within a construct, or implanted adjacent to the implant to facilitate growth. Alternatively, the implant can be placed in a bioreactor. There are several kinds of commercially available bioreactors, devices designed to provide a low-shear, high nutrient perfusion environment. Until recently, most of the available bioreactors maintained cells in suspension and delivered nutrients and oxygen by sparging, through the use of impellers, or other means of stirring. These methods produce high shear environments that can damage cells or inhibit the formation of large-scale constructs. The RCCS bioreactor (Synthecon) is a rotating wall bioreactor. It consists of a small inner cylinder, which itself can be used as a substrate for electroprocessing, positioned inside a larger outer cylinder. Although the electrospun or electroaerosol matrix can be fabricated on the inner cylinder, other locations within the bioreactor also can be used for placement of a matrix for seeding. The gap between the inner and outer cylinders serves as the culture vessel space for cells. Culture medium is oxygenated via an external hydrophobic membrane. The low shear environment of the Synthecon RCCS bioreactor promotes cell-cell and cell-extracellular matrix (ECM) interactions without the damage or "washing away" of nutrients that occurs with active stirring or sparging. Typically, the RCCS device is operated at rotation rates of 8 up to 60 rpm, as required to maintain cells in suspension, and at less than 8 rpm (preferably 2-3 rpm) for cultures immobilized along the center shaft of the vessel. The Synthecon bioreactor can be used in a standard tissue culture incubator. These values for spin rates and other parameters can be varied depending on the specific tissue created.

In other applications an electrospun construct may be fabricated and placed within the RCCS bioreactor and allowed to undergo continuous free fall, a buoyant environment that fosters the formation of large scale, multi-layered constructs. Cells may be added to the construct prior to its placement within the bioreactor. Alternatively, the bioreactor may be used as a platform to seed cells onto the electrospun matrix. For example, a cylindrical construct can be placed within the bioreactor vessel. Cells may be added to the vessel and allowed to interact with the electrospun construct in free fall. The rate required to maintain the constructs in suspension is dependent upon the size and density of the material present in the construct. Larger constructs (2-4 mm in diameter by 10-12 mm in length may require rates of rotation that approach 15-20 rpms. Larger constructs, for example cartilage, can require even higher rates of rotation.

Electroprocessed collagen materials, such as matrices, are useful in formation of prostheses. One application of the electroprocessed matrices is in the formation of medium and small diameter vascular prostheses. An example of a small diameter prosthesis is one having an inner diameter less than six millimeters, for example, a diameter of four millimeters. Some preferred materials for this embodiment are collagen and elastin, especially collagen type I and collagen type III. Some examples include, but are not limited to coronary vessels for bypass or graft, femoral artery, popliteal artery, brachial artery, tibial artery, radial artery, arterial bifurcation, or corresponding veins. The electroprocessed material is useful especially when combined with endothelial cells on the inside of the vascular prosthesis, and smooth muscle cells, for example a collagen tube, and also when combined with fibroblasts on the outside of the collagen tube. In some embodiments, such vessels are made using electrospun collagen fibers (for example, 50-250 nm diameter collagen fibers) as scaffolding, arterial cellular components (e.g. smooth muscle cells, fibroblast cells, and endothelial cells), collagen fiber encapsulation matrix (e.g., collagen gel or an electroprocessed matrix), and fibronectin. In some preferred embodiments, such prosthetics are comparable, compositionally and mechanically (e.g., burst strength and suture retention), to a native small caliber blood vessel and exhibit an in vivo performance of the tissue engineered vascular construct that is equivalent or similar to that of an autologous arterial prosthetic of an equal inner diameter. In other embodiments, such vessels are used clinically and for research purposes as models for blood vessels and vascular prosthetics. More complicated shapes including tapered and/or branched vessels can also be constructed. In some embodiments, larger diameter fibers, including but not limited to collagen fibers, are wound around the prosthesis. Examples include fibers such as those used in prostheses disclosed in U.S. patent application Ser. No. 09/512,081. A different shaped mandrel is used in some embodiments to wind the large fibers around or to orient the electrospun/electroaerosol polymer.

Combination of electroprocessed collagen and other fibers, such as larger diameter (e.g., 50 to 200 μm) collagen or other fibers can provide optimal growth conditions for cells. The large diameter fibers form a basic structural matrix that lends mechanical support to the construct, and the electroprocessed matrix is used as a scaffolding to deliver and/or support the cells. This facilitates cell attachment onto the structural matrix. Large scale collagen fibers can be incorporated into other bioengineered organs and tissues to lend additional mechanical strength as needed. For example, large fibers can be placed within an electrospun matrix that is designed as a scaffolding for the fabrication of skeletal muscle, cardiac muscle and other smooth muscle based organ such as the intestine and stomach. In an alternative fabrication strategy, a cylindrical construct is electrospun onto a suitable target, for example a cylindrical mandrel. Other shapes can be used if desirable based upon the shape of the site into which the implant will be placed. Matrices in this embodiment include electroprocessed collagen and other components, for example fibrin, PGA, PLA, and PGA-PLA blends, PEO, PVA or other blends. The relative ratio of the different components of this construct is tailored to specific applications (e.g. more fibrin, less collagen for enhanced vascularization in a skin graft). To fabricate a cylindrical muscle the construct is filled with muscle or stem cells or other cell type and the distal ends of the electrospun constructs are sutured or sealed shut. In some embodiments, cells are mixed with various matrix materials to enhance their distribution within the construct. For example, the cells can be mixed with electroprocessed collagen, and optionally fibrin, prior to insertion into the construct. The objective of this strategy is to provide additional mechanical support to the construct and provide the cells with a three dimensional matrix within the construct to promote growth. This also helps to maintain the cells in an even distribution within the construct. This method can be used to enhance the alignment of the cells within the construct. This filling material can be extruded directly into the cylindrical construct, as the filling is extruded, alignment occurs. Mixing endothelial cells with the other cells inserted into the construct (or other cell types) is done to accelerate neovascularization. Another method to accomplish this objective is to electrodeposit endothelial cells directly into the electroprocessed collagen matrix that aids in formation of the cylindrical sheath. The alignment of the fibers within the electroprocessed matrix that comprises the construct are optionally controlled by controlling the relative movement of the target and source solution with respect to one another. Other cell types, such as tendon fibroblasts, are optionally electrospun into or onto the outer surface of the construct to enhance the formation of the outer connective tissue sheath that forms the construct.

In another example, a sheet of electroprocessed collagen material is prepared, rolled into a cylinder and inserted into an electroprocessed cylinder. The construct is filled with cells as described above, sutured shut and placed in a bioreactor or directly in situ. By aligning the fibrils of the electrospun sheet of material in parallel with the long axis of the outer cylinder a scaffolding for the production of a muscle-like, electroprocessed composition is produced. Cells in contact with the fibrils that are arrayed along the long axis of the sheet spread in parallel with the fibrils of the sheet, forming a muscle construct of cells arrayed and layered in a pattern of organization similar to that present in vivo. This basic design can be adapted to produce many different tissues, including but not limited to skeletal muscle and cardiac muscle. The cylindrical tissue construct is then implanted or placed within a RCCS bioreactor. Rates of rotation to maintain this type of construct in suspension range from 4-20 rpm, depending upon the over mass of the tissue and the specific materials used to fabricate the outer cylinder.

Vascularization of the engineered tissue containing matrices of electroprocessed collagen, either alone or with other materials, occur in situ several days after surgery. In some embodiments, neovascularization of an engineered construct containing electroprocessed material is enhanced by mixing endothelial cells into the construct during fabrication. Another alternative for supplying engineered tissue containing electroprocessed material with a vascular supply is to temporarily transplant the tissue into the omentum. The omentum has an extensive and rich vascular supply that can be used like a living incubator for the support of engineered tissue. The engineered tissue is removed from a bioreactor, wrapped in the omentum and supported by the diffusion of nutrients and oxygen from the surrounding tissue in the omentum. Alternatively, or in addition to this approach, engineered tissue is connected directly to the endogenous vascular supply of the omentum. A blood vessel can be partially perforated or cut or left dissected free of the omentum. The engineered tissue containing electroprocessed collagen, fibrin, or other materials, depending upon the construct, is wrapped around the vessel. The engineered tissue is supported by nutrients leaking from the perforated vessel or by the simple diffusion of nutrients if the vessel is left intact. Regardless of strategy, the engineered tissue is surrounded by the omentum and its rich vascular supply. This procedure can be performed using blood vessels outside the omentum.

Tissue containing electroprocessed collagen, and optionally other material, can be engineered with an endogenous vascular system. This vascular system can be composed of artificial vessels or blood vessels excised from a donor site on the transplant recipient. The engineered tissue containing electroprocessed matrix material is then assembled around the vessel. By enveloping such a vessel with the tissue during or after assembly of the engineered tissue, the engineered tissue has a vessel that can be attached to the vascular system of the recipient. In this example, a vessel in the omentum, or other tissue is cut, and the vessel of the engineered tissue is connected to the two free ends of the omental vessel. Blood passes from the omental vessel into the vascular system of the engineered tissue, through the tissue and drains back into the omentum vessel. By wrapping the tissue in the omentum and connecting it to an omental blood vessel, the engineered tissue is supported by the diffusion of nutrients from the omentum and the vessel incorporated into the tissue during its fabrication. After a suitable period of time the tissue is removed from the omentum and placed in the correct site in the recipient. By using this strategy the engineered tissue containing electroprocessed material is supported in a nutrient rich environment during the first several days following removal from the bioreactor. The environment of the omentum also promotes the formation of new blood vessels in implanted tissue. This omental incubator strategy can be combined with the other strategies such as combining angiogenic factors in the matrix material during electroprocessing.

Several options are available. For example, the implants can be seeded with angioblasts and/or endothelial cells to accelerate the formation of vascular elements once the engineered tissue is placed in situ. As another example, angiogenic peptides can be introduced into the engineered tissue via an osmotic pump. Combinations of methods can also be used. The use of an osmotic pump permits delivery of peptides or, as noted, angiogenic peptides or growth factors directly to the site of interest in a biologically efficient and cost-effective manner. VEGF delivered to ischemic hind limbs of rabbits accelerated capillary bed growth, increased vascular branching and improved muscular performance with respect to ischemic controls. An alternative approach is to seed fully differentiated tissue constructs containing electroprocessed matrix material with additional endothelial cells and or angioblasts shortly before they are implanted in situ.

In some embodiments, the stem cells or other cells used to construct the implant are isolated from the subject, or other compatible donor requiring tissue reconstruction. This provides the advantage of using cells that will not induce an immune response, because they originated with the subject (autologous tissue) requiring the reconstruction. Relatively small biopsies can be used to obtain a sufficient number of cells to construct the implant. This minimizes functional deficits and damage to endogenous tissues that serve as the donor site for the cells.

In some embodiments, the electroprocessed collagen matrices of the present invention include substances in the matrix that will improve the performance of the implanted electroprocessed matrix. Examples of substances that can be used include peptide growth factors, antibiotics, and/or anti-rejection drugs, anesthetics, analgesics and or anti-inflammatory agents. Alternatively, cells that are engineered to manufacture desired compounds can be included. The entire construct is, for example, cultured in a bioreactor or conventional culture or placed directly in vivo. For example, neovascularization can be stimulated by angiogenic and growth-promoting factors, administered as peptides, proteins or as gene therapy. Angiogenic agents can be incorporated into the electroprocessed matrix. Nerve growth factors can be incorporated into the matrix to promote growth or neurons into the matrix and tissue. Various methods can be used to control the release of these factors to the implantation environment. In a degradable matrix, the gradual degradation/breakdown of the matrix will release these factors and accelerate growth of desired tissues.

Electroprocessed collagen matrices can also be used in connection with other matrix building processes. In other words, an extruded tube can have an outside layer electrospun onto it wherein the different layers complement each other and provide an appropriate matrix to promote a specific type of cell growth. As an example, a vascular graft comprised primarily of a collagen tube can have an electrospun layer of both collagen and cells added to promote the acceptability of the graft in a particular recipient. A second example is an in vitro skin preparation formed by growing fibroblasts in one layer, covering the first layer with electroprocessed collagen, and then growing a second layer composed of epidermal cells in the fibrin matrix. This layering technique can be used to make a variety of tissues.

Uses for the Compositions of the Present Invention

The electroprocessed collagen compositions of the present invention have a broad array of potential uses. Uses include, but are not limited to, manufacture of engineered tissue and organs, including structures such as patches or plugs of tissues or matrix material, prosthetics, and other implants, tissue scaffolding, repair or dressing of wounds, hemostatic devices, devices for use in tissue repair and support such as sutures, surgical and orthopedic screws, and surgical and orthopedic plates, natural coatings or components for synthetic implants, cosmetic implants and supports, repair or structural support for organs or tissues, substance delivery, bioengineering platforms, platforms for testing the effect of substances upon cells, cell culture, and numerous other uses. This discussion of possible uses is not intended to be exhaustive and many other embodiments exist. Furthermore, although many specific examples are provided below regarding combination of collagen with other electroprocessed materials and/or specific substances, many other combinations of materials and substances may be used.

Use of Electroprocessed Composition as Tissue or Organ Augmentation or Replacement The ability to combine cells in an electroprocessed collagen material provides the ability to use the compositions of the present invention to build tissue, organs, or organ-like tissue. Cells included in such tissues or organs can include cells that serve a function of delivering a substance, seeded cells that will provide the beginnings of replacement tissue, or both. Many types of cells can be used to create tissue or organs. Stem cells, committed stem cells, and/or differentiated cells are used in various embodiments. Examples of stem cells used in these embodiments include, but are not limited to, embryonic stem cells, bone marrow stem cells and umbilical cord stem cells used to make organs or organ-like tissue such as livers or kidneys. In some embodiments the shape of the electroprocessed composition helps send signals to the cells to grow and reproduce in a specific type of desired way. Other substances, for example differentiation inducers, can be added to the electroprocessed matrix to promote specific types of cell growth. Further, different mixtures of cell types are incorporated into the composition in some embodiments. The ability to use electroprocessed collagen materials and matrices to bioengineer tissue or organs creates a wide variety of bioengineered tissue replacement applications. Examples of bioengineered components include, but are not limited to, bone, dental structures, joints, cartilage, (including, but not limited to articular cartilage), skeletal muscle, smooth muscle, cardiac muscle, tendons, menisci, ligaments, blood vessels, stents, heart valves, corneas, ear drums, nerve guides, tissue or organ patches or sealants, a filler for missing tissues, sheets for cosmetic repairs, skin (sheets with cells added to make a skin equivalent), soft tissue structures of the throat such as trachea, epiglottis, and vocal cords, other cartilaginous structures such as articular cartilage, nasal cartilage, tarsal plates, tracheal rings, thyroid cartilage, and arytenoid cartilage, connective tissue, vascular grafts and components thereof, and sheets for topical applications, and repair to or replacement of organs such as livers, kidneys, and pancreas. In some embodiments, such matrices are combined with drug and substance delivery electroprocessed matrices of the present invention in ways that will improve the function of the implant. For example, antibiotics, anti-inflammatories, local anesthetics or combinations thereof, can be added to the matrix of a bioengineered organ to speed the healing process and reduce discomfort.

Electroprocessed collagen matrices have a number of orthopedic applications. Bone can be made by combining electroprocessed collagen with, for example, osteoblasts, and bone growth factors. In some embodiments, the matrix can also contain a conductive material to allow application of a current to an implantation site to facilitate growth and healing. Optionally, the collagen may be genetically engineered to contain more P-15 sites than in naturally occurring collagen to accelerate production of hydroxyapatite. Such bone prosthetics can be used, for example, in joint repair and replacements, such as hip replacements, or to replace lost or deteriorated bone tissue. Cartilage may be engineered by combining Type II collagen with chondroblasts and other matrix materials such as proteoglycans. In some embodiments, synthetic versions of hyaluronic acid that are not subject to breakdown are used to promote hydration of the engineered tissue. Optionally, angiogenic inhibitors can be included in the matrix to prevent neovasculogenesis in the cartilage. Such engineered cartilage may be used, for example, in spinal disc repair or replacement, reconstruction of a cardiac fibrous skeleton, nose or ear replacement or augmentation, or hip joint repair. The matrices can also be used to engineer dentin by, for example, incorporating dentinoblasts into the matrix. Ligaments (including, for example, knee menisci, patellar ligaments, collateral ligaments, cruciate ligaments, rotator cuff, and acetabular labrum of the hip joint), may be prepared using fibroblasts in a matrix of elastin and collagen. In some embodiments, an extruded central core is prepared and modified by ammonia driven fibrillogenesis. Electroprocessed matrices may then be applied to the outer surface. Alternatively, the entire ligament can be formed with electroprocessing. Optionally, a slight twist can be created by such means as a rotating nozzle or air vortex. In some embodiments, a patient's damaged ligament can be ground up in a crude mixture then sprayed as a new ligament, allowing use of autologous tissue. Tendons (including for example, rotator cuff, achilles tendons, and chordae tendineae), and muscles may also be prepared using the appropriate combination of cells and matrix materials. Tendon and muscle combinations are also possible. In some joint replacement applications, synthetic implants may be coated with engineered tissue to improved compatability of the implant. In embodiments in which growth of bone and/or cartilage into the joint is undesirable, the matrix may be engineered to contain agents that will inhibit growth.

In some embodiments electroprocessing is used to prepare a cartilage construct with an inner central domain composed of random arrays of collagen fibrils. This inner domain is supplemented, for example, with substances such as glycosaminoglycans, hyaluronic acid, keratan sulfate, chondroitin sulfate, and aggrecan complexes to promote hydration. The outer layers are composed of relatively pure collagen electrospun along a desired and predetermined axis.

In neurological applications, the matrices can be used, for example, in the manufacture of nerve guides, dural patches, sealants for damaged nerves, brain constructs as a filler for damaged/removed areas of the brain that are lost during accident or disease, and as "dural" or "arachnoid" patches for cerebrospinal fluid leaks. Optionally, stem cells and nerve growth factors may be included in the matrix. The constructs also can be supplemented with myelinating cells. In some neurological embodiments, it is desirable to use a layer of PGA in or on the construct to limit cellular infiltration and minimize or avoid fibrosis.

Figure 6:
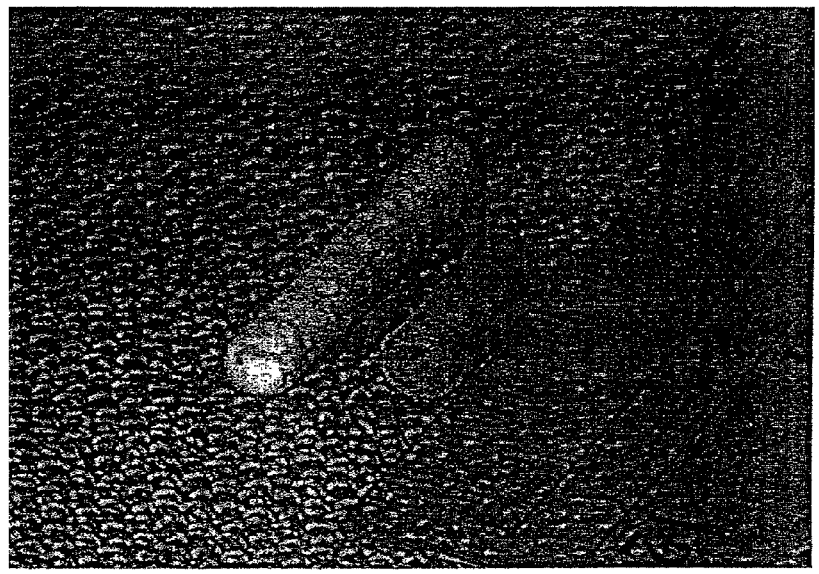
FIG. 6. Example of an electrospun matrix prior to cell seeding (left) and an arterial segment developed from the scaffolding (right).

In cardiovascular applications, the matrices can be used, for example to manufacture stents or to coat stents comprised of synthetic material, thus providing a hybrid stent comprising a synthetic material surrounded by natural material. The natural material may contain, for example, collagen and smooth muscle cells. Optionally, DNA vectors may be placed in such a matrix so that it is taken up by cells that migrate or are seeded into the matrix upon reorganization of the scaffolding. Matrices can be fabricated into, for example, heart valves, valve leaflets, and prosthetic blood vessels for use as, for example, coronary artery bypass grafts. In many embodiments, vascular prosthesis are prepared in "simulated microgravity" in a bioreactor using electroprocessed matrix materials. For example, FIG. 6 is a photograph of an electrospun matrix prior to cell seeding (left) and an arterial segment developed from the scaffolding (right). This approach provides a method to seed the constructs with cells in a low shear environment that provides high nutrient delivery. In some of these embodiments, endothelial cell linings are seeded on the cell creating an implant with the layering structure characteristic of natural vessels. The endothelial lining prevents clotting and blockage of small diameter arteries. Matrices are also used to replace heart muscle damaged or infracted. Patches can be prepared of cardiac muscle. Alternatively, it has been observed that smooth muscle cells implanted upon a heart will transform to cardiac muscle. In some embodiments, matrices used as cardiac muscle patches include vascular endothelial growth factor to allow for vascularizaton of the new tissue. Optionally, nerve growth factor is included to cause innervation of the tissue so that contraction of the new tissue will become coordinated with other heart muscle. Cardiac muscle patches can also be prepared with desired growth factors but no cells. Cardiac valves can be assembled using electroprocessed collagen with or without cells. The valve is assembled in vitro, for example in a bioreactor, for valve leaflet preconditioning. In some embodiments, a ring around the edge is thickened to mimic the structure of a natural valve and to provide a means of attachment and structural support.

The matrices also have numerous uses in skin and cosmetic applications involve facial muscle and connective tissue. Matrices may be used as dressing for wounds or injuries of any type, include, without limitation, dermabrasions and chemical peels. Such matrices can be include electroprocessed with fibrin to add a hemostatic function and promote healing. Matrix materials can also be injected as filler for wrinkles, scars, or defects. Stem cells, fibroblasts, epithelial cells, and/or endothelial cells may be included to provide for tissue growth. Adding such plugs of tissue will reduce scarring. Matrices may also be used to prepare living augmentation, repair and contouring for tissues such as lips, ear drums, corneas, eyelid tarsal plates, foreheads, chins, cheeks, ears, nose, and breasts. Use of the matrices may be combined with other methods of treatment, repair, and contouring. For example, collagen matrix injections can be combined with Botox (Botulinum toxins) for treatment of wrinkles. Matrices can also be shaped to serve as slings to support sagging necks and sagging cheeks.

Electroprocessed collagen matrices can also be used to manufacture prosthetic organs or parts of organs. Mixing of committed cell lines in a three dimensional electroprocessed matrix can be used to produce structures that mimic complex organs. The ability to shape the matrix allows for preparation of complex structures to replace organs such as liver lobes, pancreas, other endocrine glands, and kidneys. In such cases, cells are implanted to assume the function of the cells in the organs. Preferably, autologous cells or stem cells are used to minimize the possibility of immune rejection. Alternatively, cells can be placed in matrix with a pore size that is small enough to shield the cells from immune surveillance while still allowing nutrients to pass to the cells.

In some embodiments, matrices are used to prepare partial replacements or augmentations. For example, in certain disease states, organs are scarred to the point of being dysfunctional. A classic example is hepatic cirrhosis. In cirrhosis, normal hepatocytes are trapped in fibrous bands of scar tissue. In one embodiment of the invention, the liver is biopsied, viable liver cells are obtained, cultured in an electroprocessed matrix, and re-implanted in the patient as a bridge to or replacement for routine liver transplantations.

In another example, by growing glucagon secreting cells, insulin secreting cells, somatostatin secreting cells, and/or pancreatic polypeptide secreting cells, or combinations thereof, in separate cultures, and then mixing them together with electroprocessed materials through electroprocessing, an artificial pancreatic islet is created. These structures are then placed under the skin, retroperitoneally, intrahepatically or in other desirable locations, as implantable, long-term treatments for diabetes.

In other examples, hormone-producing cells are used, for example, to replace anterior pituitary cells to affect synthesis and secretion of growth hormone secretion, luteinizing hormone, follicle stimulating hormone, prolactin and thyroid stimulating hormone, among others. Gonadal cells, such as Leydig cells and follicular cells are employed to supplement testosterone or estrogen levels. Specially designed combinations are useful in hormone replacement therapy in post and perimenopausal women, or in men following decline in endogenous testosterone secretion. Dopamine-producing neurons are used and implanted in a matrix to supplement defective or damaged dopamine cells in the substantia nigra. In some embodiments, stem cells from the recipient or a donor can be mixed with slightly damaged cells, for example pancreatic islet cells, or hepatocytes, and placed in an electroprocessed matrix and later harvested to control the differentiation of the stem cells into a desired cell type. In other embodiments thyroid cells can be seeded and grown to form small thyroid hormone secreting structures. This procedure is performed in vitro or in vivo. The newly formed differentiated cells are introduced into the patient. Numerous other embodiments exist. Collagen is an extremely important structural element and numerous anatomical elements and structures can be made, repaired or augmented using the matrices of the present invention. Several types of implants can be prepared using information regarding tissue structure, histology, and molecular composition, all of which is available to persons of ordinary skill in the art.

Other Uses in Medical Devices and Procedures

Other uses for electroprocessed collagen construct include an obstruction or reinforcement for an obstruction to a leak. For example, electroprocessed collagen matrices can be used to seal openings in lungs after lung volume reduction (partial removal). This use is important not only for hemostatic purposes but also to prevent air leaking into the pleural cavity and pneumothorax. Electroprocessed collagen can also be formed in a sleeve to use as reinforcement for aneurysms or at the site of an anastamosis. Such sleeves are placed over the area at which reinforcement is desired and sutured, sealed, or otherwise attached to the vessel. Matrices can also be used as hemostatic patches and plugs for leaks of cerebrospinal fluid. Yet another use is as an obstruction of the punctum lacryma for a patient suffering from dry eye syndrome. Another use is as a fertility method by injecting a matrix into a duct or tube such as the vas deferens or uterine tube.

Matrices can also be used to support or connect tissue or structures that have experienced injury, surgery, or deterioration. For example, matrices can be used in a bladder neck suspension procedure for patients suffering from postpartum incontinence. Rectal support, vaginal support, hernia patches, and repair of a prolapsed uterus are other illustrative uses. The matrices can be used to repair or reinforce weakened or dysfunctional sphincter muscles, such as the esophageal sphincter in the case of esophageal reflux. Other examples include reinforcing and replacing tissue in vocal cords, epiglottis, and trachea after removal, such as in removal of cancerous tissue.

Several uses are possible in the field of surgical repair or construction. For example, matrices of the present invention are also be used to make tissue or orthopedic screws, plates, sutures, or sealants that are made of the same material as the tissue in which the devices will be used. In some embodiments, applying an electroprocessed matrix directly to a site in the body of an organism is used to attach or connect tissues in lieu of other connection devices.

The invention also includes methods of inducing, promoting, inhibiting, regulating, or otherwise affecting a biological activity using materials comprising electroprocessed collagen. Examples disclosed herein include inducing cell migration by chondrocytes. However, methods of affecting any type of biological activity are within this invention. Activities can be affected by, for example, contacting the cells with an electroprocessed material comprising electrospun collagen fibers. "Contacting" the cells with the electroprocessed material can be accomplished by any means capable of placing the under conditions that will allow interaction between the electroprocessed material and the cells. Examples include, but are not limited to, seeding the cells upon electroprocessed material, applying the cells to the electroprocessed material by spraying or dripping the cells onto the electroprocessed material or the electroprocessing target, electroprocessing the cells, implanting the electroprocessed material, and applying the electroprocessed material to existing tissues or other preparations or compositions containing cells.

Theories have been discussed regarding the possible mechanism(s) for relationship(s) between electrospun collagen and regulation of certain biological activities. It is to be understood that these theories are not intended to be limiting and any effect upon any biological activity resulting from use of electroprocessed collagen is considered to be within this invention, regardless of the cause or mechanism of that effect. Thus, the invention includes, but is not limited to, methods of regulating activity that rely in whole or in part upon, for example, the presence of other substances and/or other electroprocessed materials along with or instead of collagen, the use of collagen containing a specific amino acid sequence, and/or the presence of one or more side chains on the collagen, or other derivatives of collagen. The presence of other materials in the electroprocessed material can be due, for example, to the presence of those materials in a natural collagen source, the addition of those materials to the collagen solution to be electrospun, addition of those materials to the matrix during or after electrospinning, or the formation of those substances due to any aspect of the electrospinning process or the preparation for that process.

Diagnostic and Research Uses

The electroprocessed collagen constructs of the present invention also permit the in vitro culturing of cells for study. The ability to mimic extracellular matrix and tissue conditions in vitro provides a new platform for study and manipulation of cells. In some embodiments, selected cells are grown in the matrix and exposed to selected drugs, substances, or treatments. For example, a culture using a cancer patient's tumor cells can be used to identify in vitro susceptibility to various types of chemotherapy and radiation therapy. In this way, alternative chemotherapy and radiation therapy treatments is analyzed to calculate the very best treatment for a specific patient. For instance, an engineered tissue can be manufactured that includes collagen and cancer cells, preferably a patient's own cancer cells. Multiple samples of this tissue can then be subjected to multiple different cancer therapies. The results from different treatments can then be directly compared to each another for assessment of efficacy.

Another use of electroprocessed collagen matrices is as a bioengineering platform for manipulation of cells in vitro. This application is similar to the use as a platform for research and testing in that it provides for placement of cells in a matrix and treating the cells to engineer them a specific way. For example, stem cells can be placed in a matrix under conditions that will control their differentiation. Differentiation is controlled through the use of matrix materials or substances in the matrix that will influence differentiation. For example, agents, such as retoinic acid, that play a role in promoting differentiation might be placed within the matrix. In other embodiments, gene sequences that are associated with the differentiation process might be electrospun into the matrix. For example, when the transcription factor MYO D is transfected into fibroblasts or stem cells the transfected cells begin to initiate the expression of muscle specific gene sequences and the differentiation of the cells into skeletal muscle. The P15 site of Type I collagen is associated with the induction of bone specific gene sequences.

The invention further includes methods of inducing cell differentiation. In some embodiments, electroprocessed collagen is used to induce cell differentiation. For example, many types of cells differentiate when seeded upon appropriate electrospun collagen fibrous matrices, preferably matrices in which the fibers display the banding pattern characteristic of native collagen. Embodiments exist with any type of cell. Preferred examples include osteoblasts, satellite muscle cells, myoblasts, cardiac stem cells, embryonic stem cells, mesenchymal stem cells, chondrocytes, bone marrow derived stem cells, and cells for which behavior and differentiated can be regulated by including appropriate materials or substances in the matrix.

Compositions of the present invention are also useful for testing and applying various gene therapies. By working with the compositions in vitro, different types of gene therapy and manipulation can be achieved by inserting preselected DNA in suspensions of cells, materials, etc. For example, nonviral techniques such as electroporation are used to treat cultured cells prior to insertion into the matrix of the present invention. In other embodiments, cells are treated within the matrix before the composition is inserted into a recipient. In vitro gene transfer avoids the exposure of a recipient to viral products, reduces risk of inflammation from residual viral particles and avoids the potential for germ cell line viral incorporation. It avoids the problem of finding or engineering viral coats large enough to accept large genes such as the one for Factor VIII (anti-hemophilic factor). However, in vivo gene therapy is accomplished in some embodiments by, for example, incorporating DNA into the electroprocessed material as it is created through the electroprocessing techniques of the present invention, whereby some DNA will be incorporated into cells in contact with the composition after application of the composition to the recipient in vivo. This is especially true of small gene sequences, such as sense and/or antisense oligonucleotides. Another example is the use of matrices for cell culture and growth. Cells can be electroprocessed or otherwise inserted into a collagen matrix and placed in conditions to allow cell reproduction and tissue growth. Optionally, the matrix can be placed in a bioreactor.

Use of Electroprocessed Collagen Matrices in Substance Delivery

One use of the electroprocessed collagen compositions of the present invention is the delivery of one or more substances to a desired location. In some embodiments, the electroprocessed materials are used simply to deliver the materials. In other embodiments, the electroprocessed materials are used to deliver substances that are contained in the electroprocessed materials or that are produced or released by substances contained in the electroprocessed materials. For example, an electroprocessed material containing cells can be implanted in a body and used to deliver molecules produced by the cells after implantation. The present compositions can be used to deliver substances to an in vivo location, an in vitro location, or other locations. The present compositions can be administered to these locations using any method. In some embodiments, electroprocessed collagen compositions used in tissue scaffolding deliver substances that will aid in the function of the scaffolding. Any substance that will aid in the function of the scaffold may be used. By way of illustration only, examples include, but are not limited to, delivery of nerve growth factor (NGF) to promote innervation of an implanted scaffold, and delivery of vascular endothelial growth factor (VEGF) to promote vascularization of an implanted scaffold. In some embodiments, electroprocessed collagen will deliver a substance using a two-phase release profile including an initial period of fairly rapid release followed by a slower release period.

In the field of substance delivery, the compositions of the present invention have many attributes that allow delivery of substances using a wide variety of release profiles and release kinetics. For example, selection of the substance and the method by which the substance is combined with the electroprocessed material affects the substance release profile. To the extent that the substances are not immobilized by the electroprocessed collagen, release from the electroprocessed collagen is a function of diffusion. An example of such an embodiment is one in which the substance is sprayed onto the electroprocessed collagen. To the extent that the substances are immobilized by the electroprocessed material, release rate is more closely related to the rate at which the electroprocessed material degrades. An example of such an embodiment is one in which the substance is covalently bonded to the electroprocessed collagen. For a substance trapped within an electrospun aggregate or filament, release kinetics are determined by the rate at which the surrounding material degrades or disintegrates. Still other examples are substances that are coupled to the electroprocessed material by a light sensitive bond. Exposing such a bond to light releases the substance from the electroprocessed material. Conversely, in some embodiments of this invention, materials can be exposed to light to cause binding of agents in vivo or in vitro. Combining the compound with the electroprocessed material in solution, rather than in suspension, results in a different pattern of release and thereby provides another level of control for the process. Further, the porosity of the electroprocessed collagen can be regulated, which affects the release rate of a substance. Enhanced porosity facilitates release. Substance release is also enhanced by milling, fragmenting or pulverizing the electroprocessed collagen. Pulverized material can, for example be applied to a wound site, ingested or formed into another shape such as a capsule or a tablet. In embodiments in which the substance is present in the form of a large particle such as a tablet encapsulated in the electroprocessed material, or a molecule trapped inside an electroprocessed filament, release is dictated by a complex interplay of the rate the particles dissolve or degrade and any breakdown or degradation of the electroprocessed material structure. In embodiments in which the substance comprises cells that express one or more desired compounds, factors that affect the function and viability of the cells and the timing, intensity, and duration of expression can all affect the release kinetics. Chemicals that affect cell function, such as oligonucleotides, promoters or inhibitors of cell adhesion, hormones, and growth factors, for example, can be incorporated into the electroprocessed material and the release of those substances from the electroprocessed material provides a means of controlling expression or other cellular functions in the electroprocessed material.

Release kinetics in some embodiments are manipulated by cross-linking electroprocessed collagen material through any means. In some embodiments, cross-linking will alter, for example, the rate at which the electroprocessed collagen matrix degrades or the rate at which a compound is released from the electroprocessed material by increasing structural rigidity and delaying subsequent dissolution of the electroprocessed material. Electroprocessed collagen materials can be formed in the presence of cross-linking agents or can be treated with cross-linking agents after electrodeposition. Any technique for cross-linking materials may be used as known to one of ordinary skill in the art Examples of techniques include application of cross-linking agents and application of certain cross-linking radiations. Examples of cross-linking agents that work with one or more proteins include but are not limited to condensing agents such as aldehydes e.g., glutaraldehyde, carbodiimide EDC (1-ethyl-3(3 dimethyl aminopropyl)), photosensitive materials that cross link upon exposure to specific wavelengths of light, osmium tetroxide, carbodiimide hydrochloride, NHS (n-hydroxysuccinimide), and Factor XIIIa. Ultraviolet radiation is one example of radiation used to crosslink matrix materials in some embodiments. Natural materials can be cross-linked with other natural materials. For example, collagen can be cross-linked and or stabilized by the addition of fibronectin and or heparin sulfate. For some polymers heat can be used to alter the matrix and cross link elements of the matrix by fusing adjacent components of the construct. Polymers may also be partially solubilized to alter the structure of the material, for example brief exposure of some synthetics to alcohols or bases can partially dissolve and anneal adjacent filaments together. Some polymers may be cross-linked using chemical fusion or heat fusion techniques. Synthetic polymers generally can be cross-linked using high energy radiation (e.g., electron beams, gamma rays). These typically work by the creation of free radicals on the polymer backbone which then couple, affording cross links. Backbone-free radicals can also be generated via peroxides, azo compounds, aryl ketones and other radical-producing compounds in the presence of heat or light. Reduction-oxidation reactions that produce radicals (e.g., peroxides in the presence of transition metal salts) can also be used. In many cases, functional groups on polymer backbones or side chains can be reacted to form cross-links. For example, polysaccharides can be treated with diacylchlorides to form diester cross-links. Cross-linking may also occur after application of a matrix where desirable. For example, a matrix applied to a wound may be cross-linked after application to enhance adhesion of the matrix to the wound.

The release kinetics of the substance is also controlled by manipulating the physical and chemical composition of the electroprocessed collagen and other electroprocessed materials. For example, small fibers of PGA are more susceptible to hydrolysis than larger diameter fibers of PGA. An agent delivered within an electroprocessed material composed of smaller PGA fibers is released more quickly than when prepared within a material composed of larger diameter PGA fibers.

In some embodiments substances such as peptides can be released in a controlled manner in a localized domain. Examples include embodiments in which the substance is chemically or covalently bonded to the electroprocessed material. The formation of peptide gradients is a critical regulatory component of many biological processes, for example in neovasculogenesis. Physical processing of the formed electroprocessed collagen matrix is another way to manipulate release kinetics. In some embodiments, mechanical forces, such as compression, applied to an electroprocessed material hasten the breakdown of the matrix by altering the crystalline structure of the material. Structure of the matrix is thus another parameter that can be manipulated to affect release kinetics. Polyurethanes and other elastic materials such as poly(ethylene-co-vinyl acetate), silicones, and polydienes (e.g., polyisoprene), polycaprolactone, polyglycolic acid and related polymers are examples of materials whose release rate can be altered by mechanical strain. Matrices that also contain those materials are thus subject to control by physical manipulation.

Release kinetics can also be controlled by preparing laminates comprising layers of electroprocessed materials with different properties and substances. For example, layered structures composed of electroprocessed collagen alternating with other electroprocessed materials can be prepared by sequentially electroprocessing different materials onto a target. The outer layers can, for example, be tailored to dissolve faster or slower with respect to the inner layers. Multiple agents can be delivered by this method, optionally at different release rates. Layers can be tailored to provide a complex, multi-kinetic release profile of a single agent over time. Using combinations of the foregoing can provide for release of multiple substances released, each with a complex profile.

Suspending a substance in particles that are incorporated in the electroprocessed collagen or other materials in the collagen matrix provides another means for controlling release profile. Selection of the composition of these smaller particle matrices provides yet another way to control the release of compounds from the electroprocessed material. The release profile can be tailored by the composition of the material used in the process.

Embodiments also exist in which the substances are contained in liposomes or other vesicles in the electroprocessed matrix. Vesicles are prepared that will release one or more compounds when placed in fluids at a specific pH range, temperature range, or ionic concentration. Methods for preparing such vesicles are known to persons of skill in the art. The electroprocessed material can be delivered to a site of interest immediately or is stored either dry or at a pH at which release will not occur, and then delivered to a location containing liquids that have a pH at which release will occur. An example of this embodiment is an electroprocessed material containing vesicles that release a desired compound at the pH of blood or other fluids released from a wound. The matrix is placed over a wound and releases fluids upon discharge of fluids from the wound.

Incorporating constituents that are magnetically sensitive or electrically sensitive into the electroprocessed collagen materials provides another means of controlling the release profile. A magnetic or electric field is subsequently applied to some or all of the matrix to alter the shape, porosity and/or density of the electroprocessed collagen. For example, a field can stimulate movement or conformational changes in a matrix due to the movement of magnetically or electrically sensitive particles. Such movement can affect the release of compounds from the electroprocessed matrix. For example, altering the conformation of the matrix can increase or decrease the extent to which the material is favorable for compound release.

In some embodiments, magnetically or electrically sensitive constituents that have been processed or co-processed with electroprocessed collagen are implanted subdermally to allow delivery of a drug over a long interval of time. By passing a magnetic field or an electrical field across the material, drug release is induced. The electroprocessed collagen structure is stable and does not substantially change without electromagnetic stimulation. Such embodiments provide controlled drug delivery over a long period of time. For example, an electroprocessed collagen material that has magnetic or electrical properties and insulin can be fabricated and placed subdermally in an inconspicuous site. By passing a magnetic field or an electrical field across the composition, insulin release is induced. A similar strategy may be used to release compounds from a construct that has light sensitive elements, exposing these materials to light will either cause the material itself to breakdown and or cause the release of substances that are bound to the electroprocessed collagen material by the light sensitive moiety.

In other embodiments, the substances comprise vesicles encapsulated within the electroprocessed collagen material along with electrical or magnetic materials. The vesicles contain a compound to be released from the vesicles. Placing an electrical or magnetic field across the electroprocessed material causes the compounds within the vesicles to be released by, for example, deforming the vesicles to the point of rupture or by changing the permeability (in some cases reversibly) of the vesicle wall. Examples of these embodiments include transfection agents, such as liposomes, that contain nucleic acids that enhance the efficiency of the process of gene delivery to cells.

In other embodiments, the composition comprising electroprocessed collagen and substances is used as a transdermal patch for localized delivery of medication, or of a component of such a patch. In some of these embodiments, electrically conductive materials are incorporated into such a composition, which is then used as a component of an iontophoresis system in which one or more substances is delivered in response to the passage of electric current. Electrically conductive materials can have a direct healing effect on bone injuries. For example placing a small electric current across a fracture site promotes healing. An electroprocessed bone mimetic that conducts or produces current can be made and placed within a fracture. The addition of the electrical current promotes healing at a rate that is faster than the addition of the electroprocessed composition alone.

In other embodiments, an electroprocessed collagen material or a portion thereof containing electromagnetic properties is stimulated by exposure to a magnet to move and thereby apply or release physical pressure to a pressure-sensitive capsule or other enclosure that contains molecules to be released from the material. Depending on the embodiment, the movement will affect the release relate of the encapsulated molecules.

Response of the composition to electric and magnetic fields can be regulated by features such as the composition of the electroprocessed collagen and other option electroprocessed materials, size of the filaments, and the amount of conductive material added. Electromechanical response from polyaniline is the result of doping-induced volume changes, whereas ion gradients leading osmotic pressure gradients are responsible for field-induced deformation in ionic gels such as poly(2-acrylamido-2-methyl propanesulfonicacid). In each case, ion transport kinetics dominate the response, and facile transport is observed with the small fibers. Gel swelling and shrinking kinetics have been shown to be proportional to the square of the diameter of a gel fiber. Electromechanical response times of fiber bundles of less than 0.1 s, are possible in typical muscle.

Embodiments involving delivery of molecules produced by cells provide many means by which rejection and immune response to cells can be avoided. Embodiments using cells from a recipient thus avoid the problems associated with rejection and inflammatory and immunological responses to the cells. In embodiments in which cells from an organism other than the recipient are used, the matrix can sequester the cells from immune surveillance by the recipient's immune system. By controlling parameters such as the pore size of the electroprocessed material or matrix, nutritive support to the cells trapped in the matrix can be permitted while the cells are protected from detection and response by the recipient's immune system. As an example, pancreatic islet cells that manufacture insulin collected from a donor can be encapsulated in an electroprocessed matrix and implanted in a recipient who cannot make insulin. Such an implant can be placed, for example, subdermally, within the liver, or intramuscularly. For some immune responses permanent sequestration from the host system may not be necessary. The electroprocessed collagen material can be designed to shield the implanted material for a given length of time and then begin to breakdown. In still other embodiments, bacteria or other microbial agents engineered to manufacture the desired compound can be used. This embodiment provides the advantages of using cells that are more easily manipulated than cells from the recipient or a donor. Again, the electroprocessed collagen material can serve to shield the bacteria from immune response in this embodiment. The advantage of using a bacterial carrier is that these microbes are more easily manipulated to express a wide variety of products. Embodiments in which cells are transiently transfected allow for expression to be limited to a defined period. Transient genetic engineering allows cells to revert to their original state in embodiments in which such reversion is desired to minimize the risks of complications.

In some embodiments, cells are genetically engineered such that the expression of a specific gene may be promoted or inhibited through various means known in the art. For example, a tetracycline sensitive promoter can be engineered into a gene sequence. That sequence is not expressed until the tetracycline is present. Cell markers or bacterial markers can also be used to identify the inserted material. For example, green fluorescent proteins placed within an engineered genetic material glow green when expressed. Embodiments using this feature allow verification of the viability of the cells, bacteria, or gene sequences in a matrix. The visibility of such a marker also assists in recovering an implanted electroprocessed composition.

Although the present invention provides versatility in release kinetics, embodiments also exist in which one or more substances are not released from the electroprocessed collagen. Substances may perform a function at a desired site. For example, in some embodiments, antibodies for a specific molecule are immobilized on an electroprocessed collagen matrix and the composition is placed at a desired site. In this embodiment, the antibodies acts to bind the molecules in the vicinity of the composition. This embodiment is useful for isolating molecules that bind to an antibody. An example is an electroprocessed collagen matrix containing immobilized substrates that will bind irreversibly to an undesirable enzyme and thereby inactivate the enzyme.

The compositions of the present invention may be combined with pharmaceutically or cosmetically acceptable carriers and administered as compositions in vitro or in vivo. Forms of administration include, but are not limited to, injections, solutions, creams, gels, implants, pumps, ointments, emulsions, suspensions, microspheres, particles, microparticles, nanoparticles, liposomes, pastes, patches, tablets, transdermal delivery devices, sprays, aerosols, or other means familiar to one of ordinary skill in the art. Such pharmaceutically or cosmetically acceptable carriers are commonly known to one of ordinary skill in the art. Pharmaceutical formulations of the present invention can be prepared by procedures known in the art using well known and readily available ingredients. For example, the compounds can be formulated with common excipients, diluents, or carriers, and formed into tablets, capsules, suspensions, powders, and the like. Examples of excipients, diluents, and carriers that are suitable for such formulations include the following: fillers and extenders (e.g., starch, sugars, mannitol, and silicic derivatives); binding agents (e.g., carboxymethyl cellulose and other cellulose derivatives, alginates, gelatin, and polyvinyl-pyrrolidone); moisturizing agents (e.g., glycerol); disintegrating agents (e.g., calcium carbonate and sodium bicarbonate); agents for retarding dissolution (e.g., paraffin); resorption accelerators (e.g., quaternary ammonium compounds); surface active agents (e.g., cetyl alcohol, glycerol monostearate); adsorptive carriers (e.g., kaolin and bentonite); emulsifiers; preservatives; sweeteners; stabilizers; coloring agents; perfuming agents; flavoring agents; lubricants (e.g., talc, calcium and magnesium stearate); solid polyethyl glycols; and mixtures thereof.

The terms "pharmaceutically or cosmetically acceptable carrier" or "pharmaceutically or cosmetically acceptable vehicle" are used herein to mean, without limitations, any liquid, solid or semi-solid, including, but not limited to, water or saline, a gel, cream, salve, solvent, diluent, fluid ointment base, ointment, paste, implant, liposome, micelle, giant micelle, and the like, which is suitable for use in contact with living animal or human tissue without causing adverse physiological or cosmetic responses, and which does not interact with the other components of the composition in a deleterious manner. Other pharmaceutically or cosmetically acceptable carriers or vehicles known to one of skill in the art may be employed to make compositions for delivering the molecules of the present invention.

The formulations can be so constituted that they release the active ingredient only or preferably in a particular location, possibly over a period of time. Such combinations provide yet a further mechanism for controlling release kinetics. The coatings, envelopes, and protective matrices may be made, for example, from polymeric substances or waxes.

Methods of in vivo administration of the compositions of the present invention, or of formulations comprising such compositions and other materials such as carriers of the present invention that are particularly suitable for various forms include, but are not limited to, oral administration (e.g. buccal or sublingual administration), anal administration, rectal administration, administration as a suppository, topical application, aerosol application, inhalation, intraperitoneal administration, intravenous administration, transdermal administration, intradermal administration, subdermal administration, intramuscular administration, intrauterine administration, vaginal administration, administration into a body cavity, surgical administration at the location of a tumor or internal injury, administration into the lumen or parenchyma of an organ, and parenteral administration. Techniques useful in the various forms of administrations above include but are not limited to, topical application, ingestion, surgical administration, injections, sprays, transdermal delivery devices, osmotic pumps, electrodepositing directly on a desired site, or other means familiar to one of ordinary skill in the art. Sites of application can be external, such as on the epidermis, or internal, for example a gastric ulcer, a surgical field, or elsewhere.

The electroprocessed collagen compositions of the present invention can be applied in the form of creams, gels, solutions, suspensions, liposomes, particles, or other means known to one of skill in the art of formulation and delivery of therapeutic and cosmetic compounds. Ultrafine particle sizes of electroprocessed collagen materials can be used for inhalation delivery of therapeutics. Some examples of appropriate formulations for subcutaneous administration include but are not limited to implants, depot, needles, capsules, and osmotic pumps. Some examples of appropriate formulations for vaginal administration include but are not limited to creams and rings. Some examples of appropriate formulations for oral administration include but are not limited to: pills, liquids, syrups, and suspensions. Some examples of appropriate formulations for transdermal administration include but are not limited to gels, creams, pastes, patches, sprays, and gels. Some examples of appropriate delivery mechanisms for subcutaneous administration include but are not limited to implants, depots, needles, capsules, and osmotic pumps. Formulations suitable for parenteral administration include but are not limited to aqueous and non-aqueous sterile injection solutions which may contain anti-oxidants, buffers, bacteriostats and solutes which render the formulation isotonic with the blood of the intended recipient, and aqueous and non-aqueous sterile suspensions which may include suspending agents and thickening agents. Extemporaneous injection solutions and suspensions may be prepared from sterile powders, granules and tablets commonly used by one of ordinary skill in the art.

Embodiments in which the compositions of the invention are combined with, for example, one or more "pharmaceutically or cosmetically acceptable carriers" or excipients may conveniently be presented in unit dosage form and may be prepared by conventional pharmaceutical techniques. Such techniques include the step of bringing into association the compositions containing the active ingredient and the pharmaceutical carrier(s) or excipient(s). In general, the formulations are prepared by uniformly and intimately bringing into association the active ingredient with liquid carriers. Preferred unit dosage formulations are those containing a dose or unit, or an appropriate fraction thereof, of the administered ingredient. It should be understood that in addition to the ingredients particularly mentioned above, formulations comprising the compositions of the present invention may include other agents commonly used by one of ordinary skill in the art. The volume of administration will vary depending on the route of administration. For example, intramuscular injections may range in volume from about 0.1 ml to 1.0 ml.

The compositions of the present invention may be administered to persons or animals to provide substances in any dose range that will produce desired physiological or pharmacological results. Dosage will depend upon the substance or substances administered, the therapeutic endpoint desired, the desired effective concentration at the site of action or in a body fluid, and the type of administration. Information regarding appropriate doses of substances are known to persons of ordinary skill in the art and may be found in references such as L. S. Goodman and A. Gilman, eds, *The Pharmacological Basis of Therapeutics*, Macmillan Publishing, New York, and Katzung, *Basic & Clinical Pharmacology*, Appleton & Lang, Norwalk, Conn., (6$^{th}$ Ed. 1995). One desirable dosage range is 0.01 µg to 100 mg. Another desirable dosage range is 0.1 µg to 50 mg. Another desirable dosage range is 0.1 µg to 1.0 µg. A clinician skilled in the art of the desired therapy may chose specific dosages and dose ranges, and frequency of administration, as required by the circumstances and the substances to be administered. For example, a clinician skilled in the art of hormone replacement therapy may chose specific dosages and dose ranges, and frequency of administration, for a substance such as progesterone, to be administered in combination with the estrogenic and estrogenic modulatory molecules as required by the circumstances. For example, progesterone, and other progestins known to one of skill in the art may be administered in amounts ranging from about 50 µg to 300 mg, preferably 100 µg to 200 mg, more preferably 1 mg to 100 mg. Specific dosages and combinations of dosages of estrogenic and estrogenic modulatory molecules and progestins will depend on the route and frequency of administration, and also on the condition to be treated. For example, when the composition is formulated for oral administration, preferably in the form of a dosage unit such as a capsule, each dosage unit may preferably contain 1 µg to 5 mg of estrogenic and estrogenic modulatory molecules and 50 µg to 300 mg of progesterone. U.S. Pat. No. 4,900,734 provides additional examples of acceptable dose combinations of estrogenic molecules and progestins.

Other Uses Involving Electrically or Magnetically Active Constituents

The compositions of the present invention have a number of additional uses aside from substance delivery. Embodiments exist in which the incorporation of electrically or magnetically active constituents in the electroprocessed material allows the electroprocessed material to move rhythmically in response to an oscillating electric or magnetic field. Such an electroprocessed material can be used, for example, in a left ventricular assist device by providing a pumping action or a ventricular massage to a heart patient. Oscillations can be accomplished by passive movement of a magnetic or electric field with respect to the conductive material, or vice versa. By manipulating material selection, the electroprocessed material can be designed to remain in place permanently or to dissolve over time, eliminating the need for surgery to recover the device once the heart had recovered sufficiently.

Embodiments also exist in which an implanted electroprocessed material is used to convey an electric charge or current to tissue. For example, electrically active constituents can be electrically stimulated to promote neural ingrowth, stem cell differentiation, or contraction of engineered muscle, or to promote the formation of bone in orthopedic applications in which electroprocessed material is used as a carrier to reconstruct bone. In one embodiment, for example, an electroprocessed material is applied to a bone injury site and used to apply an electric current to the material to facilitate and to promote healing. The application of a small electric current to an injured bone is known to accelerate healing or promote the healing of bone injuries.

In other embodiments involving magnetically reactive materials, a magnetic field is used to position an electroprocessed material containing substances by relatively non-invasive means, for example by directing the movement of the material within the peritoneum. In other embodiments, a composition containing electrically active compounds is used to produce electric field-driven cell migration. This approach accelerates the healing process and minimize the risk of bacterial colonization. In one example, an orthopedic implant is coated with a very thin (<100 microns) layer of an electrically active polymer. With a very thin electrode attached to the coating, upon post-implantation, an electric field can be applied via an external electrode such that the electric field-driven cell migration is towards the implant surface. The direction can be reversed if so desired. Field orientation depends on the geometry of the implant and external electrode.

In surgical applications, anti-vascular peptides or antisense oligonucleotides can be incorporated into an electroprocessed material that is then wrapped around or placed within a tumor that is inaccessible to conventional treatments to allow for localized release and effect. Release of the anti-vascular substances suppresses tumor growth. Antisense oligonucleotides can be released from the construct into the tumor and used to suppress the expression gene sequences of interest. In another example anti-sense sequences directed against gene sequences that control proliferation can be delivered within an electroprocessed matrix coated stent. The stretch normally associated with the placement of the stent initiates smooth muscle cell proliferation, and anti-sense sequences designed to suppress cell division reduce the deleterious effects of the smooth muscle cell proliferation associated with the procedure. In another embodiments, the electroprocessed material delivers sense and antisense oligonucleotides to promote or to inhibit localized cell function for a period of time. For example, an antisense oligonucleotide is released from an electroprocessed material to suppress the expression of a deleterious enzyme in a wound. Examples of such enzymes are matrix metalloproteinases (MMPs), which are often overexpressed in chronic wounds. In another example, the electroprocessed material applied to a wound releases plasmids that contain nucleotide sequences coding for tissue inhibitors of metalloproteinases (TIMPs). Cells in the wound will express TIMPs, resulting in local delivery of TIMPs that will inhibit MMP function.

The present invention is further illustrated by the following examples, which are not to be construed in any way as imposing limitations upon the scope thereof. On the contrary, it is to be clearly understood that resort can be had to various other embodiments, modifications, and equivalents thereof, which, after reading the description herein, can suggest themselves to those skilled in the art without departing from the spirit of the present invention.

EXAMPLE 1

Fibroblast Growth Factor (FGF) Release from an Implant Comprised of Type I Collagen, PGA and PLA Fibroblast growth factor (FGF, obtained from Chemicon, Temecula, Calif.) was dissolved in a solution of matrix material comprised of type 1 collagen (80%), PGA (10%) and PLA (10%). The percentages refer to the weight of the materials with respect to one another. These materials were dissolved in HFIP at a final concentration of 0.08 gm per ml. Sufficient FGF was added to 1 ml of solution to provide an FGF concentration of 50 ng/ml of the collagen/PGA/PLA electrospinning solution. The material was electrospun into the shape of a cylinder onto the outer surface of a grounded and spinning 16 gauge needle about 25-35 mm in length. After completion of electrospinning, the material was removed from the needle and the electrospun cylinder was sutured shut looping a suture around the outside of the construct and pulling tight to seal the ends. A similar result may be obtained by using a hot forceps is used to pinch the ends together and heat seal the ends shut. A hollow enclosed construct was formed. The construct was then surgically implanted within the vastus lateralis muscle of a rat. The construct was left in place for seven days and recovered for inspection. FGF in the matrix accelerated muscle formation within the electrospun matrix by promoting muscle formation within the wall of the electrospun cylinder.

EXAMPLE 2

Vascular Endothelial Growth Factor (VEGF) Release from an Implant Material Comprised of Type I Collagen, PGA and PLA Vascular endothelial growth factor (VEGF, obtained from Chemicon, Temecula, Calif.) was dissolved in a solution of matrix material comprised of type I collagen (80%), PGA (10%) and PLA (10%) as described in example 1. These materials were dissolved in HFIP at a final concentration of 0.08 gm per ml. Sufficient VEGF was added to 1 ml of solution to provide a VEGF concentration of 50 ng/ml of the collagen/PGA/PLA electrospinning solution. The material was electrospun to form a cylindrical construct and implanted into the rat vastus lateralis muscle using the same procedures set forth in Example 1. VEGF increased the density of functional capillaries that were present throughout the construct. This was evidenced by the presence of capillaries containing red blood cells (RBCs).

EXAMPLE 3

Release of VEGF from Constructs of Electroprocessed Collagen, PGA, and PLA

Constructs of electroprocessed collagen and PGA:PLA copolymer, with VEGF spun into the matrix were prepared using 80% collagen and 20% PGA:PLA. The collagen and PGA:PLA were dissolved in HFIP at a final combined concentration of 0.08 gm per ml. Solutions were prepared in which different amounts of VEGF were added to 1 ml of the solution of collagen and PGA:PLA copolymer. Separate solutions for electrospinning were prepared containing 0 ng, 25 ng, 50 ng, and 100 ng each of VEGF in 1 ml of electrospinning solution. Constructs were prepared for each solution by electrospinning 1 ml of material onto a cylindrical construct (2 mm in diameter). The constructs were removed from the target needle and cut in half. One half of each electrospun sample was then exposed to glutaraldehyde vapor fixation to cross link the fibers of collagen. Cross-linking was accomplished by exposing the constructs to glutaraldehyde vapor for 15 minutes. For vapor fixation, the samples of the electroprocessed constructs were placed in a 100 mm tissue culture dish. A 35 mm tissue culture dish containing 1 ml of 50% glutaraldehyde was placed inside the 100 mm tissue culture dish. The lid of the 100 mm tissue culture dish was replaced and the sample was allowed to sit for 15 minutes at room temperature. The vapor fixed and samples of the unfixed electrospun constructs were then immersed in PBS and the amount of VEGF (expressed in picograms per 1 mg of electrospun material) for the non cross-linked and cross-linked samples was measured at different times are presented in FIGS. 7 and 8, respectively. Release of VEGF into the PBS was measured as a function of time by the ELISA method. The ELISA kit for VEGF was purchased from Chemicon International (part number cyt214) and the directions provided in the kit were followed to perform the ELISA. Samples were centrifuged to remove particulate matter and stored at −20° C. prior to use.

Figure 7:
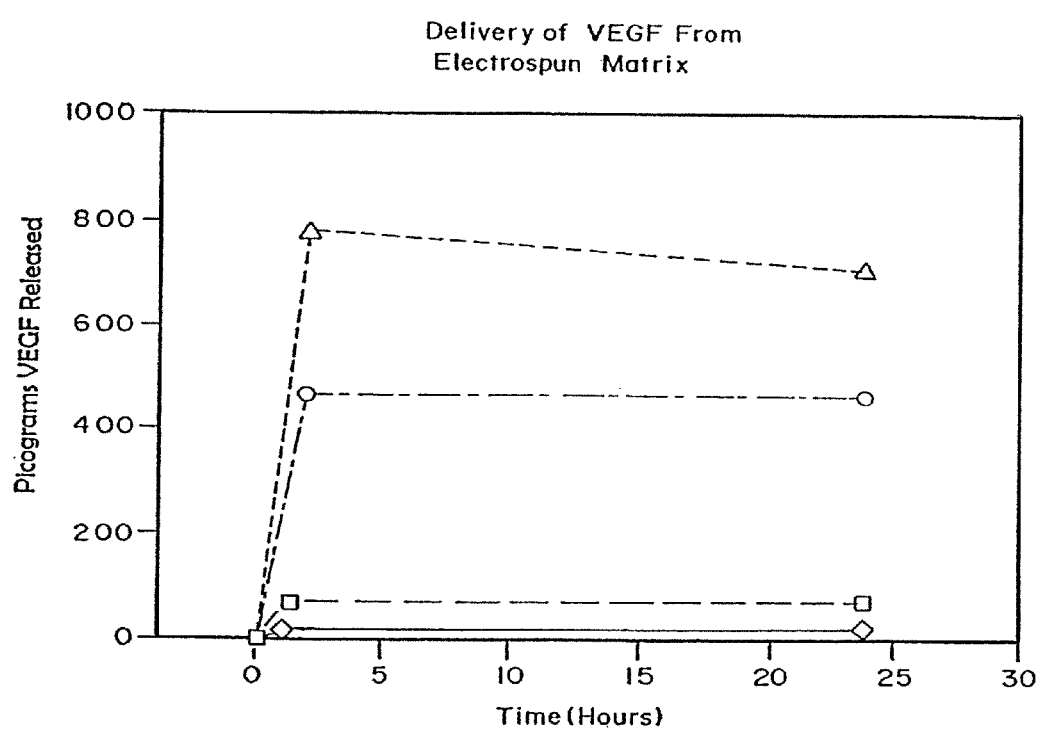
FIG. 7. Representative release profile of VEGF from electrospun collagen. VEGF was co-electrospun at concentrations of 0, 25, 50 or 100 ng/ml collagen. The material was then immersed in PBS and samples were isolated and subjected to ELISA.
Figure 8:
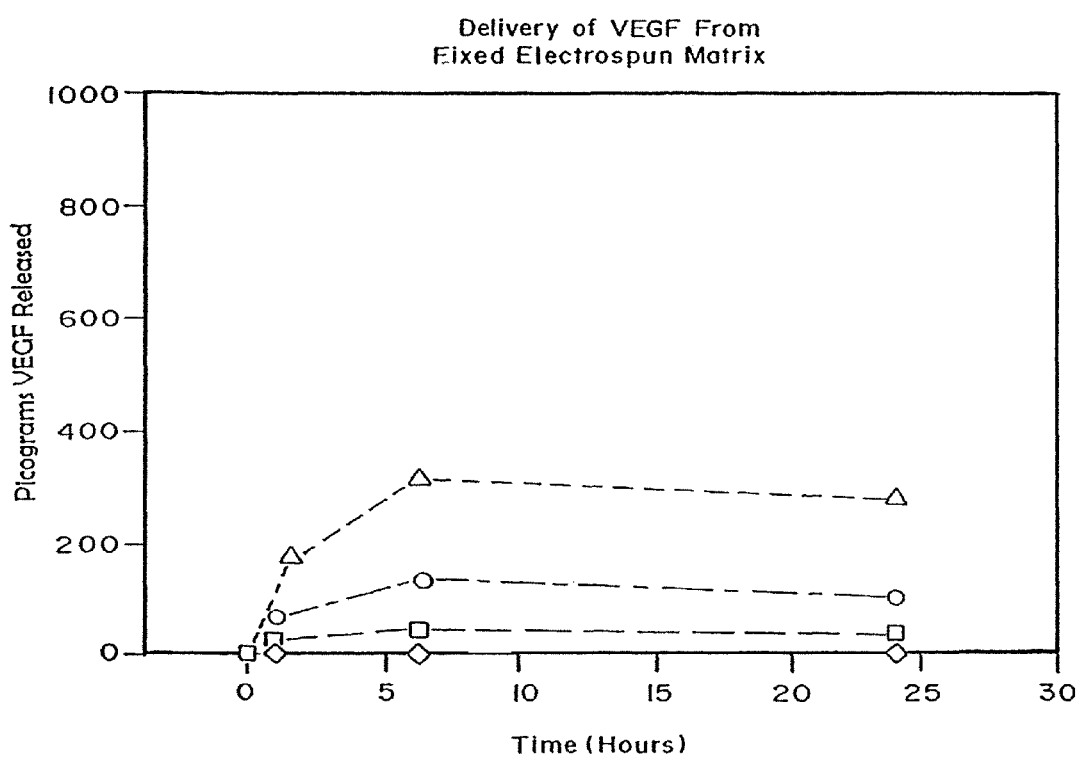
FIG. 8. Release of VEGF from electrospun and glutaraldehyde, vapor-fixed collagen. VEGF was co-electrospun at a concentration of 0, 25, 50 or 100 ng/ml collagen. The electrospun material was subjected to a 15-minute interval of glutaraldehyde vapor fixation. The material was then immersed in PBS and samples were isolated and subjected to ELISA.

In FIG. 7 and FIG. 8, the open diamonds represent release from the fibers electrospun from the solution containing PGA:PLA copolymer and collagen to which no VEGF was added. The open squares represent release from fibers electrospun from the solution containing PGA:PLA copolymer and collagen to which 25 ng of VEGF were added. The open circles represent release from the fibers electrospun from a solution containing PGA:PLA copolymer and collagen to which 50 ng of VEGF were added. The open triangles represent release from the fibers electrospun from a solution containing PGA:PLA copolymer and collagen to which 100 ng of VEGF were added. Results demonstrate not only that the matrix releases VEGF in PBS but also that cross-linking with glutaraldehyde slows release from the matrix.

EXAMPLE 4

Electroprocessed Collagen Matrix: Pancreatic Islet

A mixture of cultured insulin secreting cells is seeded into an electroprocessed collagen matrix to form an electroprocessed collagen-containing tissue. The electroprocessed matrix containing the insulin secreting cells is implanted into a diabetic recipient in need of insulin. This electroprocessed collagen or fibrin-containing tissue optionally contains a vessel. The matrix is implanted into the retroperitoneal space and the vessel is anastomosed into the hepatic portal circulation. Insulin is released from the insulin-containing cell and transmitted to the circulation.

The electroprocessed matrix containing the insulin secreting cells is optionally supplemented with cells that synthesize and secrete glucagon, somatostatin, pancreatic polypeptide, or combinations thereof, in order to mimic the hormonal complement of the pancreatic islet.

Optionally, heterologous cells, (for example, engineered bacteria or cells from a conspecific donor) are placed in a matrix with a pore size that will allows diffusion of nutrients to the cells but does not allow or inhibits or delays the detection of the cells by the recipient's immune system.

EXAMPLE 5

Electroprocessed Collagen Matrix for Wound Repair

Keratinocytes are harvested from a healthy site of a patient suffering from a chronic wound. The cells are grown in culture and transfected by electroporation to express VEGF. Next, the transfected cells are mixed or prepared in an electrospun collagen matrix. Antisense oligonucleotide for matrix metalloproteinases (MMPs) are also spun into the matrix. The matrix is topically applied to the surface of the wound. The cells near and in the implant take up the antisense sequences, express their transfected gene sequences and MMP production is reduced. In other applications the cells may be genetically engineered to secrete VEGF, thereby promoting healing. Release of the antisense oligonucleotides suppress expression of MMPs, which are typically overexpressed in a chronic wound. Thus the wound site is repaired with an implant that simultaneously promotes natural healing responses. Optionally, the matrix is comprised of fibrin or a mix of fibrin and collagen. The fibrin assists in cessation of bleeding and promotes healing.

EXAMPLE 6

Electrospun Collagen Matrix for Bone Repair

Osteoblasts from a patient with a bone injury are cultured and incorporated into an electrospun matrix comprising type I collagen. The matrix is formed in the shape of a cavity or defect at the injury site. Bone growth factor (BGF), bone morphogenic protein (BMP) or sequences of genes encoding for these proteins, are electrospun into the matrix are optionally incorporated into the electrospun matrix. The matrix assists in growth of new bone, and the BGF or BMP in the matrix promotes bone growth.

Optionally, the collagen used is produced in vitro by genetically engineered cells that express a collagen polymer with more P-15 sites than in normal collagen. The excess of P-15 sites promotes osteoblasts to produce and secretes hydroxyapatite and further aid bone growth.

Optionally, the matrix is further electroprocessed with polypyrroles, which are electrically active materials. Electrodes are attached to each end of the implanted matrix. Charged electrodes are later applied to the surface over the electrodes to create a small electric current across the implant to further facilitate healing of the bone injury. In another embodiment piezoelectric elements may be electrospun into the matrix to produce electric discharges that promote healing.

EXAMPLE 7

Electroprocessed Collagen Matrix: Cardiac Patch

In this example a cardiac patch is prepared. A sheet of electroprocessed material is prepared with aligned filaments of collagen. The sheet is folded into a pleated sheet in the desired shape and or rolled into a cylinder. A second construct is electrospun in the desired shape, for example a rectangle. The pleated sheet that mimics the cellular layers of the intact heart is inserted into the electroprocessed rectangular form. The construct is filled with cells, sutured shut and placed in a bioreactor or directly in situ. By aligning the fibrils of the pleated electrospun sheet of material in parallel with the long axis of the outer rectangular form, a cardiac, muscle-like construct is obtained. Native cardiac tissue is composed of layers of cells arrayed along a common axis with adjacent cell layers slightly off axis with the overlaying and underlying layers. This structure can be more precisely mimicked by the methods described below in which a matrix is prepared and cells are directly electroprocessed, dribbled or sprayed onto the matrix as it is prepared. Cells in contact with the fibrils of collagen that are arrayed along the long axis of the sheet spread in parallel with the underlying fibrils of the sheet, forming a muscle construct of cells arrayed and layered in an in vivo-like pattern of organization. The construct is directly implanted or placed within a RCCS bioreactor. Rates of rotation to maintain this type of construct in suspension within the RCCS bioreactor range from 4-20 rpm, depending upon the mass of the tissue and the specific materials used to fabricate the outer cylinder. Variations of this design include the addition of angiogenic factors in the matrix, gene sequences, and agents to suppress inflammation and/or rejection. Other cell types may be added to the construct, for example microvascular endothelial cells, to accelerate the formation of a capillary system within the construct. Other variations in this design principle can be used. For example, cells may be electroprocessed into the matrix as it is deposited on the ground target. By varying the pitch of the fibers during spinning and spraying, dribbling or electroprocessing cells onto the fibers as they are deposited very precisely controls the positioning of the cells within the construct.

EXAMPLE 8

Electrospinning of Type I Collagen

Type I collagen was used (calf skin, Sigma Chemical Co.). The collagen was suspended in 1,1,1,3,3,3-hexafluoro-2-isopropanol (HFIP) at a concentration of 0.1181 grams in 3 ml HFIP. Once in solution or suspension (solution a milky color), the solution was loaded into a 1 ml syringe plunger. A 15-gauge luer stub adapter was then placed on the syringe to act as the electrospinning nozzle and charging point for the contained collagen solution. The filled syringe was placed in the a syringe pump (KD Scientific) set to dispense the solution at 18 ml/hr utilizing a 1.0-ml syringe plunger (Becton Dickinson). The positive lead from the high voltage supply was attached to the luer stub adapter metal portion. The syringe pump was turned on. The high voltage supply turned on and set at 20 kV. The grounded target was a 303 stainless steel mandrel (0.6 cm width (W)×0.05 cm height (H)×4 cm length (L)) placed approximately 6 inches from the tip of the adapter. The mandrel was rotated at approximately 500 rpm during the spinning process. About 1 ml of the collagen solution was electrospun to form a white mat on the grounded mandrel. After electrospinning, the collagen mat was removed from the mandrel and processed for scanning electron microscopy. The mat produced was approximately 200 microns thick.

Figure 9:
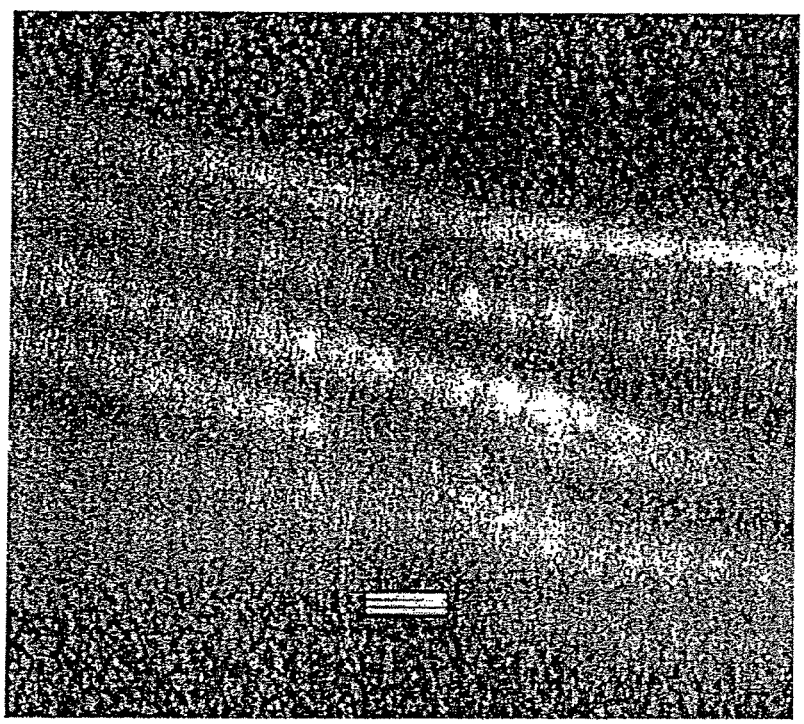
FIG. 9. Transmission electron micrograph of electrospun type I collagen demonstrating 67 nm banding (white scale bar indicates 100 nm).

Transmission electron revealed an approximate 100 nm collagen fiber diameter and the typical 67 nm banding indicative of native collagen polymerization (FIG. 9).

EXAMPLE 9

Electrospinning of Collagen and Elastin

The methods for this example are the same as in Example 8 except for the electrospun solution. In this case, the spinning solution consisted of 0.1155 grams collagen, 0.1234 grams of elastin from ligamentum nuchae (Fluka), and 5 ml HFIP. About 2 ml of the suspension was spun to form the mat. The mat produced was approximately 50 microns thick.

EXAMPLE 10

Electrospinning of Type I Collagen, Type III Collagen and Elastin

The methods for this example are the same as Example 8 except for the electrospun solution. In this example, the solution electrospun was composed of 0.067 grams of type I collagen, 0.067 grams of type III collagen, 0.017 grams of elastin from ligamentum nuchae, and 2 ml HFIP (44% Type I, 44% Type III, and 12% elastin). This ratio is similar to that found in native arterial wall tissue. The mats produced were approximately 100 microns thick.

EXAMPLE 11

Electrospinning of Collagen (Types I and III), Crosslinking, Structural Analysis and Strength Testing Acid soluble, lyophilized collagen was used for all experimentation. Unless otherwise noted all reagents were purchased from Sigma Chemical Company (St. Louis, Mich.). For this study, Type I collagen from calfskin, and Type I and Type III collagen isolated from human placenta were used. Collagen was dissolved at various concentrations in 1,1,1,3,3,3 hexafluoro-2-propanol (HFIP). Suspensions of collagen were placed into a 1.0 ml syringe mounted in a syringe pump (Model 100, KD Scientific Inc., New Hope, Pa.). The syringe was capped with an 18-gauge blunt end needle. The positive lead from a high voltage supply (Spellman CZE1000R; Spellman High Voltage Electronics Corp.) was attached via an alligator clip to the external surface of the metal syringe needle. A cylindrical (0.6 cm W×0.05 cm H×4 cm L) grounded target fabricated from 303 stainless steel was mounted 4-6 inches from the tip of the syringe tip. At the onset of electrospinning, the syringe pump was set to deliver the source solution at rates varying from 0-25 ml/hr. Simultaneously, the high voltage was applied across the source solution and the grounded target mandrel (15-30 kilovolts (kV)). The mandrel rotated at approximately 500 rpm unless otherwise noted. In summary, during the electrospinning process the isotype and concentration of collagen, imposed voltages, the air gap distance, and flow rates were examined. Type I collagen from calfskin was electrospun onto a 4 mm diameter cylindrical culture platform (length=1 cm). Constructs were cross-linked in glutaraldehyde vapor for 24 hours at room temperature and then rinsed through several changes of phosphate buffered saline.

EXAMPLE 12

Testing of Various Conditions for Electrospinning Collagen

Preliminary experimentation identified HFIP as a preferred solvent for electrospinning collagen. HFIP is an organic, volatile solvent with a boiling point of 61° C. The electrospinning of collagen fibers exhibited a concentration dependence on the final fiber diameters produced. For example, at a concentration of 0.008 g/1.0 ml acid extracts of Type I collagen (calfskin) were readily soluble in HFIP. However, at this concentration the collagen did not exhibit any evidence of electrospinning (fiber formation) and, regardless of the input voltage, the polymer solution formed droplets and leaked from the syringe tip. Increasing the concentration of collagen ten fold to 0.083 g/ml resulted in a cloudy suspension and the formation of fibers during electrospinning. These fibers collected as a non-woven mat on the target mandrel. Further increasing the collagen concentration in the source solution did not grossly alter fiber formation.

Next the voltage input parameters were examined. Type I collagen was suspended in HFIP at 0.083 g/ml and then subjected to voltages varying from 15 and 30 kV in 2.0 kV increments. Fiber formation was most prominent at 25 kV (electric field magnitude=2000 V/cm). Varying the air gap distance between the source solution and grounded target at this input voltage markedly affected the electrospinning process. The optimal air gap distance was approximately 125 mm. Collagen fibrils could be spun over substantially shorter air gap distances, however, these fibrils retained considerable solvent and collected on the target in a wet state. When the air gap distance exceeded a critical interval of 250 mm the spun fibers failed to collect on the target mandrel.

The electric field generated in the electrospinning process was sufficient to draw the collagen source solution from a syringe reservoir. However, it is possible to generate a more uniform collagen mat by metering the rate at which the collagen source solution is delivered to the electrospinning field via a syringe pump. Fiber formation was optimal when the collagen source solution was delivered to the electric field at a rate of approximately 5.0 ml/hr. At slower rates of delivery fiber formation was inconsistent.

The rotation of the target mandrel also affected the deposition of collagen. Collagen fibrils electrospun onto a mandrel rotating at a rate of less than 500 rpm. produced a random porous matrix of filaments. Increasing the velocity of the mandrel to 4,500 (mandrel surface moving at approximately 1.4 msec) resulted in deposition of fibrils in linear, parallel arrays along the axis of rotation. Transmission electron microscopic analysis of aligned and non-aligned fibrils revealed these filaments all displayed the 67 nm banding that is characteristic of native collagen.

The stress stain profile of this type of electrospun collagen scaffold was measured. Type I collagen from calf skin was electrospun under optimal conditions onto a rectangular target mandrel rotating at 4,500 rpm. The scaffolding was removed from the target and fashioned into sheets 25 mm (length)×25 mm (width). Under the conditions used to fabricate this matrix the scaffolding averaged 0.187 mm in cross-sectional diameter. Replicate samples were cut into strips that were either parallel or perpendicular to the principle axis of mandrel rotation. This approach permitted examination of how the local fiber direction modulates the material properties of the electrospun matrix. Materials testing of scaffolds in parallel with the principal axis fibril alignment indicated an average load of 1.17±0.34 N at failure with a peak stress of 1.5±0.2 MPa. The average modulus for the longitudinal samples was 52.3±5.2 MPa. In cross fiber orientation the peak load at failure was 0.75±0.04 N with a peak stress of 0.7±0.1 MPa. The modulus across the fiber long axis was 26.1±4.0 MPa. These data indicate the local orientation of the fibers that compose an electrospun scaffolding directly modulate the material properties of the engineered matrix. The incorporation of various degrees of cross linking into this type of non-woven matrix can be used to further tailor the material properties of the matrix to specific applications.

The identity and source of collagen were investigated for effects on the electrospinning process. Type I collagen isolated from human placenta was electrospun using the conditions optimized for Type I calfskin collagen. With respect to calfskin collagen, electrospinning this material produced a less uniform matrix of fibers. Individual filaments ranged from 100-730 nm in diameter. The 0.083 g/ml collagen used in these experiments appears to represent a critical transition concentration for Type I collagen when it is isolated from the placenta. Increasing the concentration of human placental collagen present in the source solution (increased viscosity in electrospinning source solution) and keeping all other variables equal, appears to favor the formation of larger diameter fibers. Conversely, decreasing the concentration of the source solution (decreased viscosity in electrospinning source solution) appeared to reduce the average filament diameter and produces a matrix composed primarily of 100 nm fibers.

Figure 10:
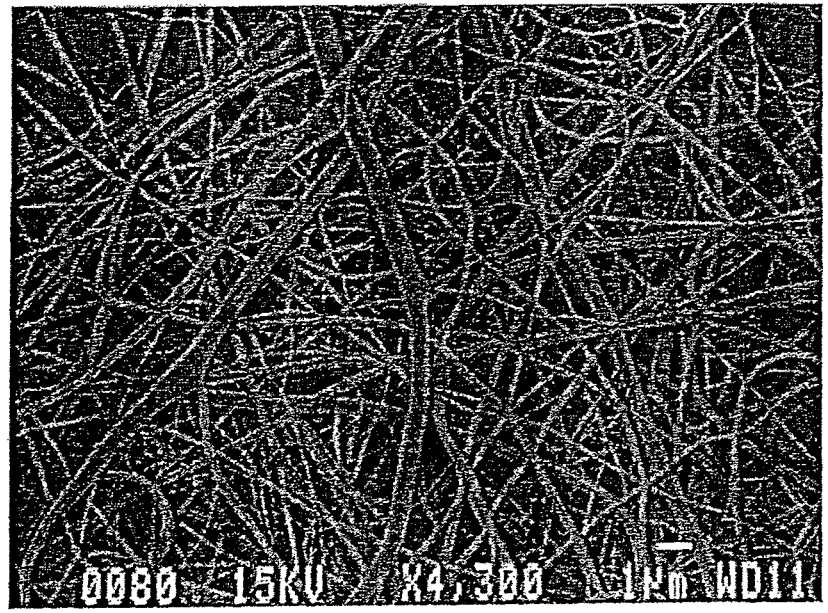
FIG. 10. SEM of an electrospun 50:50 blend of collagen type I and III (human placenta). This matrix was electrospun from a single reservoir source composed of a mixture of Type I and Type III collagen suspended in HFIP (final protein concentration equaled 0.06 g/ml. This heterogeneous network is composed of fibers that average 390±290 nm fiber diameter (Magnification 4,300×).

The primary sequence of collagen directly affects the formation of this polymer in the electrospinning process. Preliminary attempts to electrospin Type III collagen indicated the optimal concentration of this peptide is approximately 0.04 g/ml HFIP, a value 50% less than the optimal concentration of Type I calfskin. Electrospinning Type III collagen at 0.04 g/ml HFIP, using all of the other conditions optimized for electrospinning Type I calfskin collagen, produced fibers with average diameters of 250±150 nm. The relative ratio of Type I to Type III collagen within the native ECM affects the structural and functional properties of the collagen-based network. Blending optimal concentrations of Type I human placental collagen (0.08 g/ml HFIP) and Type III human placental collagen (0.04 g/ml HFIP) at a 50:50 ratio (final collagen concentration 0.06 g/ml) affected the formation of fibrils during the electrospinning process. Under electrospinning conditions optimized for Type I calfskin collagen, the blended material formed a scaffold composed of fibers that averaged 390±290 nm in diameter (FIG. 10).

Crosslinking was also investigated. Regardless of the amount of time which the collagen mats were exposed to UV light, every sample dissolved instantly when they were placed in warm media. Glutaraldehyde exposure produced somewhat different results. While the 1, 2, and 5 minute mats dissolved in the warm media, the rate at which this occurred was slower than the UV exposed mats at any of the time intervals investigated. The 10 and 20 minute mats became somewhat transparent when placed in the media but did not dissolve. The mat exposed overnight to glutaraldehyde appeared somewhat darker in color than when it was first placed in the chamber. It had very little compliance and when placed in the media did not dissolve or demonstrate any signs of thinning. Exposure of the 45:35:20 (Collagen type I, III, elastin) mat to glutaraldehyde for more than 10 minutes produces enough cross linking to make the mat insoluble.

EXAMPLE 13

Biological Properties of Electrospun Collagen

The biological properties of electrospun collagen were examined in tissue culture experiments. Aortic smooth muscle cells were suspended in a RCCS bioreactor and plated out onto different formulations of electrospun collagen. The low shear, high nutrient environment afforded by the RCCS bioreactor fosters cell-matrix interactions and the formation of large scale tissue masses in vitro. Microscopic examination of these cultures revealed that the scaffolds were densely populated with the smooth muscle cells, within seven days. Cross sectional analysis indicated that electrospun collagen promoted extensive cellular infiltration into the fibrillar network. Smooth muscle cells were observed deep within the matrix and fully enmeshed within the fibrils of the electrospun collagen.

EXAMPLE 14

Biocompatibility of Electrospun Collagen-Elastin Matrix In Vivo

To investigate material biocompatibility in vivo, electrospun 80:20 type I collagen/elastin matrices were implanted into both hind legs of a Sprague Dawley rat (Charles River) for 2 weeks. The female rat used for this study weighed approximately 200 g. Cylindrical constructs were implanted to test the performance of this particular fabrication platform. Prior to surgery, the rat was anesthetized with an i.p. injection of pentobarbital (5-7 mg/100 g body wt.). An incision 10-15 mm in length was made along the lateral portion of the hind limb directly superior to the vastus lateralis muscle. A small channel was prepared in the muscle belly by blunt dissection. The electrospun collagen/elastin constructs were placed into the channel. The endogenous muscle was sutured back together over the implanted material, the skin incision was repaired and the area irrigated with betadine. After 14 days the animal was sedated with an IP injection of Pentobarbital and sacrificed by bilateral pneumothorax. Collapse of lung was visually verified and the implanted tissue was recovered for histological evaluation. For histological preparation, this tissue was fixed for 24 hrs in half strength Karnovsky's fixative, embedded and thick sectioned.

To see cell infiltration in vivo, the vessels were viewed under SEM. Removal of the vessels from the rat model after one week revealed cell migration, infiltration, and coverage similar to the vessels after two weeks in culture. There was no inflammation (swelling) at or around the area of implantation. The rat also exhibited fluid movement around the cage. There was no visible encapsulation of the collagen fibers in the matrix, rather, almost the entire vessel matrix was covered with skeletal muscle cells from the rat.

EXAMPLE 15

Cell Infiltration into Electroprocessed Matrices In Vitro

Figure 11:
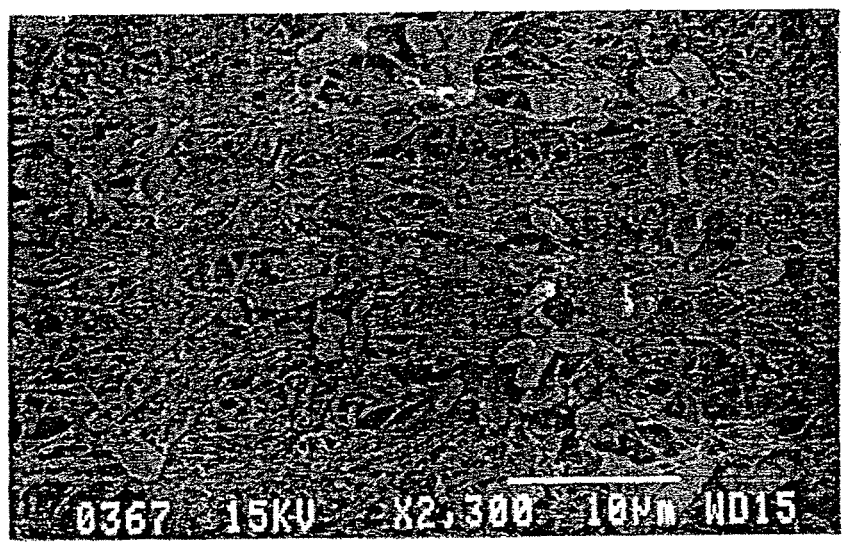
FIG. 11. SEM micrograph showing prominent smooth muscle cell attachment and migration after one week in culture with a 80:20 type I collagen/elastin matrix. Luminal view of prosthetic. (scale size=10 um, magnification 4,300×).

SEM investigation of the three layered 80:20 type I/elastin matrices cultured with smooth muscle cells revealed prominent cell attachment and maturation, including three-dimensional cellular migration into the matrix. After only one week, there was visible cell migration and attachment, as shown by scanning electron microscopy (FIG. 11).

After 2 weeks in the bioreactors, cell maturation was far more prominent. The cells appeared to form a confluent layer across the luminal region of the tube. SEM of a tubular cross section showed cell migration and remodeling of the center region of the wall. Cell migration to the outer wall region of the scaffold was not observed in the two week tubes. However, the center region of the wall was completely infiltrated prior to coverage of the luminal region.

After 3 weeks in culture, a fully confluent smooth muscle cell layer was formed across the luminal surface of the vessel. Cell migration toward the outer region of the vessel was increased over the two week sample. While some immature cells were still visible on the luminal surface, no collagen fibers were visible.

Under histological staining (H&E and trichrome), cell infiltration was seen in the 2 and 3 week samples. While matrix remodeling was evident in the 2 week sample, it was far more pronounced in the 3 week sample. This remodeling appears to be more luminal, as a somewhat laminar layer of matrix is observed in that region. In addition, the 3 week samples demonstrated smooth muscle cell (SMC) infiltration throughout, as evidenced by equal cell density across the sample wall.

EXAMPLE 16

Demonstration of Ligament Design

To determine the feasibility of ligament design, 4.0 ml of 96% type I collagen and 4% elastin was electrospun onto a 25×25 mm square mandrel. The sample was electrospun using the same methods set forth in Example 8. The resultant mat was then fixed and seeded with fibroblast cells for 3 hours in a seeding chamber. The seeded mat was then placed in rotary cell culture for 1 week to allow cell infiltration. After 1 week in culture, the mat was held at both ends with sterile Teflon clamps and rotated clockwise at one end until resistance was felt. Additional fibroblasts were seeded to the twisted mat for 3 hours in a seeding chamber. The matrix was then removed and placed in rotary cell culture for another 1 week, after which it was fixed for SEM and histology.

Demonstration of Cartilage Design

Figure 12:
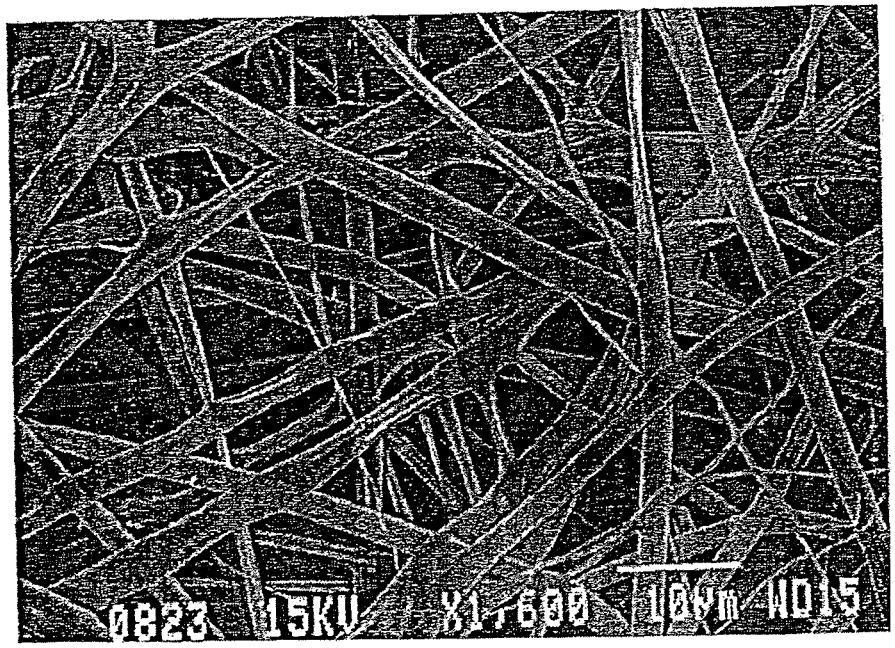
FIG. 12. Scanning electron micrograph of a fixed type II collagen matrix prior to seeding (scale size=10 um, magnification 1,600×).
Figure 13:
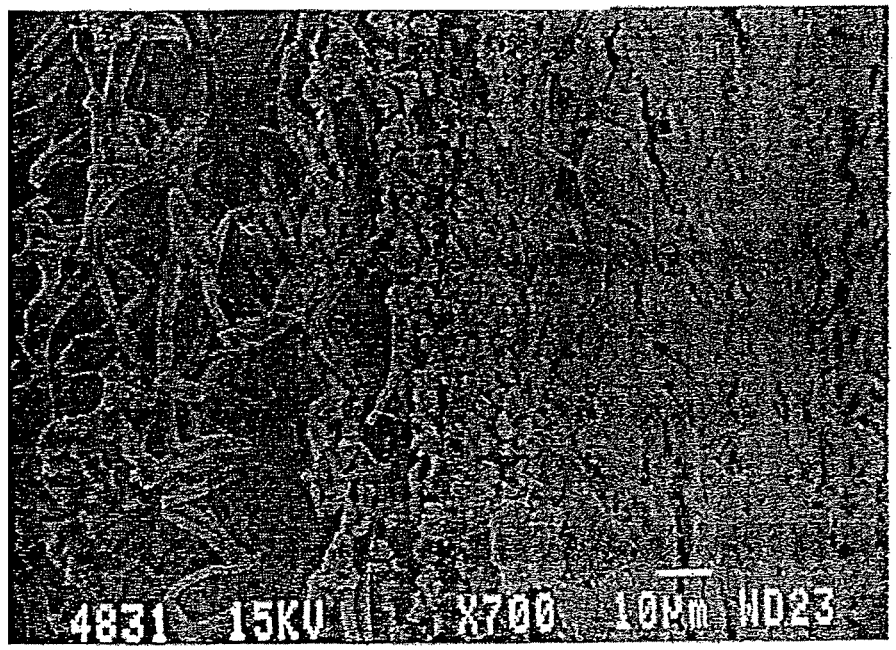
FIG. 13. Cross section of type II collagen mat after 1 week in culture with seeded chondrocytes. There is almost complete coverage to the seeded side (right) and some remodeling within the mat (immediate left) (scale size=10 um, magnification 700×).

For investigations of cartilage design, the feasibility of chondrocyte growth on electrospun type II collagen was determined. Initially, a 100 mg sample of type II collagen was placed into 1,1,1,3,3,3-hexafluoro-2-propanol (HFIP) at a concentration of 0.10 g/ml and electrospun. The sample was electrospun using the same methods set forth in Example 8. Once the entire 1 ml volume of type II collagen solution was spun, the resultant electrospun mats were removed from the mandrel and fixed in 3% glutaraldehyde gas to form a fixed type II collagen matrix, as shown by scanning electron microscopy (FIG. 12). A solution of chondrocytes suspended in media (1,000,000 cells) was then added to the matrix and placed in a seeding chamber for 3 hours. The mats were then removed from the chamber and cultured for 1 and 2 weeks respectively in a rotary cell culture system. The 1 week sample showed almost complete coverage on the seeded side and some remodeling within the mat (FIG. 13).

Demonstration of Three Layered Prosthetic Design

In an attempt to closely mimic the physiological protein distribution of a small diameter blood vessel matrix, a 3 ml mix of 80:20 collagen type I/elastin was produced at a concentration of 0.083 g/ml and electrospun onto a tubular (4 mm I.D.) mandrel, removed and fixed in 3% glutaraldehyde gas. The sample was electrospun using the same methods set forth in Example 8. Similar to a physiological vessel wall, this layer serves as the outer wall of the prosthetic to be seeded with fibroblasts and smooth muscle cells. The tube was tied closed at both ends with catgut suture, its outer surface was seeded with fibroblasts, and placed in a rotary cell culture system. After 4 days in culture the tube was removed, untied at one end, and a solution of suspended smooth muscle cells were injected into the tube lumen. The reopened end was then tied with suture and the tube was placed in culture for 4 days. While the first tube remained in culture, a second tube consisting of 70% elastin and 30% type I was electrospun onto a mandrel with a 2 mm i.d. After fixation, the 2 mm i.d. tube was slid into the 4 mm i.d. tube were and two were placed in rotary cell culture for 3 days. This was done to ensure SMC migration into the smaller tube. After 3 days in culture, human umbilical vein endothelial cells were injected into the inside of the 2 mm i.d. tube and cultured for 2 more days. The resultant prosthetic was then removed and fixed for histology.

EXAMPLE 17

Aqueous Electroprocessed Matrix of Nano-sized Fibers

In this embodiment water was used as solvent carrier to deliver rat tail collagen for electroprocessing. In order to increase the volatility of water, electrospinning was conducted in a vacuum. The device consisted of the standard electrospinning device consisting of a source solution (water/collagen), a high voltage source (30,000V), and a ground.

Vacuum flasks were linked in tandem and connected to a direct drive pump. The chamber used for electrospinning was capped with a rubber stopper. A 1 ml syringe equipped with a 30 gauge needle was passed through a port prepared in the stopper. A 2-way stop cock was positioned between the syringe source and the syringe. The syringe port was closed and the pump was initiated. The chamber was allowed to pump to a vacuum for 5-10 minutes. The total volume of the two vacuum flasks was approximately 6.25 liters. Once equilibrium was established, the hose connecting the pump to the first vacuum chamber was sealed with a clamp. The stop cock on the syringe was opened and the collagen solution (5 mg/ml collagen) was charged to 20-25 kV. Solvent initially dripped from the syringe source, as the voltage reached a critical level there was a transient formation of a Taylor cone and the subsequent formation of fibers. As the water evaporated and the vacuum dissipated the electrospinning processed ceased. SEM demonstrated that the fibers appeared to exhibit some fine substructure and evidence of a banded periodicity. Selected fibers approached mm in total linear length and fibers on the sub-micron scale in diameter.

EXAMPLE 18

Development of Tissue Engineered Heart Valves and Heart Valve Leaflets Utilizing an Electrospun Matrix A polymeric matrix is formed directly on a mandrel (mold) to produce a heart valve or heart valve leaflets. Reservoirs with attached micropipette tips (nozzles) are filled with the collagen solutions and polymeric solutions and placed at a distance from a grounded target. The grounded target is a metal mandrel (non-stick surface). A fine wire is placed in the solution within each pipette tip (spray nozzle) to charge the polymeric solution or melt to a high voltage. At a specific voltage, the polymeric solution or melt suspended in the pipette tip is directed from the tip of the pipette towards the grounded target (mandrel). This stream (splay) of solution begins as a monofilament which between the pipet tip and the grounded target is converted to multifilaments (electric field driven phenomena). This allows for the production of a "web-like" structure to accumulate at the target site. Upon reaching the grounded target, the multifilaments collect and dry to form the 3-D interconnected polymeric matrix (fabric). In experiments to test the efficacy of this approach, this technique was used to produce biodegradable filaments of polylactic/polyglycolyic acid (PLA/PGA; 50/50) polymers and poly(ethylene-co-vinyl acetate) both of which were dissolved in methylene chloride.

The electrospinning of the polymeric scaffoldings for the heart valves and heart valve leaflets could be random in orientation but are usually produced in specific orientations as described below. If the desired fiber orientation is longitudinal, then the mandrel/grounded target is moved perpendicular to the polymeric splay. This configuration allows the direct production of tubular matrices composed primarily of specifically (single orientation) orientated fibers.

The specific orientation in this case is any desired pitch with respect to the major axis of the grounded target. This orientation is controlled by the simultaneous rotation and longitudinal movement of the mandrel/grounded target. This permits the production of a matrix composed a specific pitch or an array of multiple pitches (cross-hatched configurations).

If biodegradable materials are utilized, substances such nucleic acids (vectors) are optionally added into the electrospinning polymeric solution for incorporation into the scaffold. Upon consumption/reorganization of the scaffolding by the seeded cells, the cells incorporate the vector (i.e. genetic engineering) into their DNA and produce a desired effect. Growth factors or other substances are optionally incorporated into the electrospun matrix to aid in tissue regeneration/healing.

EXAMPLE 19

Electrospin Coating of a Stent with Polymer Solutions

For this example, 1/7 wt/vol of polymer (95% PGA and 5% PCL) in HFIP was used. The applied voltage was 24.5 kV with a syringe tip to a stent surface (Palmaz-Schatz stent) at a distance of 7 inches. The spinning was performed for approximately 20-30 seconds. For spinning, the stent was mounted on a 25 gauge needle though the center and bent to a 90 degree angle at the end to hold the stent in place on the needle during the rotation of the stent/mandrel during electrospinning. The plastic mount of the syringe was taped to the end of a 4 mm diameter mandrel on a spinning apparatus for rotation during the electrospinning to obtain an even distribution of the coating. Deployment of the stent was performed by placing two 25 gauge needle though the stent lumen and physically pulling the stent open. The stent was uniformly coated with fibers of PGA-PCL, and its diameter was 83% greater than prior to deployment.

EXAMPLE 20

Electrospun Collagen Covered Stent Procedure

Figure 14:
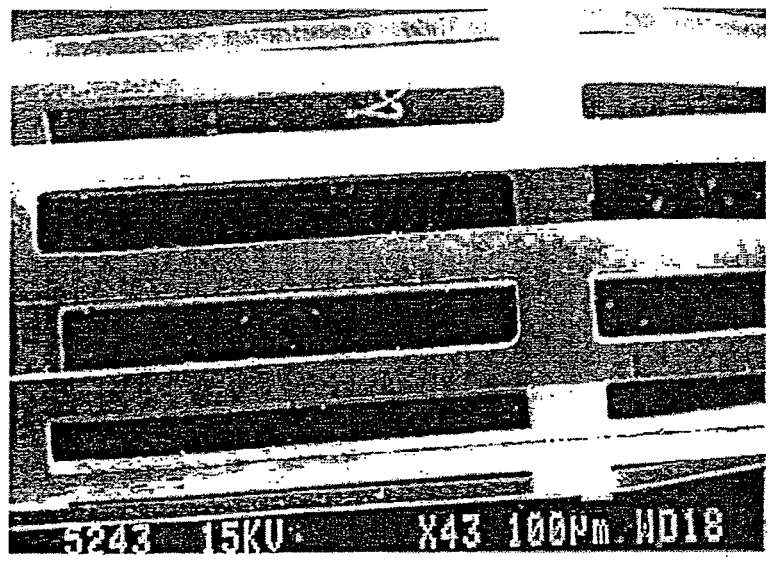
FIG. 14. Stent prior to collagen coating (scale size=100 um, magnification 43×).
Figure 15:
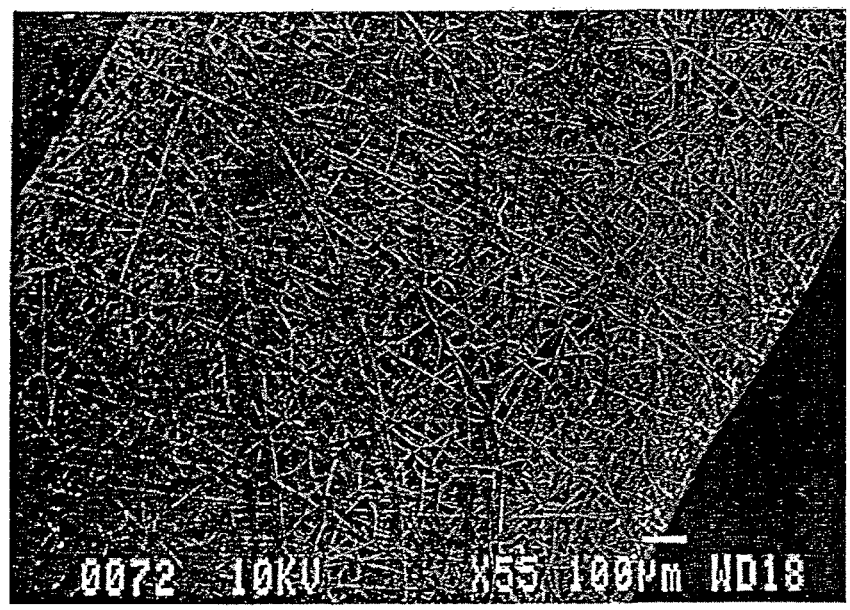
FIG. 15. Stent after coating (prior to cell seeding) with collagen nanofibers (scale size=100 um, magnification 55×).

A 25-gauge needle was inserted through the center of the stent (Palmaz-Schatz stent). To ensure that the stent remained on the needle during mandrel rotation, the tip of the needle was bent 90°. The needle and attached stent were then attached to the end of a metal mandrel extension (2 mm I.D.) After the stent was prepared, 0.080 g of collagen (rat tail Type 1) was placed into 1 ml of HFIP solution. The collagen solution was then placed into a 1 ml syringe and a 18 gauge blunt ended needle was attached. The sample was electrospun using the same methods set forth in Example 8. Approximately 400 μl of the solution was electrospun onto the stent. The stent was then removed from the needle and investigated under SEM. The results are compared in FIGS. 14 and 15. Electrospun collagen fibers coated the stent.

EXAMPLE 21

Vascular Tree Engineering

Electrospun fibers are formed on a mandrel of any shape. Thus, a vascular tree is made with multiple bifurcations that is one continuous structure without seams. An example is the electrospinning of a coronary bypass vascular tree for a quadruple bypass procedure. The mold can be even custom (3-D tailor made biomimicking structure) made or the vascular trees could be designed to average population specification with various sizes available.

A seamless rat aortic-iliac bifurcated graft was produced from polyethylvinylacetate. For this example the mold was formed from a stainless steel rod and a paper clip. The polymer was then electrospun to form the seamless bifurcation around the mold. The bifurcation was then just slipped off the mandrel as one seamless construct.

EXAMPLE 22

Electrospinning in Biomedical Engineering Applications: A Study of Muscle Bioengineering Electrospinning. PGA, PLA, PGA:PLA, and collagen were prepared suspended (7-8% weight per volume) in HFIP (Sigma, St. Louis). The various polymer solutions were loaded into a 1-ml syringe, charged to 20 kV and directed at a rotating, grounded mandrel across an air gap of 25-30 ems. Constructs used in this study were prepared on a 14-gauge needle and were 20-25 mm in length. The cylindrical constructs were removed from the mandrels and sterilized in 70% alcohol prior to use.

Cell Isolation. Neonatal rats were sacrificed and the skin was removed. Skeletal muscle was dissected from the limbs and thorax, minced and subjected to a 12-hour collagenase digestion (200-units/ml collagenase activity, Worthington Biochemical, N.J.). At the conclusion of the digest the tissue was cannulated, filtered through a 100 micron mesh filter and diluted in DMEM-F12 supplemented with 10% horse serum (Sigma, St. Louis) and 5% fetal bovine serum (Mediatech, Va.). Fibroblasts were partially purified from the isolate by two, one-hour cycles of differential adhesion. Partially purified satellite muscle cells were suspended in collagen (1 mg/ml) and placed into an electrospun, cylindrical construct. Isolated cells in the cylindrical constructs were cultured for 24 hours in a Synthecon Rotating Wall Bioreactor (Houston, Tex.) prior to implantation.

Surgical Procedures. Adult Sprague Dawley rats (150-200 gms) were anesthetized with pentobarbital. Fur over the hindquarter was removed. Skin was washed in betadine and an incision was prepared within the belly of the vastus lateralis. Cylindrical constructs were placed within the blind channel. The overlaying muscle was sutured over the implant and the skin incision was repaired. The entire area was then swabbed a second time with betadine. Implants were recovered seven days later and prepared for histological and ultrastructural examination. All tissue was routinely fixed for 24 hours in Karvonsky's fix prior to routine processing for light or transmission electron microscopy.

Preliminary implant experiments were conducted to characterize the biophysical properties of electrospun PGA, PLA, PGA:PLA, Type I collagen, or blends of Type I collagen and PGA:PLA. Adult Sprague Dawley rats (150-200 gms) were anesthetized and a small channel was prepared in vastus lateralis. Cylindrical constructs (electrospun on a 14 gauge needle, approximately 25 mm in length) composed of electrospun PGA, PLA, PGA:PLA blend (50:50), or a blend of Type I collagen: PGA:PLA (80:10:10) were prepared and placed into the channel. The distal ends of the electrospun constructs were sutured shut to form an enclosed cylinder. The constructs were then placed into the prepared channels. Blending small amounts of PGA:PLA with electrospun collagen produced a matrix of considerable material strength that accepted a suture. The electrospun matrix simultaneously functions as a fascial sheath and a tendonous insertion for the bioengineered muscle. Once the implants were in place the muscle was sutured shut over the implant and the skin incision was repaired. The objective of these experiments was to determine the extent to which the different materials integrate and allow the infiltration of cells from the surrounding tissue into the constructs. After one week the samples were recovered and prepared for microscopic evaluation.

Constructs of PGA were poorly integrated into the host tissue. A fibrotic capsule was clearly evident at the interface of the implant and the surrounding muscle tissue of the host. Giant cell macrophages were evident in domains immediately subjacent to the fibrotic capsule. Interstitial cells were almost completely excluded from the central cores of these implants; few cells invaded beyond the periphery of the construct. The central domains of the implants were occupied by remnants of the matrix and were nearly devoid of cells. Constructs composed of PLA did not promote the formation of the prominent fibrotic capsule that characterized the PGA implants. PLA supported low rates of cell infiltration and accumulated adipocytes, and implants exhibited a smoother transition zone with less fibrosis at the interface of the construct and the host tissue as compared to PGA. Cells were scattered throughout the cylindrical implants. Small caliber blood vessels were observed at the periphery of the PLA-based matrix. A subpopulation of cells within the PLA based implants stained intensely with osmium tetroxide and appeared to have accumulated lipids. The biophysical properties of the constructs composed of a 50/50 mixture of PGA:PLA were intermediate. A fibrotic zone at the edge of the implant was evident. A few large, multinucleated cells were present in the transition zone, however the PGA:PLA mixture did not appear to promote the accumulation of these cells to the same degree as PGA based constructs. Cellular infiltration was poor. Only a small number of cells invaded the central core of the constructs, large osmium-positive cells were absent.

In contrast to these results, implants fabricated from the Type I collagen: PGA:PLA fiber blends (80:10:10) and pure Type I collagen were fully infiltrated and densely populated with cells from the surrounding tissue. There was no evidence of a fibrotic capsule in the transition zone, which exhibited a smooth continuum of cells. Numerous functional blood vessels were present throughout the constructs. Cells within the electrospun matrix were elongated and oriented in parallel with the local axis of the electrospun matrix. The central domains of the implants were densely populated with a mixed population of cells. Mast-like cells were observed in some sections. The collagen-based matrix was well integrated into the host tissue and supported the formation of capillaries and arterioles. Cells within the scaffolds were intercalated within the fibrils of the matrix and aligned in parallel with the local axis of the electrospun collagen. The bundles of collagen in these domains exhibited the 67 nm repeat typical of the material prior to implantation. Supplementing collagen with FGF beta promoted the formation of myotubes in these implant.

Next, a Type I collagen-based matrix was investigated to determine how it would function as a platform for the delivery of exogenous cells to host tissue. Cylindrical constructs composed of electrospun Type I collagen PGA:PLA (80:10:10) or a 50:50 mixture of PGA:PLA were prepared. The constructs were sutured shut on one end and filled with a suspension enriched with satellite muscle cells. After satellite muscle cell supplementation the open end of the construct was sealed with a second set of sutures, forming a closed cylinder. The constructs were then placed within a channel prepared in the rat vastus lateralis. As before, the overlaying muscle tissue was sutured over the implants. After seven days the collagen-based implants were well integrated into the host tissue. There was no evidence of inflammation or fibrotic encapsulation. Overall, the constructs were densely populated with cells. Arterioles and capillaries were evident throughout the implants. As before, cells within the electrospun matrix were oriented in parallel with local orientation of the collagen filaments. Differentiating myotubes were concentrated in, but not limited, to these domains. In some restricted domains the myotubes were organized into parallel arrays. However, myotubes in other sections of the implant were often oriented along entirely different axis. The central cores of the implants were filled with cells, differentiating myotubes were occasionally observed. Functional blood vessels intermingled with the cells of the central core domain. In contrast to these results, bioengineered muscles fabricated on PGA:PLA platforms were encapsulated with a fibrotic capsule and were poorly integrated into surrounding tissue of the host. Large multi-nucleated cells lined much of the border zone along the interface of the implant and the endogenous tissue. The cell mass that did exist within the cylindrical constructs appeared to have delaminated from the internal walls of the implant.

In short-term implant studies the engineered tissue was placed in an unloaded state within the belly of the rat vastus lateralis muscle. To examine how mechanical forces associated with activity might impact the differentiation and integration of bioengineered muscle, tendon-to-tendon implant studies were conducted. Electrospun constructs composed of Type I collagen:PGA:PLA blends (80:10:10) were prepared, filled with a suspension enriched with satellite muscle cells and sealed. The engineered tissue was then passed deep to the belly of the vastus lateralis within the plane that separates this muscle from the underlying muscles of the quadraceps. The proximal end of the implant was sutured to the tendon of origin for the vastus lateralis muscle. The distal end was sutured to the tendonous insertion of this muscle. The incision was repaired and the rats were allowed to recover for eight weeks. During this interval the animals were routinely observed, there was no indication of discomfort, abnormal behavior or movement.

At recovery, the implanted tissue exhibited the classic light microscopic and ultrastructural characteristics of differentiated muscle. Tissue samples taken at the mid-point between the origin and insertion site exhibited parallel arrays of myotubes that were densely packed with myofibrils. Adjacent Z-bands were in full lateral registry in many of the myotubes. Subdomains within some of these myotubes were stained more intensely with the toluidine blue/crystal violet stain than adjacent subdomains. In contrast to these results, the myotubes located at the distal ends of the implants did not exhibit parallel alignment. In longitudinal sections, individual myotubes exhibited a convoluted profile. Within any given myotube the myofibrils were densely packed with the sarcoplasm and the Z-bands were in lateral alignment. The convoluted nature of these myotubes may reflect the fabrication process. These domains are in the immediate vicinity of the sutures used to enclose the constructs and subsequently anchor the implants to the tendonous attachments of the vastus lateralis. The mechanical forces placed across these domains may be very complex, resulting in differentiation but poor myotube alignment. At the ultrastructural level the engineered tissue exhibited parallel arrays of myofibrils interspersed with mitochondria. Sarcoplasmic reticulum invested these filaments and terminated in association with T tubules at the level of the Z bands. A small percentage of myotubes exhibited evidence of structural anomalies; sarcomeres with accessory banding patterns were evident. Electron dense bands were occasionally observed on either side of the Z-bands, near the A I border. Doublet M and H bands were also observed in some myotubes. This pattern of organization is observed in the muscle of the neonatal rat prior to full maturation of the muscle.

EXAMPLE 23

Electrospinning of Collagen from 2,2,2-Trifluoroethanol

The collagen used was Type I (rat tail, acid extracted). The collagen was suspended in 2,2,2-trifluoroethanol (TFE) at a concentration of 0.100 grams in 4 ml HFIP. Once in solution or suspension (solution a milky color), the solution was loaded into a 10 ml syringe plunger. A 18-gauge stub needle was then placed on the syringe to act as the electrospinning nozzle and charging point for the contained collagen solution. The filled syringe was placed in a syringe pump (KD Scientific) set to dispense the solution at rate of 11 ml/hr utilizing a Becton Dickinson 10-ml syringe plunger. The positive lead from the high voltage supply was attached to the stub adapter metal portion. The syringe pump was turned on and the high voltage supply turned on and set at 20 kV. The grounded target was a 303 stainless steel mandrel (0.6 cm W×0.05 cm H×4 cm L) placed approximately 6 inches from the tip of the adapter. In the experiment, the collagen solution was electrospun to form a nice, white mat on the grounded mandrel. After electrospinning, the collagen mat was removed from the mandrel and processed for scanning electron microscopy evaluation. The mat produced was approximately 100 microns thick. The average fiber size in this mat was 0.11±0.06 microns. The TFE does not modify the secondary structure of collagen, as shown by Fourier transform infrared spectroscopy.

EXAMPLE 24

Smooth Muscle Cell Migration in Electrospun Polylactic Acid) and Collagen/Elastin A scaffold for small diameter vascular graft development was constructed using electrospun collagen/elastin nanofibers and smooth muscle cell (SMC) migration into this scaffold was examined relative to an electrospun poly(lactic acid) scaffold. Four millimeter diameter tubes were electrospun from poly(lactic acid) (PLA) (Alkermes, Inc.) and 80:20 collagen (type I)/elastin, respectively, with a wall thickness in the range of 300-400 microns and a length of 1 cm. Samples were electrospun using the same methods set forth in Example 8. These cylindrical constructs were placed in a 55 ml STLV vessel (Rotary Cell Culture System, Synthecon, Inc.) with aortic smooth muscle cells (500,000 SMC/ml) for seeding. Culture media was changed every two days with no additional cells added. The scaffolds were removed from the STLV vessel and processed for scanning electron microscopy (SEM) and histological evaluations. Upon examination of the scaffolds, the electrospun collagen/elastin matrix revealed an average pore size of 3.7±1.6 microns and fiber dimension of 0.08±0.02 microns. While SMC migration was demonstrated through the scaffold wall after 1 week, cell migration was far more prominent after 2 weeks. After 3 weeks in culture, a fully confluent SMC layer was found on the external surfaces along with a high density of SMCs across the scaffold wall (even distribution throughout). Examination of the PLA scaffold revealed an average pore dimension of 26±4 microns and fiber dimension of 10±1 microns. The PLA grafts demonstrated limited SMC migration into the core of the wall. Even after 111 days, the cells formed a predominately confluent layer on the external surfaces of the cylindrical scaffold with sparse cells found in the cross-section of the scaffold.

The present results demonstrate that cells will migrate into scaffolds composed of electrospun collagen/elastin nanofibers with pore dimensions of a few microns, in contrast to current views that pore sizes of 10-30 microns will not allow cellular infiltration/migration. The electrospun collagen/elastin scaffolding does not follow the accepted paradigm as evidenced by the 3.7 micron average pore dimension results where one would expect little to no cellular migration into the core of the structure. Thus, upon a one order of magnitude decrease in pore size (vs. PLA), the SMCs immediately started to migrate into this fine pore diameter structure. These results support a paradigm in which cells will migrate into electrospun (nano-structured) collagen-based scaffolds with applications throughout the entire field of tissue engineering.

EXAMPLE 25

Electrospun Collagen/Polymeric Nano-Fiber and Nano-Pore Paradigm

Electrospun structures composed of polymeric nanofibers with nanopores have been made and provide a new paradigm for medical applications. Samples were electrospun using the same methods set forth in Example 8. SEM of a collagen type I electrospun matrix revealed complex branching of filaments with an average 0.1±0.04 microns in diameter. The pore diameter for this scaffold was 0.74±0.56 microns with a range from 0.2-2.3 microns. Smooth muscle cells were cultured with the matrix in a rotary culture system (Synthecon, Inc.). Electrospun collagen scaffolding after 21 days in culture showing extensive cellular infiltration of smooth muscle cells into the collagen nano-structured matrix with a even distribution of the cells across the entire cross-section of nano-structured scaffold produced.

In contrast, electrospun PLA permitted a slight (mostly a cell monolayer on the outer surfaces) migration of SMCs into the core of the structure, even after 111 days. The results demonstrate that cells will migrate into a sub-micron pore diameter structure created with electrospun nanometer collagen fibers.

EXAMPLE 26

Electrospinning Layered Laminates

A method to form multi-layered materials composed of fibers distributed along different orientations is described. This method provides the capability to form a template for the assembly of a multi-layered organ construct which does not require electrospinning cells directly into the matrix.

Matrix material, biocompatible polymers, blends or other materials are electrospun onto a rotating target mandrel. This mandrel is cylindrical, or any other desired shape. A rectangular target mandrel and collagen are used in this example although other materials and other shapes of mandrels may be employed and are considered within the scope of the present invention. The first layer of collagen is electrosprayed onto the mandrel, forming a layer of aligned filaments distributed along the axis of rotation. Next, in a second, distinct layer water soluble filaments such as PEG, PVOH, or other matrix is prepared over the first layer. This intermediate layer is sprayed from a separate source. To avoid disrupting the collagen layer it may be stabilized by UV cross-linking, chemical processing or other means prior to applying the water soluble layer. Next, a second layer of collagen is electrosprayed over the intermediate water-soluble layer (layer 2 is in this example). This third layer may be in the same orientation as the initial layer of collagen or in a different orientation than the initial layer of collagen. In making a heart or a blood vessel, this third layer is slightly offset with respect to the first layer (not quite along the same axis as the first layer-but slightly off axis to mimic the structural alignment of the intact heart). Next, the collagen layers are stabilized by using vapor fixation or other stabilizing agents. Processing for stabilization occurs after each successive layer to stabilize them to different degrees, or at the completion of the fabrication process on or off the target mandrel. Selective collagen layers or all collagen layers are optionally supplemented with additional substances like growth factors or other agents such as cDNA sequences, pharmaceuticals other peptides as described in the specification. Post processing of the constructs may also be conducted. The number of layers to be prepared varies with application and are essentially not limited.

Next the construct is optionally removed from the mandrel and immersed in water. This results in the selective removal of the water-soluble layers. Other solvent combinations are also possible in this design strategy and are not limited to the combination described in this description. If the collagen layers have been prepared along different tracks the end construct is composed of two different layers of collagen with slightly or very different polarities.

The construct is now prepared for cell seeding. In this example the distal end of the construct is sealed and cells are infiltrated into the central lumen (site where the mandrel existed). Cells are now in separate and distinct layers. This type of construct may be used for many applications such as the fabrication of a nerve guide. A cylindrical construct is selectively infiltrated with cells (or other materials) into the outer layer. Schwann cells, that surround and protect native nerve, may be used. This device can be used as nerve guide, since Schwann cells are in the location needed to infiltrate the inner cell layer and coat the nerve as it regenerates. The infiltration rate of cells across the inner collagen layer is optionally delayed by using a PGA:collagen formulation or a laminate of PGA, or accelerated by making the inner layer from collagen alone. In a nerve guide the addition of laminin and other basement membrane materials is optionally employed to accelerate, promote or support nerve re-growth. Gradients of growth factors are optionally used along the length of the construct.

In another application of this method, cell alignment may be controlled within a solid construct along a single axis. This type of construct is desirable for the fabrication of skeletal muscle, but is not limited to this application. An exterior sheath is prepared, in this example a cylindrical construct composed of collagen is described, but the invention is not limited to this type of design. Next a flat sheet of material is electrospun onto a rotating rectangular mandrel. A sheet composed of aligned collagen is fabricated and arrayed in parallel with the axis of rotation. The sheet is removed from the mandrel and rolled or folded in pleats (or as desired) in parallel with the axis of the fibrils. The sheet is now inserted (slid) into the outer cylindrical sheath. The resulting structure is composed of a cylindrical sheath that is "filled" with the pleated or rolled sheet of collagen. The end is sealed and filled with cells. The net result is a semi-solid cylinder that has an inner core of collagen fibrils (or other fibrils) arrayed along the long axis of the cylinder. Cells seeded into this type of construct will spread in parallel with the underlying fibrils of the pleated sheet. This invention is useful as a nerve guide, in formation of blood vessels, in formation smooth muscle based organs and other uses.

EXAMPLE 27

Comparison of Electrospun Collagen and Gelatin Implants

Constructs of electrospun calfskin gelatin (Sigma Aldrich, St. Louis, Mo.) were prepared and implanted using procedures essentially identical to those used to prepare the constructs of EXAMPLE 22. Both gelatin and blends of gelatin with a PGA/PLA polymer were used. Gelatin isolated from calfskin is identical in chemical composition to acid soluble collagen. However, during the processes used to isolate and to prepare gelatin for commercial distribution it is heat denatured and partially digested, events that markedly alter the biological properties of collagen. The fibrils of electrospun gelatin and electrospun acid soluble collagen were nearly identical in appearance. However, the fibrils of electrospun gelatin lacked the repeat banding pattern that was present in electrospun acid soluble calfskin collagen.

Upon recovery seven days after implantation, cylindrical constructs composed of non-banded fibrils of electrospun gelatin or a gelatin PGA/PLA copolymer blend delaminated from the host tissue during recovery. Microscopic examination revealed that these implants developed a fibrotic capsule and were poorly infiltrated with interstitial cells. The bulk of the cells present in these constructs exhibited the histological features of lymphocytes. While not wanting to be bound by the following statement, these data suggest that the banding pattern of electrospun acid soluble collagen may confer greater biocompatibility than that of gelatin. Implant studies described elsewhere herein demonstrate that electrospun collagen does not initiate any overt immune response and supports extensive cellular infiltration.

EXAMPLE 28

Electrospun Collagen Constructs Using Satellite Muscle Cells

A bioengineered organ was fabricated in vivo at the recipient site from a suspension of stem cells or a stem-cell like donor population. With respect to intact tissue, for example fully differentiated skeletal muscle, this type of donor source is less dense and exhibits a lower oxygen demand because it is non-contractile. Low oxygen demand is a characteristic that is desirable for any tissue that must be supported by the passive diffusion of nutrients from the surrounding environment until a functional circulatory system develops between the implant and the host. At the same time, it is also desirable for the scaffold to have sufficient mechanical integrity to support and define the initial structural properties of the tissue yet allow nascent blood vessels to penetrate the tissue engineered organ. It is also desirable for the scaffold to be degraded and replaced by constituents of the native ECM as the donor cells increase in density and differentiate to assume the structural features of mature tissue.

Skeletal muscle prostheses were prepared using electrospun collagen and the collagen PGA/PLA copolymer blend. The blends were prepared and electrospun using the procedures essentially identical to those described in EXAMPLE 22, above. Satellite muscle cells isolated from the three-day old neonatal rat were used as a donor source. Cylindrical electrospun constructs were then sealed on one end and filled with a suspension of satellite muscle cells. The remaining end of cylindrical construct was sealed and the muscle prosthetics were implanted within the rat vastus lateralis for seven days.

Satellite Muscle Cell Isolation. Neonatal rats (3 days old) were sacrificed by decapitation, the skin was removed and the remaining tissue was rinsed in PBS. Skeletal muscle was dissected from the limbs and trunk, minced and digested for 12 hr in collagenase (200 units/ml PBS collagenase activity, Worthington Biochemical, N.J.) at 37° C. The partially digested tissue was cannulated several times and diluted into DMEM-F12, passed through a 100 µm filter and centrifuged. Cell pellets were rinsed 2× by centrifugation (800×g) in fresh, serum-free DMEM F-12 media. Satellite muscle cells were partially purified from the crude digest by two, 45 minute intervals of differential adhesion and cultured for 24-48 hours in DMEM-F12 plus 10% horse serum, 10% fetal bovine serum and antibiotics.

Satellite muscle cells were trypsinized from the culture dishes, rinsed in fresh serum free media. One end of a cylindrical construct (2 or 4 mm I.D.) was sutured shut. The electrospun cylinder was placed in an upright position and filled with a suspension of satellite muscle cells ($1 \times 10^6$ cells/100 µml). After cell-supplementation, the open end of the cylinder was sutured shut, forming an enclosed cylinder filled with the cell suspension.

Surgical placement. In short term, seven day implant studies an adult Sprague Dawley rat (150-200 gm) was anesthetized to a surgical plane. Fur was removed from the hindquarters and the skin was washed in betadine. Electrospun constructs (20-25 mm in length) were implanted as cell-free, hollow enclosed cylinders and as enclosed cylinders supplemented with satellite muscle cells. These constructs were implanted into a blunt dissected channel prepared in the belly of vastus lateralis. Host muscle was sutured over the implants and the skin incision was repaired. Each treatment group in these short-term experiments was composed of 3-4 animals.

In long-term experiments (eight weeks) with full-length muscle implants the borders of the vastus lateralis were defined. A hemostat was passed deep to the vastus lateralis muscle and clamped to the distal end of the bioengineered muscle construct. The bioengineered muscle was then pulled under the vastus lateralis, and positioned external to the investing fascia within the plane that separates the vastus lateralis from the underlying muscles of the quadriceps. The implants were sutured to the tendons of origin and insertion for the vastus lateralis. At the conclusion of surgery the animals were placed on a warming pad until conscious.

For the recovery of implanted material animals were anesthetized to a surgical plane, the vastus lateralis was dissected free of the surrounding tissue, trimmed of excess mass and immersion fixed in one-half strength Karvonsky's fixative for 12 hours. Excess tissue surrounding the implanted materials was trimmed to define the outline of the implants. Constructs were cut in cross-section, embedded and thick sections were prepared for light and ultrastructural examination. For light microscopic images the tissue was stained with toludine blue/crystal violet solution.

Cell labeling experiments. Satellite muscle cells were incubated with DiI (1,1', di-octadecyl-3,3,3'3'-tetramethylindocarbocyanine perchlorate) or DiO (3,3'-dioladecyloxacarbocyanine perchlorate) from Molecular Probes Inc. (Eugene, Oreg.) for 12 hours, rinsed 3×-4× changes of fresh serum free media and sub-cultured for an additional 24 hours. Cells were trypsinized and seeded into electrospun cylinders composed of electrospun Type I collagen and implanted into the belly of the rat vastus lateralis muscle. After seven days the tissue was recovered. The vastus lateralis was removed in bloc, trimmed of excess mass and immersed in isopentane cooled to −30° C. Frozen tissue was cut in cross-section and examined by fluorescence and light microscopy.

Results. In 7 day implant studies, tissues fabricated with an electrospun matrix of only acid soluble collagen as well as tissues fabricated with collagen:PGA/PLA copolymer formulation were well integrated and fully invested by the host muscle. Muscle implants fabricated with electrospun collagen or with collagen:PGA/PLA were densely packed with cells and lacked a distinct transition zone. Small diameter muscle fibers were evident. Blood vessels were scattered throughout the implants. At the ultrastructural level the cells with a matrix of pure electrospun collagen exhibited highly elaborated rough endoplasmic reticulum. Differentiating myotubes and functional capillaries were scattered throughout these constructs. The myotubes exhibited centrally located nuclei and forming myofibrillar elements. Peripheral axons were occasionally encountered subadjacent to the basal lamina of these cells. Cell-labeling experiments were conducted to verify that the cells present within the muscle implants originated with the donor population that was implanted. Neonatal satellite muscle cells were labeled in culture with DiI or DiO, rinsed and used to fabricate a cylindrical prosthetic. After seven days in the rat vastus lateralis, the pre-labeled donor material was concentrated within the lumen and the wall of the implanted cylinders. A small number of labeled cells were observed within the surrounding muscle tissue of the host, suggesting that some donor cells had migrated out of the implant. Cell labeling experiments conducted with tissue metabolically labeled with bromodeoxyurdine yielded similar results. Muscle prosthetics fabricated with scaffolds of either electrospun gelatin or pure electrospun PGA/PLA delaminated from the host tissue during recovery and a fibrotic capsule was evident at the host implant interface. There was no evidence of muscle differentiation within these constructs.

Muscle Fabrication. These above data demonstrate that tissue-engineering scaffolds composed of electrospun collagen are biocompatible and can be used to deliver a viable population of donor satellite muscle cells to an intramuscular implant site. However, in the repair of a muscular defect, a prosthetic is likely to be placed at an extramuscular site. In order to determine if an extramuscular site can drive and support differentiation, a 4 mm inner diameter cylindrical construct was prepared composed of the collagen:PGA/PLA formulation. These constructs were sufficiently long to span the full length of the vastus lateralis. This scaffolding formulation was selected by empirical testing for further evaluation because this blend will readily accept and hold a suture without extensive cross-linking. The mechanical stability of an electrospun collagen-based matrix increases as a function of glutaraldehyde vapor fixation time. However, with longer fixation times, sub-micron diameter fibers present within the collagen-based matrix condensed into larger fibers and there was a concomitant reduction in the rate at which cells infiltrated the scaffold. Full-length constructs were supplemented with satellite muscle cells and passed deep to the vastus lateralis in the plane that separates this muscle from the underlying tissue of the quadriceps. The bioengineered tissue was anchored at either end to the tendons of the vastus lateralis. After eight weeks in situ the full-length muscle implants were recovered for analysis.

The implanted tissue was densely packed with myotubes that were distributed into parallel arrays along nearly the entire length of the prosthetic. Parallel arrays of myotubes terminated in a convoluted profile and were interspersed with functional blood vessels. Some myotubes stained in a regional pattern with toludine blue/crystal violet solution.

There was no discernable plasma membrane in these sites, suggesting this represents a true subdomain within a single myotube. Myotube alignment was less well defined at the distal attachment points. In tissue culture, matrix orientation and mechanical loads can interact to control the differentiation and alignment of striated muscle. The sutures used to anchor the muscle prosthetics clearly distort the electrospun scaffold and the mechanical loads carried across these attachment sites must be very complex, resulting in muscle differentiation but poor myotube alignment in these distal domains. Ultrastructural examination revealed parallel arrays of myofibrils surrounded by sarcoplasmic reticulum and interspersed with mitochondria. A subset of myotubes within the implants exhibited sarcomeres with accessory Z, M and H bands Within some of the implanted cells this cytoarchitectural feature was present immediately adjacent to myofibrils that exhibited normal sarcomeres. In some sites, myotubes that were densely packed with myofibrils resided immediately adjacent to myotubes with less densely packed contractile filaments.

These data demonstrate that an intramuscular implant site provides the appropriate cues to direct satellite cell differentiation. Further, functional microvascular networks develop in electrospun collagen over a time frame that is rapid enough to support the tissue. However, to repair a muscular defect, a prosthetic is often placed in an extramuscular site. With respect to an intramuscular site, an extramuscular site has lower rates of oxygen and nutrient exchange. To determine if an extramuscular site can drive and support differentiation, a bioengineered muscle fabricated with collagen:PGA/PLA was implanted deep to the vastus lateralis and anchored to the tendons of this muscle. After eight weeks in situ the bioengineered muscle consisted of parallel arrays of myotubes that terminated in a convoluted profile at the distal attachment sites. Matrix orientation and mechanical loads interacted to control the differentiation and architecture of muscle. While not wanting to be bound to a particular theory, it is believed that the sutures used to anchor the tissue distorted the matrix, resulting in differentiation but poor myotube alignment. Ultrastructural examination revealed parallel arrays of myofibrils surrounded by sarcoplasmic reticulum and interspersed with mitochondria. A subset of sarcomeres exhibited accessory Z, M and H bands. We have observed this banding pattern in muscle during post-natal differentiation and growth in the rat.

The electrospun collagen:PGA/PLA copolymer blend discussed above exhibited unique biophysical properties. This formulation withstood manual manipulation and accepted a suture, yet it supported rapid cellular infiltration and the formation of functional capillary beds.

EXAMPLE 29

Differentiation of Cells on an Electrospun Collagen Scaffold

Osteoblasts plated onto tissue culture plates coated with electrospun collagen stopped dividing and formed sub-confluent cultures. Human osteoblasts were purchased through Clonetics (US). Tissue cultures dishes were coated with electrospun collagen or electrospun gelatin. These materials were electrospun (80 mg/ml HFIP) directly onto the surface of the plates. Additional plates were coated with collagen that was electrospun with bone morphogenetic protein (BMP) in an amount of 50 nanograms along with 80 mg collagen in 1 ml HFIP. For comparison cells were plated onto uncoated plates (plastic surface) or plates were coated with a collagen gel. Cells (25,000) were plated onto the different surfaces, fed and examined daily.

Figure 16:
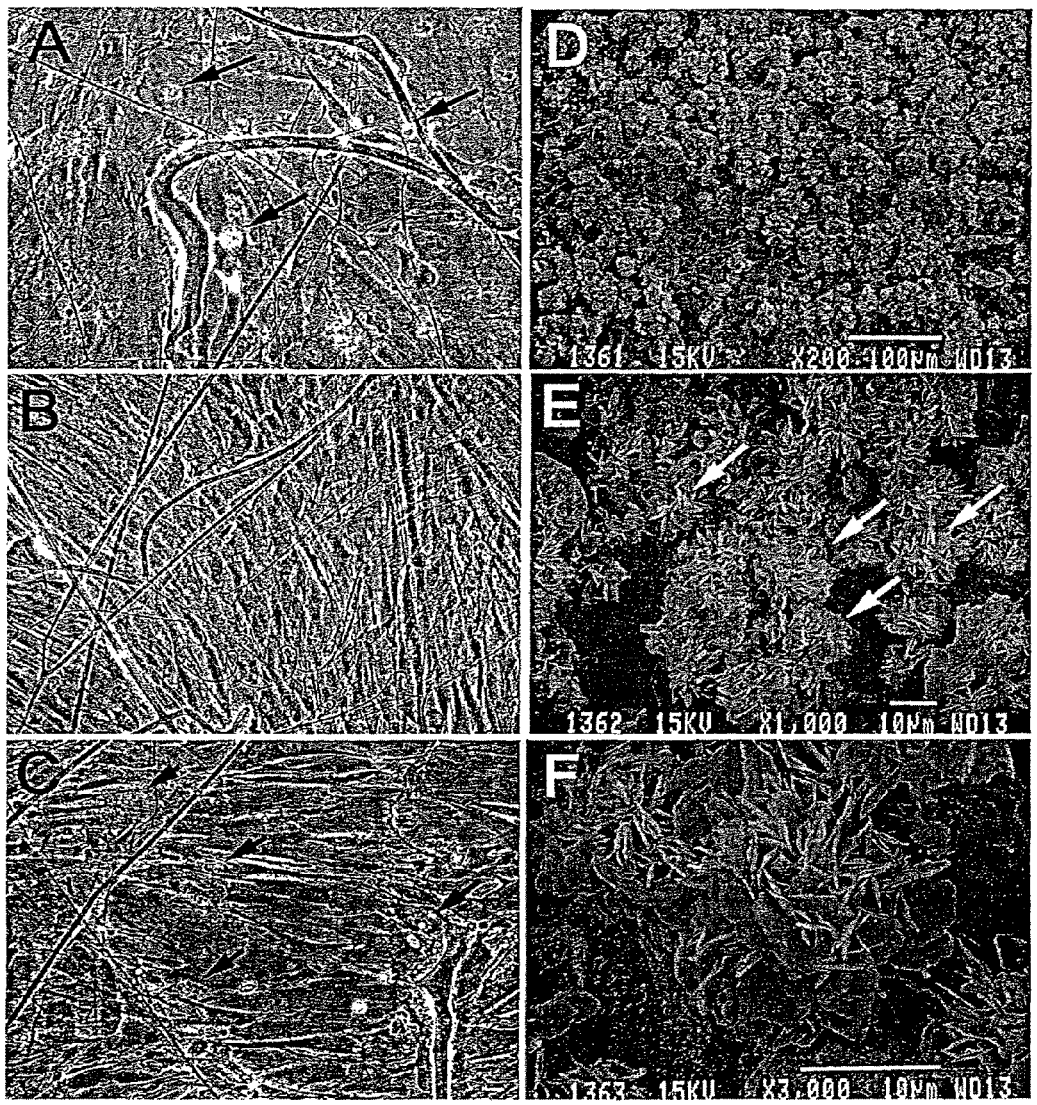
FIG. 16. Micrographs showing regulation of osteoblasts plated onto various substrates. Panel A depicts osteoblasts plated onto electrospun collagen fibers after eight days. Panel B depicts osteoblasts plated onto electrospun gelatin fibers after eight days. Panel C depicts osteoblasts plated onto fibers formed by electrospinning gelatin along with bone morphogenetic protein (BMP) after eight days. Panels D-F are scanning electron micrographs illustrate osteoblasts plated into a cylindrical construct of electrospun collagen for 14 days. Magnification for panels A-C is 20×. Magnification for panels D-F is as shown.

Within 3 days of plating the cells began to deposit phase bright granules of hydroxyapatite. Cells are shown at eight days in FIG. 16, panel A. The cultures retained these phenotypic characteristics for up to 14 days. In contrast, cells plated onto electrospun gelatin FIG. 16, panel B, a collagen gel, or tissue culture plastic (not shown), continued to divide and formed a confluent cell layer. There was no evidence of differentiation or hydroxyapatite deposition in these cultures even after 14 days. Large-scale electrospun fibers that are readily visible are marked by arrowheads (FIG. 16, panels A and B). Smaller scale fibers are obscured in these images because they are too small to see with light microcopy or are obscured by the cells in the field of view. When gelatin was electrospun with BMP cell division was suppressed and hydroxyapatite crystals accumulated on the surface of the cultures (FIG. 16, panel C). Co-electrospinning collagen with BMP did not obviously alter the rate of accumulation, the total amount or distribution of the hydroxyapatite crystals. Cells depicted in panels A-C of FIG. 16 were plated for 8 days. Panels D-F illustrates osteoblasts plated into a cylindrical construct of electrospun collagen for 14 days. The cells that were visible exhibited a rounded appearance, however the bulk of the cells were completely covered with a layer of hydroxyapatite crystals (E). Magnification A-C at 20×.

These data demonstrate that plating osteoblasts onto electrospun collagen is sufficient to suppress cell division and promote differentiation. Cells fail to differentiate when plated onto electrospun gelatin, however, differentiation can be driven on this type of surface by supplementing the matrix with the appropriate growth factors, in this example BMP. These data indicate that growth factors that are co-electrospun with collagen retain biological activity and are delivered to the culture media in an active form.

EXAMPLE 30

Articular Cartilage Scaffold

Collagen Electrospinning. Lyophilized, chicken sternal cartilage collagen type II was suspended in 1,1,1,3,3,3 hexafluoro-2-propanol (HFIP). All reagents were purchased through Sigma Aldrich unless otherwise noted. The collagen was electrospun at two concentrations (0.04 and 0.1 grams/ml). The collagen solution was loaded into a 1.0 ml syringe plunger with an 18 gauge stub-end needle placed on the syringe to act as the nozzle and charging point for the contained collagen solution. The filled syringe was placed on a syringe pump set to dispense the solution at rate of two milliliters per hour. The positive lead from the high voltage supply was attached to the stub-end metal portion to charge the collagen solution to 22 kV. A 303 stainless steel mandrel (0.1 cm W×0.6 cm H×2 cm L) was used as a ground target and was placed four inches from the tip of the needle. The collagen solution was electrospun to form a fibrous, microporous mat (approximately 300 microns thick) on the grounded mandrel. After electrospinning, the collagen mat was removed from the mandrel and processed for scanning electron microscopy (SEM) and chondrocyte seeding evaluation.

Scaffold Seeding. Chondrocytes were seeded onto electrospun scaffolds of Type II collagen to evaluate the biophysical properties of this material. A 100 mg sample of collagen type II was placed in HFIP at a concentration of 0.10 g/ml and electrospun. Once the entire volume (1 ml) of type II collagen solution was spun, its resultant electrospun mat was removed from the mandrel and fixed in a 3% glutaraldehyde vapor chamber for 15 hours at room temperature. The constructs were soaked in 70% isopropyl alcohol for 5 minutes followed by three washes in sterile phosphate buffered saline. Normal human articular chondrocytes (Clonetics Corp.), second passage, were suspended in culture media (1,000,000 cells in 1 ml) and plated onto scaffolds for 3 hours in a seeding chamber. The seeding chambers consisted of a round, hollow stainless steel cylinder with an inside diameter of 6.4 mm, total length 7 cm. Seeding chambers were rotated at ⅛ rotations per minute. The culture media was composed of 67% Dulbecco's Modified Eagle Medium (DMEM; high glucose with L-glutamine, sodium pyruvate and pyridoxine hydrochloride), 22% F-12 Nutrient Mixture, 15% fetal bovine serum, and 1% Penicillin-Streptomycin (10,000 Units/ml each). All media components were purchased from Gibco BRL Life Technologies. The mats were removed from the seeding chambers and cultured for 1 and 2 weeks respectively in a rotary cell culture system (RCCS) (Slow Turning Lateral Vessel (STLV); Synthecon, Inc., Houston, Tex.) that simulates microgravity (scaffold in continuous free-fall). This environment provides high mass transfer of nutrients in a buoyant, low shear environment under conditions that has been shown to foster cell-cell and cell-extracellular matrix (ECM) interactions.

Results and Discussion

SEM micrographs of electrospun collagen type II revealed scaffolds composed of polymerized collagen fibers with an average diameter of 1.75±0.9 microns (μm) and 0.11±0.09 μm for the electrospun solutions of 0.1 and 0.04 g/ml, respectively. The mats produced from one ml of starting solution were approximately 300 μm thick. Increasing or decreasing the volume of polymer solution or the dwell time of any given domain of a target mandrel modulated this parameter. The 110 nm electrospun fibers fabricated in this study approach the 80 nm diameter of Type II collagen fibrils observed in native tissue. The electrospun mats of collagen type II also possessed substantial structural integrity and withstood manual manipulation. Glutaraldehyde vapor fixed scaffolds of this material were stable in the cell culture environment.

Chondrocyte seeding studies demonstrate that electrospun scaffolds support cell growth and are readily infiltrated. SEM analysis of electrospun scaffolds seeded for one week revealed a sub-confluent layer of chondrocytes on the external surface of the matrix. Histological evaluation of the scaffolds revealed that chondrocytes were evenly distributed across the scaffold thickness with no overt changes in the structure of the matrix. After two weeks of culture, SEMs revealed a nearly confluent layer of cells on the external seeded surface of the scaffold. Histological examination of internal domains of the scaffolds indicates that a substantial degree of remodeling occurs as the cells penetrate the matrix. This observation demonstrates that chondrocytes can freely penetrate an electrospun matrix of Type II collagen. At present, the processes that mediate cellular infiltration remain to be defined, however the cells appear to actively degrade and redeposit collagen as they penetrate this type of matrix.

EXAMPLE 31

Small Caliber Vascular Construct
Collagen Electrospinning:

Acid soluble, lyophilized collagen was used for all experiments. Unless otherwise noted, all reagents were purchased from Sigma Chemical Company (St. Louis, Mo.). Type I collagen from calfskin and Type I and Type III collagen isolated from human placenta were used. Collagen was dissolved at various concentrations in 1,1,1,3,3,3 hexafluoro-2-propanol (HFIP). Suspensions of collagen were placed into a 1.0 ml syringe mounted in a syringe pump (Model 100, KD Scientific Inc., New Hope, Pa.). The syringe was capped with an 18-gauge blunt end needle. The positive lead from a high voltage supply (Spellman CZE1000R; Spellman High Voltage Electronics Corp.) was attached via an alligator clip to the external surface of the metal syringe needle. A grounded target (0.6 cm W×0.05 cm H×4 cm L) fabricated from 303 stainless steel was mounted 4-6 inches from the tip of the syringe tip. At the onset of electrospinning, the syringe pump was set to deliver the source solution at rates varying from 0-25 ml/hr. Simultaneously, the high voltage was applied across the source solution and the grounded target mandrel (15-30 kilovolts (kV)). The mandrel was rotated between 500 rpm and 5000 rpm. In summary, during the electrospinning process the isotype and concentration of collagen, imposed voltages, the air gap distance, and flow rates were examined as to their affects on the electrospinning process.

Cellular Interaction with Electrospun Collagen/Elastin:

Type I and III collagen and elastin were electrospun onto a 4 mm diameter cylindrical mandrel to form a culture scaffolding (length=1 cm). Constructs were cross-linked in glutaraldehyde vapor for 24 hours at room temperature and then rinsed through several changes of phosphate buffered saline. All cell culture experiments were conducted in a rotary cell culture system (RCCS) manufactured by Synthecon, Inc (Houston, Tex.) that was equipped with a Slow Turning Lateral Vessel (STLV). These devices are designed to maintain cells and tissue in continuous free fall, providing a buoyant, low shear environment and high mass transfer of nutrients. The buoyant environment of these devices fosters cell-cell and cell-matrix contacts and the formation of large cell masses. Rates of rotation necessary to suspend samples in continuous free fall were determined through routine experimentation. In this study, a rate of 10-11 rpm was sufficient to maintain the cylindrical constructs in free fall.

Cylindrical constructs were placed in a 55 ml STLV vessel with aortic smooth muscle cells (500,000 SMC/ml). The culture media was composed of Dulbccco's Modified Eagle Medium (DMEM) and F12 Nutrient Mixture (F12) (2:1—DMEM:F12 with high glucose plus L-glutamine, sodium pyruvate and pyridoxine hydrochloride) supplemented with 10% fetal bovine serum and 1% Penicillin-Streptomyocin (10,000 Units/ml). Culture media was changed after every two days with no additional cells added during the feeding intervals. Constructs were isolated for examination at specified intervals. All media components purchased from Gibco BRL Life Technologies.

Blood Vessel Fabrication:

In an attempt to closely mimic the physiological protein distribution of a small diameter blood vessel matrix, a 3 ml mixture of 40:40:20 collagen type I/collagen type III/elastin were electrospun onto a tubular (4 mm I.D.) mandrel, removed and fixed in 3% glutaraldehyde gas. The tube was tied closed at both ends with catgut suture; its outer surface was seeded with fibroblasts, and placed in a rotary cell culture system. After 4 days in culture the tube was removed, untied at one end, and a solution of suspended smooth muscle cells was injected into the tube lumen. The reopened end was then tied with suture and the tube was placed in culture for 4 days. While the first tube remained in culture, a second tube consisting of 70% elastin and 30% type I was electrospun onto a mandrel with a 2 mm I.D. After fixation the 2 mm I.D. tube was slid into the 4 mm I.D. tube and two were placed in rotary cell culture for 3 days. This was done to ensure SMC migration into the smaller tube since endothelial cell alignment is promoted in the presence of SMCs. After 3 days in culture, human umbilical vein endothelial cells were injected into the inside of the 2 mm I.D. tube and cultured for 2 more days.

The resultant vascular prosthetic was then removed and fixed for histology. Histological analysis revealed a three-layered prosthetic wall demonstrating defined intimal, medial, and adventitial layers.

EXAMPLE 32

Mechanical Behavior and Cellular Proliferation

Methods: Scaffold Preparation: Collagen Type II from chicken sternae (SIGMA, St. Louis Mo.) was dissolved in HFIP(SIGMA). A 5 ml syringe was filled with the collagen II/HFIP solution and placed onto a syringe pump (Model 100, KD Scientific Inc., New Hope, Pa.). The syringe tip was connected to a 30 kV voltage supply (Spellman CZE1000R; Spellman High Voltage Electronics Corp., Hauppauge, N.Y.) in order to charge the solution. A square (38 mm L×5 mm W×38 mm H) rotating, aluminum mandrel was placed perpendicular to the syringe tip. The solution was discharged from the syringe at a constant rate and fibers collected on the mandrel. After removal from the mandrel, the created scaffold was sectioned into dogbone scaffold specimens (long axis parallel to preferred fiber direction) and either mechanically tested or crosslinked for cell seeding and cell culturing. Crosslinking was achieved with a 24 hour, 3% vapor glutaraldehyde fixation technique. The seeding scaffold specimens were disinfected with a 5 minute ethyl alcohol wash followed by a 5 minute phosphate buffered saline wash. These disinfected scaffolds were then placed in 10 ml of culture media for at least 4 hours prior to seeding.

Cell Source: Immortalized adult human articular chondrocytes were cultured in DMEM/F-12 (GIBCO) with 10% fetal bovine serum (FBS) and 1% penicillin plus streptomycin. The cells were passaged every four to five days and used for cell seeding.

Scaffold Cell Seeding: Disinfected scaffolds were placed into a rotating seeding chamber along with approximately $5 \times 10^6$ to $10 \times 10^6$ cells and culture media supplemented with 50 μg/ml of ascorbic acid. The scaffolds were rotated for two hours in a 37° C. and 5% $CO_2$ incubator to complete the seeding.

Scaffold Culturing: Seeded scaffold specimens were removed from the seeding chamber and placed in a petri dish with an additional 10 ml of culture media supplemented with 50 μg/ml of ascorbic acid. The scaffolds were statically cultured for 7 days in a 37° C. and 5% $CO_2$ incubator. The culture media was changed every 2-3 days.

SEM Analysis: Uncrosslinked and crosslinked seeded scaffold specimens were processed for SEM analysis. The scaffold specimens were immersed and fixed at 4° C. in 2% glutaraldehyde prepared in Sorenson's buffer. Scaffold specimens were rinsed in cacodylate buffer and post-fixed in 1% osmium tetroxide for 1 hour. Scaffold specimens were sputter coated and examined. Average fiber diameter and scaffold pore size were determined with SEM photographs of uncrosslinked and crosslinked scaffold specimens with UTH-SCSA ImageTool 3.0.

Mechanical Testing: Uncrosslinked scaffold specimens were mechanically tested with an MTS tensile testing machine (MTS Systems Corp.; Eden Prairie, Minn.). Testing was performed at an elongation rate of 1 mm/min. The stress-strain analysis was completed using MTS Testworks software TestWork4 version 4.06A.

Statistical Analysis: Comparisons between groups were performed with a two sample t-test (n=4) and a Wilcoxon Rank-Sum test using NCSS 2000 statistical software.

Results: SEM analysis of the scaffolds revealed some longitudinal orientation of the collagen fibers and the adherence and proliferation of the chondrocytes on the scaffold. Tensile testing of the uncrosslinked scaffolds revealed a tangent modulus of 172.5 MPa and an ultimate tensile strength of 3.3 MPa. The average scaffold thickness for uncrosslinked specimens was 0.20 mm and the average scaffold thickness for crosslinked specimens was 0.52 mm. A minimum fiber diameter of 70 nm was measured in the uncrosslinked scaffold, while the average fiber diameter was 455 nm. The average fiber diameter of the crosslinked scaffold was 1.58 μm. The average pore area for uncrosslinked specimens was 6.94 μm². A significant difference was noted between the uncrosslinked scaffold and the crosslinked scaffold thickness and fiber diameter ($p<0.001$).

In summary, electrospun scaffolds of collagen type II, seeded and cultured with chondrocytes, may be useful for repairing damaged articular surfaces.

EXAMPLE 33

Delivery of Nerve Growth Factor (NGF) and Promoting Innervation of Implanted Electrospun Collagen A strategy was developed to promote the neo-innervation of a tissue-engineered skeletal muscle prosthesis. Neo-innervation refers to the process of nascent nerve growth into a tissue-engineered construct.

Collagen Extraction. Collagen was prepared by acid extraction of rat tail tendon or calfskin chorium. Samples were minced and incubated for 3-5 days in ice cold 0.01 M acetic acid. The extract was centrifuged for 16 hr at 4° C. at 15,900×g. The soluble fraction was supplemented with 5% NaCl, stirred overnight and centrifuged at 10,000×g for 5 hr. The supernatant was discarded and the pellets were dialyzed at a 10:1 ratio by volume through 3-5 changes with 18 Megohm ice cold water, and lyophilized. Calfskin gelatin was purchased from Sigma and was supplied as dry powder that is directly soluble in the solutions used for electrospinning. The gelatin was heat denatured prior to electrospinning.

Electrospinning For electrospinning, lyophilized Type I collagen was suspended in 2,2,2-trifluoroethanol (TFE: 80 mg/ml). This solution ("source solution") was aspirated into a 1 ml syringe equipped with a blunt stainless steel needle. An electrode was attached to the stainless steel needle. A rotating stainless steel cylinder ("target mandrel" 4 mm I.D.×50 mm in length) was positioned approximately five inches in front of the needle. This resulted in the formation of a continuous fibril that collected on the grounded target as a dry mat.

NGF Release From Collagen. For controlled release assays the collagen or gelatin electrospinning solutions were directly supplemented at a rate of 0, 500 or 1000 ng of 7S NGF per 80 mg of collagen per 1 ml of TFE. This NGF isolate was purchased from Chemicon (CA) and contained a biologically active isoform of the peptide. All electrospun samples were recovered from the target mandrel and vapor fixed in glutaraldehyde for 30 min. Glutaraldehyde vapor was used to stabilize the electrospun collagen and is an FDA accepted method for cross-linking collagen in human applications.

Microscopy. Representative samples of the electrospun materials were evaluated by Scanning Electron Microscopy to verify the structure of the constructs.

Controlled Release Studies. Samples were placed into 1.2 ml centrifuge tubes containing 1 ml of phosphate buffered saline and an antibiotic-antimycotic (Gibco #15240-062) in a ratio of 50:1 by volume. Aliquots of 100 μl were taken from each tube at 0, 1, 2, 4, 24, 36, and 92 hours. At each time point 100 μl of fresh PBS was added back to the samples to replace the 100 μl removed for analysis. Collected samples were frozen until analyzed. The amount of NGF present in the different samples was determined with a NGF ELISA assay (Chemicon # CYT304).

Cell Culture. PC-12 cells were purchased from the American Type Tissue Culture Association. Cells were expanded in suspension culture for 3-5 days and plated onto tissue culture dishes coated with Matrigel (Fisher). Samples of electrospun collagen supplemented with 1000 ng/ml NGF were embedded within the Matrigel. Equal numbers of PC-12 cells were plated into the culture dishes and observed at 12-24 hour intervals.

Figure 17:
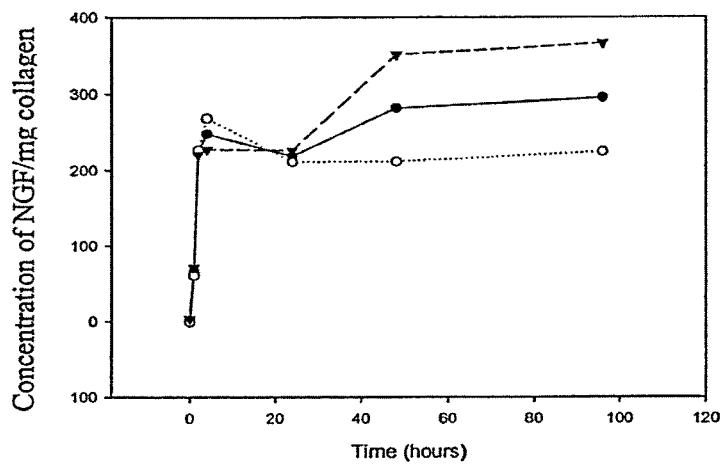
FIG. 17. Graph illustrating release of nerve growth factor from electrospun collagen matrices spun from solutions containing 500 nanograms of nerve growth factor (NGF) per 80 mg collagen. This figure depicts two separate runs of the same experiment (plots containing points illustrated as open circles and as triangles, respectively) and the aggregate average of the separate runs (plot containing points illustrated as solid circles). Data is expressed as total picograms (pg) of NGF released over time per mg of collagen.

It was determined that the release and recovery of NGF varied as a function of the starting concentration of the growth factor and the identity of collagen used in the assay. In samples supplemented with 500 ng NGF per 80 mg collagen, the release of growth factor was linear over the first 4-6 hours of the assay. These samples produced a maximum average concentration of 295 pg/ml for every mg of electrospun collagen present in the assay system (approximately 4.7% of total incorporated NGF in the electrospun sample). A representative release profile is illustrated in FIG. 17.

Figure 18:
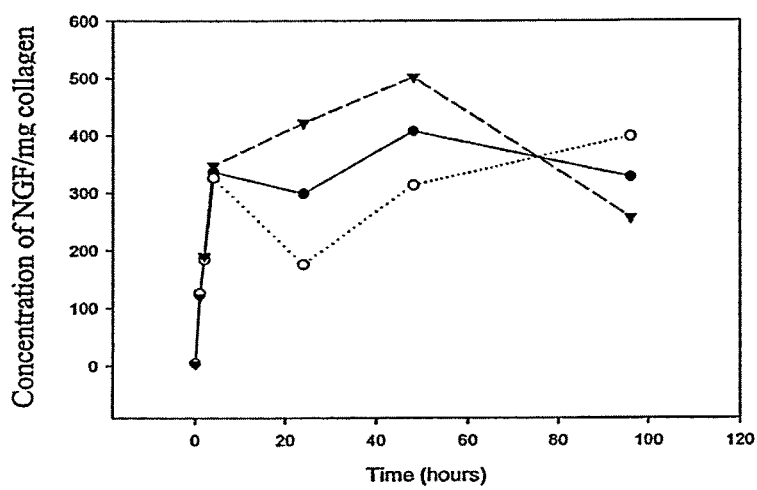
FIG. 18. Graph illustrating release of nerve growth factor from electrospun collagen matrices spun from solutions containing 1000 nanograms of nerve growth factor (NGF) per 80 mg collagen. This figure depicts two separate runs of the same experiment (plots containing points illustrated as open circles and as triangles, respectively) and the aggregate average of the separate runs (plot containing points illustrated as solid circles). Data is expressed as total picograms (pg) of NGF released over time per mg of collagen.

The release of NGF from samples supplemented with 1000 ng per 80 mg collagen is illustrated in FIG. 18. In these experiments the release profile over the first 4-6 hours of the experiment was very similar that observed with the 500 ng samples. However, the total amount released at any given time was proportionally higher than in the 500 ng samples. The maximum average concentration reached in these samples was 407 pg/ml/mg collagen (approximately 3.6% of total incorporated NGF in the sample).

The interaction of growth factors and other peptides with collagen in the native extracellular matrix can be determined by the structural properties of this natural polymer. To examine how the structure of electrospun collagen might regulate the release of NGF a series of experiments was conducted with electrospun gelatin.

Figure 19:
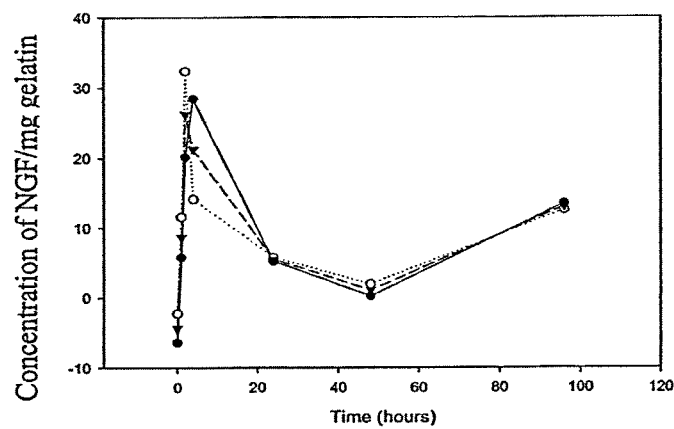
FIG. 19. Graph illustrating release of nerve growth factor from electrospun gelatin matrices spun from solutions containing 1000 nanograms of nerve growth factor (NGF) per 80 mg gelatin. This figure depicts two separate runs of the same experiment (plots containing points illustrated as open circles and as solid circles, respectively) and the aggregate average of the separate runs (plot containing points illustrated as triangles). Data is expressed as total picograms (pg) of NGF released per mg of gelatin.
Figure 20:
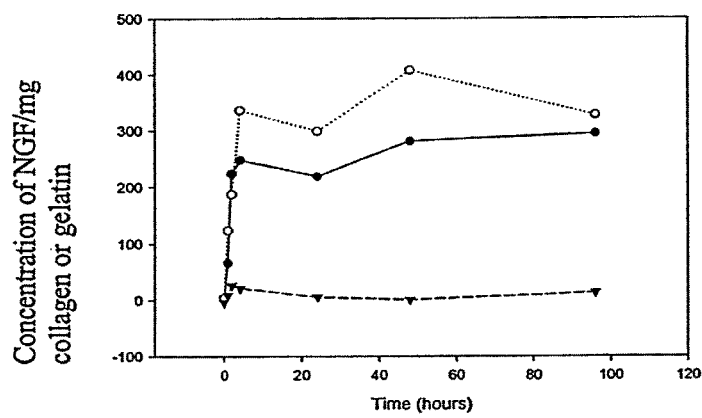
FIG. 20. Graph illustrating comparative results of the average release profiles of NGF from electrospun collagen and gelatin. Plot containing points illustrated as closed circles is release from electrospun collagen mat spun from a solution containing 500 ng NGF per 80 mg collagen. Plot containing points illustrated as open circles is release from electrospun collagen mat spun from a solution containing 1000 ng NGF per 80 mg collagen. Plot containing points illustrated as triangles is release from electrospun gelatin mat spun from a solution containing 1000 ng NGF per 80 mg gelatin. Data is expressed as total picograms (pg) of NGF released over time per mg of either gelatin or collagen.

Experiments with electrospun gelatin suggest that NGF is sequestered in this material in a way that appears to be fundamentally different from electrospun collagen. Samples of gelatin supplemented with 1000 ng NGF/80 mg released minute amounts of NGF during the first several hours of the assay. Subsequent to this initial interval the release of NGF was nominal or non-existent (FIG. 19). NGF released from gelatin only yielded a maximum average concentration of 26 pg/ml/mg gelatin (0.24% of total incorporated NGF).

The release of NGF from electrospun collagen is preferably tailored to the biological activity of the released peptide. NGF released from an electrospun matrix that does not exhibit biological activity cannot be used to direct cell behavior. To test the biological activity of NGF recovered from electrospun collagen, PC-12 cells were cultured in the presence of electrospun samples supplemented with 1000 ng NGF. Under baseline conditions these cells exhibit a nondescript fibroblast-like appearance and form cell clusters. When treated with a critical concentration of NGF they begin to express neurites (axonal like projections). Cultures of PC-12 cells treated with collagen supplemented with 1000 ng NGF/ 80 mg collagen exhibited increased evidence of cell spreading and neurite-like structures with respect to untreated controls. These data indicate the released NGF retained biological activity, as a higher concentration of NGF neurite outgrowth can be expected to occur.

Electrospun collagen appears to be an effective solid phase delivery platform for the delivery of NGF and potentially other growth factors to a local site. The kinetics of release for NGF appear to be predictable, and reproducible. The total amount of NGF released was proportional to the starting concentration of NGF present in the electrospinning solutions. The NGF released from electrospun collagen appears to retain of biological activity.

EXAMPLE 34

Treatment of Electrospun Collagen and Gelatin with Ammonia Vapors

Collagen and gelatin matrices were separately electrospun using methods set forth herein. Each matrix was removed from the target mandrel and placed into separate 100 mm tissue culture dishes. A 35 mm tissue culture dish was placed within the 100 mm dish. Within the 35 mm dish, 250 microliters of ammonia was added. The 100 mm dish was covered and allowed to incubate at room temperature for the desired period of time. At the conclusion of the incubation intervals, the samples were vapor fixed in gluteraldhyde and processed for microscopic evaluation.

A brief exposure (less than 1 hour) to ammonia vapors caused annealing or cross-linking of the fibers in both the electrospun collagen and the electrospun gelatin. Longer exposure to ammonia vapors resulted in the melding of the fibrous matrix into a more film-like or sheet-like structure. These structures possessed fibrils that projected up from the plane of the film, providing a site at which cells can attach.

EXAMPLE 35

Manipulation of Fiber Morphology Using Solvent Composition

Solutions containing TFE were prepared in which the solution contained 10% water, 20% water, 50% water and 75% water. Collagen was suspended at a concentration of 80 mg/ml in each of the solutions as well as a solution of pure TFE. When electrospun from pure TFE, collagen deposited as 1-5 micron diameter fibrils. The 10% water solution produced fibrils on the order of 1 micron or slightly less. The 20% water solution produced predominately sub-micron sized fibrils on the order of a 100 nm in diameter. For the 50% water solution the fibers exhibited evidence of forming a "beads on a string" pattern and were less than 100 nm in diameter. Other fibers in the 50% water example appear as ribbons, suggesting that water was trapped within the fiber during spinning, providing a potential site for the sequestration of materials, i.e. literally trapping the material within a fiber.

EXAMPLE 36

Manipulation of Fiber Morphology Using Solvent Composition and Flow Rate

Example 34 is duplicated except that the flow rate of solution from the syringes is increased and collagen is successfully electrospun from both the 50% and 75% water solutions without formation of the "beads on a string" morphology.

EXAMPLE 37

Layered Dermal Prosthesis

A dermal prosthesis is prepared and is composed of materials that maximize the onset of the natural healing process and minimize the risk of an adverse immune response. The dermal equivalent is a tissue-engineering scaffolding composed of electrospun Type I collagen, Type III collagen, and elastin fibers. The scaffolding exhibits a deep, reticular-like layer composed of randomly arrayed, large diameter fibrils of Type I collagen and elastin and a more superficial (papillary) layer composed of small diameter fibrils of Type III collagen and elastin deposited preferentially along a specific axis. Chondrotin-6-sulfate is blended throughout the scaffold. Process parameters (such as solvent selection and concentration of materials in the solvent) are manipulated to produce fiber diameters of the desired diameter.

To mimic the natural, gradual continuum between the two layers, the electrospinning process uses a total of four ports. Two ports deliver the reticular layer materials exclusively and another two ports deliver the papillary layer materials. Initially, more materials are deposited from the reticular layer ports, and emphasis shifts slowly to the papillary layer ports as the construct is prepared. Electrospinning from separate sources for each of the principle constituents of the dermis provides greater control over the viscosity of the electrospinning solutions, fiber composition and, ultimately, fiber diameter. The result is a dermal equivalent 70 mm×70 mm in surface area and 200 μm thick can be electrospun, prepared in about 20 minutes.

A microprocessor controls the rate and distribution of the deposition of the materials onto the target mandrel by providing supervisory control of multiple axis controllers for movement of the ground target mandrel (rotation, translation and pitch). This microprocessor controls each independent motor controller and acquires feedback from the controller to verify proper execution of the program. The microprocessor coordinates and synchronizes the motion of the individual motion controllers to allow precise deposition of fibers on the target mandrel. In addition to controlling the axis motion controllers, the microprocessor prompts the user to enter other process information including, but not limited to: port number, material concentration and solvent, applied voltage, mandrel information (shape, movement), nozzle to mandrel distance and injection flow source (reticular port 1 or port 2 and papillary port 1 or port 2 and "drug" port 1 and drug port 2) and rate.

To mimic the random orientation of the fibrils in native reticular layer, reticular constituents (large diameter fibrils of Type I collagen and elastin) are deposited onto a mandrel rotating at less than 1000 rpm. Electrospinning onto a target rotating at this rate produces a random array of fibrils. To produce fibrils on the order of 2 to 5 μm (and, optionally, up to 10 μm) in diameter for this layer of the dermal equivalent, 100 to 110 mg Type I collagen/ml HFIP and 100 to 110 mg elastin/ml of HFIP are used. The target mandrel is gradually accelerated to 5500-6000 rpm as the papillary layer begins to deposit. This acceleration results in the increased deposition of fibrils along a common axis. To produce nanoscale fibers for the papillary layer 70 to 80 mg Type III collagen (or less)/ml HFIP and 70 to 80 mg elastin (or less)/ml HFIP are used. Solutions are supplemented 2-5% chondroitin sulfate to assure distribution throughout the construct. Optionally, electrospinning solutions are supplemented with varying concentrations of silver ions. Further, polyglycolic acid/polylactic acid polymer containing tetracycline is optionally electrosprayed as nanospheres. The nanospheres are distributed throughout the construct by electrospraying them onto the target as the construct is formed.

All patents, patent applications, publications and abstracts cited above are incorporated herein by reference in their entirety. It should be understood that the foregoing relates only to preferred embodiments of the present invention and that numerous modifications or alterations can be made therein without departing from the spirit and the scope of the present invention as defined in the following claims.

We claim:

1. Dry electrospun collagen fibers, wherein said dry electrospun collagen fibers, prior to cross-linking, dissolve when exposed to water.

2. The dry electrospun collagen fibers of claim 1, wherein the electrospun collagen fibers have an average diameter of between about 30 nm and about 10 μm.

3. The dry electrospun collagen fibers of claim 1 wherein said dry electrospun collagen fibers are crosslinked.

4. A matrix comprising:
   dry electrospun collagen fibers, wherein said dry electrospun collagen fibers, prior to cross-linking, dissolve when exposed to water,
   wherein the matrix comprises pores having an average diameter of about 10 μm or less or having an average area between 0.1 square μm and 100 square μm.

5. The matrix of claim 4, wherein the matrix is crosslinked and has an elastic modulus of between about 2 MPa and about 10 MPa when hydrated.

6. The matrix of claim 4 wherein the dry electrospun collagen fibers have an average diameter of between about 30 nm and about 10 μm.

7. The matrix of claim 4 wherein said dry electrospun collagen fibers are positioned in layers where each layer has aligned filaments, and wherein aligned filaments in a first layer are aligned in a different direction from aligned filaments in a second layer.

8. The matrix of claim 4 wherein said dry electrospun collagen fibers are crosslinked.

* * * * *